(12) United States Patent
Gallagher et al.

(10) Patent No.: US 7,037,932 B2
(45) Date of Patent: May 2, 2006

(54) HETEROARYLOXY 3-SUBSTITUTED PROPANAMINES AS SEROTONIN AND NOREPINEPHRINE REUPTAKE INHIBITORS

(75) Inventors: Peter Gallagher, Basingstoke (GB); Richard Edmund Rathmell, Basingstoke (GB); Maria Ann Fagan, Basingstoke (GB)

(73) Assignee: Eli Lilly and Company, Indianapolis, IN (US)

( * ) Notice: Subject to any disclaimer, the term of this patent is extended or adjusted under 35 U.S.C. 154(b) by 204 days.

(21) Appl. No.: 10/476,137

(22) PCT Filed: May 6, 2002

(86) PCT No.: PCT/US02/11874

§ 371 (c)(1),
(2), (4) Date: Oct. 23, 2003

(87) PCT Pub. No.: WO02/094262

PCT Pub. Date: Nov. 28, 2002

(65) Prior Publication Data

US 2004/0176435 A1    Sep. 9, 2004

(30) Foreign Application Priority Data

May 18, 2001   (GB)   ................. 0112122.7

(51) Int. Cl.
- *A61K 31/343* (2006.01)
- *A61K 31/381* (2006.01)
- *A61K 31/404* (2006.01)
- *C07D 209/04* (2006.01)
- *C07D 333/52* (2006.01)

(52) U.S. Cl. .............. 514/415; 514/443; 514/469; 548/491; 549/51; 549/467

(58) Field of Classification Search .............. None
See application file for complete search history.

(56) References Cited

U.S. PATENT DOCUMENTS

| 4,956,338 A | 9/1990 | Rapp et al. |
| 4,970,232 A * | 11/1990 | Jakobsen et al. ........... 514/466 |
| 5,023,269 A | 6/1991 | Robertson et al. |

FOREIGN PATENT DOCUMENTS

| EP | 0 373 836 | 6/1990 |
| GB | 2 060 622 A | 5/1981 |
| WO | WO 0061539 | 10/2000 |
| WO | WO 0228815 | 4/2002 |

OTHER PUBLICATIONS

Jakobsen et al., STN International, HCAPLUS Database (2005), Columbus, OH, Accession No. 1989:614216.*

* cited by examiner

Primary Examiner—Kamal A. Saeed
Assistant Examiner—Andrew B. Freistein
(74) Attorney, Agent, or Firm—Arvie J. Anderson

(57) ABSTRACT

There is provided a heretoaryloxy 3-substituted propanamine compound of formula (I): wherein A is selected from —O— and —S—; X is selected from phenyl optionally substituted with up to 5 substituents selected from halo, $C_1$–$C_4$ alkyl and $C_1$–$C_4$ alkoxy, and thienyl optionally substituted with up to 3 substituents selected from halo and $C_1$–$C_4$ alkyl; Y is selected from benzothienyl, indolyl and benzofuranyl, optionally substituted with up to 5 substituents selected from halo, $C_1$–$C_4$ alkyl, $C_1$–$C_4$ alkoxy, nitro, acetyl and cyano; and when Y is indolyl it may be substituted or further substituted by an N-substituent selected from $C_1$–$C_4$ alkyl; $R_1$ and $R_2$ are each independently H or $C_1$–$C_4$ alkyl; and pharmaceutically acceptable salts thereof.

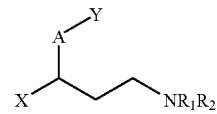

(I)

46 Claims, No Drawings

HETEROARYLOXY 3-SUBSTITUTED PROPANAMINES AS SEROTONIN AND NOREPINEPHRINE REUPTAKE INHIBITORS

This application is a §371 of PCT/US02/11874, filed on May 6, 2002.

This invention relates to novel heteroaryloxy 3-substituted propanamines, and to their use in inhibiting serotonin and norepinephrine reuptake.

Serotonin has been implicated in the aetiology of many disease states and has been found to be of importance in mental illnesses, depression, anxiety, schizophrenia, eating disorders, obsessive compulsive disorder (OCD) and migraine. Indeed many currently used treatments of these disorders are thought to act by modulating serotonergic tone. During the last decade, multiple serotonin receptor subtypes have been characterised. This has led to the realisation that many treatments act via the serotonergic system, such as selective serotonin reuptake inhibitor (SSRI) antidepressants which increase serotonin transmission, for example, the hydrochloride salt of fluoxetine.

Drugs that exert their main action on the norepinephrinergic system have been available for some time, however their lack of selectivity made it difficult to determine specific clinical effects produced by a selective action on norepinephrine reuptake. Accumulating evidence indicates that the norepinephrinergic system modulates drive and energy, whereas the serotonergic system modulates mood. Thus norepinephrine appears to play an important role in the disturbances of vegetative function associated with affective, anxiety and cognitive disorders. Atomoxetine hydrochloride is a selective inhibitor of norepinephrine, and is currently under development for the treatment of attention deficit hyperactivity disorder (ADHD).

Norepinephrine and serotonin receptors are known to interact anatomically and pharmacologically. Compounds that affect only serotonin have been shown to exhibit modulatory effects on norepinephrine, pointing toward an important relationship between the two neurotransmitter systems.

Duloxetine, (+)-N-methyl-3-(1-naphthalenyloxy)-2-thiophenepropanamine hydrochloride, inhibits the reuptake of both norepinephrine and serotonin, and is currently under development for the treatment of depression and urinary incontinence. The compound duloxetine was disclosed in U.S. Pat. Nos. 5,023,269 and 4,956,388.

U.S. Pat. No. 4,018,895 describes aryloxyphenyl propanamine compounds including compunds of the formula

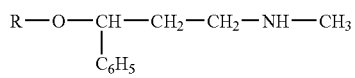

Where R is, for example, phenyl, substituted phenyl, tolyl or anisyl. The compounds block the uptake of various physiologically active monoamines including serotonin, norepinephrine and dopamine. Some of the compounds are selective to one of the monoamines and others have multiple activity. The compounds are indicated as psychotropic agents. Some are also antagonists of apomorphine and/or reserpine.

WO 00/02551 describes compounds which are active at the NMDA receptor and serotonin reuptake site.

WO 97/45115 describes compounds which inhibit glycine transport via the GlyT-1 or GlyT-2 transporters.

WO 96/09288 describes compounds which are active at the 5HT receptor.

The present invention provides novel heteroaryloxy propanamines which are potent inhibitors of both serotonin and norepinephrine reuptake.

According to the present invention there is provided a compound of formula I:

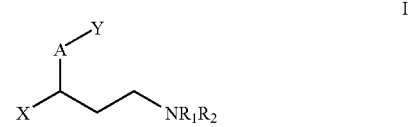

wherein
A is selected from —O— and —S—;
X is selected from phenyl optionally substituted with up to 5 substituents selected from halo, $C_1$–$C_4$ alkyl and $C_1$–$C_4$ alkoxy, and thienyl optionally substituted with up to 3 substituents selected from halo and $C_1$–$C_4$ alkyl;
Y is selected from benzothienyl, indolyl and benzofuranyl, optionally substituted with up to 5 substituents selected from halo, $C_1$–$C_4$ alkyl, $C_1$–$C_4$ alkoxy, nitro, acetyl and cyano;
and when Y is indolyl it may be substituted or further substituted by an N-substituent selected from $C_1$–$C_4$ alkyl;
$R_1$ and $R_2$ are each independently H or $C_1$–$C_4$ alkyl;
and pharmaceutically acceptable salts thereof.

A sub-group of compounds acording to the present invention includes compounds of formula I wherein A is —O—;
X is selected from phenyl, and thienyl optionally substituted with a substituent selected from halo and $C_1$–$C_4$ alkyl;
Y is selected from benzothienyl, benzofuranyl and indolyl optionally substituted with one to three substituents from the groups halo, $C_1$–$C_4$ alkyl, $C_1$–$C_4$ alkoxy and cyano;
$R_1$ and $R_2$ are each independently H or $C_1$–$C_3$ alkyl;
and pharmaceutically acceptable salts thereof.

The compounds of the present invention are potent and selective inhibitors of serotonin and norepinephrine reuptake.

In one group of compounds according to the present invention, A is —O—.

In another group of compounds according to the present invention, A is —S—.

Preferably, one of $R_1$ and $R_2$ is H.

$R_1$ and $R_2$ may both be H. Alternatively, one of $R_1$ and $R_2$ may be H while the other is $C_1$–$C_4$ alkyl, for example $C_1$–$C_3$ alkyl. When one of $R_1$ and $R_2$ is $C_1$–$C_4$ alkyl, said $C_1$–$C_4$ alkyl may be substituted with for example a $C_3$–$C_6$ cycloalkyl group. Preferably, the $C_1$–$C_4$ alkyl group is unsubstituted. Preferably, one of $R_1$ and $R_2$ is H and the other is methyl.

When X in formula I above is substituted phenyl, it is preferably mono- di- or tri-substituted with halo, $C_1$–$C_4$ alkyl and/or $C_1$–$C_4$ alkoxy. Halo substituents include F, Cl, Br and I, preferably F or Cl.

$C_1$–$C_4$ alkyl substituents include unsubstituted straight or banched alkyl groups of 1, 2, 3 or 4 carbon atoms, optionally substituted with for example one or more halogens, for example F. Preferred $C_1$–$C_4$ alkyl substituents include methyl and trifluoromethyl. $C_1$–$C_4$ alkoxy substituents include unsubstituted and substituted alkoxy groups of 1, 2, 3, or 4 carbon atoms, linked through the —O— atom; suitable substituents include halogens, for example F, as in —$OCF_3$. A preferred $C_1$–$C_4$ alkoxy group is methoxy.

When X in formula I above is substituted thienyl, it is mono-, di- or tri-substituted. Halo substituents include F, Cl, Br and I, preferably F or Cl. $C_1$–$C_4$ alkyl substituents include unsubstituted straight or banched alkyl groups of 1, 2, 3 or 4 carbon atoms, and corresponding substituted groups—suitable substituents include halogens, for example F. Preferred $C_1$–$C_4$ alkyl substituents include methyl and trifluoromethyl. When X is thienyl it is preferably thien-2-yl.

In a preferred embodiment of the present invention, X is phenyl or substituted phenyl.

In a particular embodiment of the present invention, Y is indolyl. In a preferred embodiment, Y is benzofuranyl. In another preferred embodiment, Y is benzothienyl. A preferred point of attachment of the group Y to the —O— or —S— atom is attachment at the 7-position. Attachment at the 4-position is further preferred. Other points of attachment, for example 5- and 6- are also possible.

When Y is N-substituted indolyl, the substituent is preferably Me. When Y is substituted benzothienyl, indolyl (with or without N-substitution) or substituted benzofuranyl, there may be 4 or 5 substituents, but mono- di- or tri-substitution is preferred, for example di-substitution, or mono-substitution. Halo substituents include F, Cl, Br and I, preferably F or Cl. $C_1$–$C_4$ alkyl substituents include unsubstituted straight or branched alkyl groups of 1, 2, 3 or 4 carbon atoms, and corresponding substituted groups—suitable substituents include halogens, for example F. Preferred $C_1$–$C_4$ alkyl substituents include methyl and trifluoromethyl.

Especially preferred compounds are those in which X is phenyl and Y is benzothienyl, particularly halo-substituted benzothienyl and more particularly F-substituted benzothienyl; and especially where one of $R_1$ and $R_2$ is H and the other is Me.

The present invention also provides processes for producing a compound of formula I above, which comprises reacting a compound of the formula II:

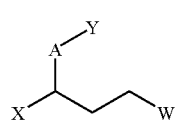

II where A, X and Y are as formula I above, and W is a leaving group, with an alkyl amine. Examples of suitable leaving groups include halo, mesylate and tosylate, but the nature of the leaving group is not critical. The reaction is carried out in a sealed vessel with a lower alkyl alcohol as solvent.

Compounds of the present invention are selective inhibitors of the reuptake of both serotonin and norepinephrine and as such are useful as pharmaceuticals. They are particularly useful for the treatment of pain.

For clinical purposes, pain may be divided into two categories: acute pain and persistent pain. Acute pain is provoked by noxious stimulation produced by injury and/or disease of skin, deep somatic structures or viscera, or abnormal function of muscle or viscera that does not produce actual tissue damage. On the other hand, persistent pain can be defined as pain that persists beyond the usual course of an acute disease or a reasonable time for an injury to heal or that is associated with a chronic pathologic process that causes continuous pain or the pain recurs at intervals for months or years. If pain is still present after a cure should have been achieved, it is considered persistent pain. For the purpose of the present invention, persistent pain can be chronic non-remitting or recurrent. The difference in definition between acute and persistent pain is not merely semantic but has an important clinical relevance. For example, a simple fracture of the wrist usually remains painful for a week to 10 days. If the pain is still present beyond the typical course of treatment, it is likely that the patient is developing reflex sympathetic dystrophy, a persistent pain syndrome that requires immediate effective therapy. Early and effective intervention potentially prevents the undue disability and suffering, and avoids the potential development of a condition that becomes refractory to therapy.

Acute and chronic pain differ in etiology, mechanisms, pathophysiology, symptomatology, diagnosis, therapy, and physiological responses. In contrast to the transitory nature of acute pain, persistent pain is caused by chronic pathologic processes in somatic structures or viscera, by prolonged and sometimes permanent dysfunction of the peripheral or central nervous system, or both. Also, persistent pain can sometimes be attributed to psychologic mechanisms and/or environmental factors.

Current therapies for persistent pain include opiates, barbiturate-like drugs such as thiopental sodium and surgical procedures such as neurectomy, rhizotomy, cordotomy, and cordectomy.

The compounds of the present invention are indicated in the treatment of persistant pain and references herein to pain are intended to refer to persistent pain.

In addition to the compounds of formula I and processes for the preparation of said compounds, the present invention further provides pharmaceutical compositions comprising a compound of formula I or a pharmaceutically acceptable salt thereof, together with a pharmaceutically acceptable diluent or carrier.

Further, the present invention provides a compound of formula I or a pharmaceutically acceptable salt thereof, for use as a pharmaceutical; and a compound of formula I or a pharmaceutically acceptable salt thereof, for use as a selective inhibitor of the reuptake of both serotonin and norepinephrine.

The present compounds and salts may be indicated in the treatment of disorders associated with serotonin and norepinephrine dysfunction in mammals, including depression, OCD, anxiety, memory loss, urinary incontinence, conduct disorders, ADHD, obesity, alcoholism, smoking cessation and pain. The compounds of the present invention are particularly suitable for the treatment of pain.

The present invention also provides the use of a compound of formula I, or a pharmaceutically acceptable salt thereof, in the manufacture of a medicament for selectively inhibiting the reuptake of serotonin and norepinephrine; the use of a compound of formula I, or a pharmaceutically acceptable salt thereof, in the manufacture of a medicament for the treatment of disorders associated with serotonin and norepinephrine dysfunction in mammals; the use of a compound of formula I, or a pharmaceutically acceptable salt thereof, in the manufacture of a medicament for the treatment of a disorder selected from depression, OCD, anxiety, memory loss, urinary incontinence, conduct disorders, ADHD, obesity, alcoholism, smoking cessation and pain; and the use of a compound of formula I, or a pharmaceutically acceptable salt thereof, in the manufacture of a medicament for the treatment of a disorder selected from depression, urinary incontinence, particularly stress induced urinary incontinence, and more especially, pain. The present invention further provides a compound of formula I for treating disorders associated with serotonin and norepinephrine dysfunction in mammals, for example a disorder selected from depression, OCD, anxiety, memory loss, urinary incontinence, conduct disorders, ADHD, obesity, alcoholism, smoking cessation and pain, especially depression, urinary incontinence, particularly stress induced urinary incontinence, and, more especially, pain.

Further the present invention provides a method for selectively inhibiting the reuptake of serotonin and norepinephrine in mammals, comprising administering to a patient in need thereof an effective amount of a compound of formula I or a pharmaceutically acceptable salt thereof; a method for treating disorders associated with serotonin and norepinephrine dysfunction in mammals, comprising administering to a patient in need thereof an effective amount of a compound of formula I or a pharmaceutically acceptable salt thereof; and a method for treating a disorder selected from depression, OCD, anxiety, memory loss, urinary incontinence, conduct disorders, ADHD, obesity, alcoholism, smoking cessation and pain, comprising administering to a patient in need thereof an effective amount of a compound of formula I or a pharmaceutically acceptable salt thereof.

The term $C_1$–$C_3$ alkyl herein represents a straight or branched alkyl chain bearing from one to three carbon atoms. $C_1$–$C_4$ alkyl represents a straight or branched alkyl chain bearing from one to four carbon atoms. Typical $C_1$–$C_3$ alkyl groups include methyl, ethyl, n-propyl and isopropyl. Typical $C_1$–$C_4$ alkyl groups include methyl, ethyl, n-propyl, isopropyl, n-butyl and t-butyl. A $C_1$–$C_4$ alkoxy group is a $C_1$–$C_4$ alkyl group linked through oxygen to the heterocyclic nucleus. The term halo represents any of the groups fluoro, chloro, bromo and iodo. When X is thienyl it can be either 2-thienyl or 3-thienyl. The terms alkyl and alkoxy may include substituted alkyl and alkoxy groups, particularly halo-substituted, for example F-substituted groups.

The present invention includes the pharmaceutically acceptable salts of the compounds of formula I. Suitable salts include acid addition salts, including salts formed with inorganic acids, for example hydrochloric, hydrobromic, nitric, sulphuric or phosphoric acids, or with organic acids, such as organic carboxylic acids, for example pyruvic, lactobionic, glycolic, oxalic, maleic, hydroxymaleic, fumaric, malic, tartaric, citric, salicylic, o-acetoxybenzoic, or organic sulphonic, 2-hydroxyethane sulphonic, toluene-p-sulphonic, bisethanesulphonic acid or methanesulphonic acid.

In addition to the pharmaceutically acceptable salts, other salts are included in the invention. They may serve as intermediates in the purification of compounds or in the preparation of other, for example pharmaceutically acceptable, acid addition salts, or are useful for identification, characterisation or purification.

While all the compounds of the present invention are believed to inhibit the reuptake of serotonin and norepinephrine in mammals there are certain of these compounds which are preferred for such uses. Preferred values for X, Y, $R_1$ and $R_2$ and substituents for each have been set out above.

Other compounds include compounds of formula I when A is —O— and subject to one or more of the following:

when X is substituted thienyl it is preferably substituted with Cl or Me, most preferably in the 5 position;

when Y is 1-benzothienyl it is preferably 1-benzothien-7-yl or 1-benzothien-4-yl; when Y is indolyl it is preferably indol-7-yl or indol-4-yl;

when Y is 1-benzothien-7-yl, or indol-7-yl optionally substituted with one to three substituents including substituents from the groups halo, $C_1$–$C_4$ alkyl, $C_1$–$C_4$ alkoxy and cyano, the respective groups are preferably in the 2, 3 and/or 4 positions; when Y is 1-benzothien-4-yl or indol-4-yl optionally substituted with one to three substituents including substituents from the groups halo, $C_1$–$C_4$ alkyl, $C_1$–$C_4$ alkoxy and cyano, the respective groups are preferably in the 2, 3 and/or 7 positions;

when Y is substituted 1-benzothienyl, 1-benzofuranyl or indolyl it is preferably substituted with one to three substituents from the groups fluorine, chlorine, methyl, methoxy and cyano, more preferably fluorine, chlorine and methyl; more preferably, both X and Y are unsubstituted;

preferably, one of $R_1$ and $R_2$ is methyl; more preferably, one of $R_1$ and $R_2$ is hydrogen and the other is methyl.

It will be appreciated that compounds of formula I possess an asymmetric carbon atom, and that they exist in the form of individual stereoisomers, as well as the racemic mixture. When the stereoisomeric form of a compound is not indicated in this document, it will be understood that both of the possible isomeric forms, as well as the racemate, are intended. When an individual stereoisomer is indicated, the isomeric form will be stated as part of the name.

Compounds of the present invention may be prepared by conventional organic chemistry techniques. For example, where X is phenyl the chiral alcohols are commercially available from the Aldrich Chemical Company in pure enantiomeric form and can be used without further purification.

Additionally, the chloropropanols which are commercially available from the Aldrich Chemical Company may be converted via a Finkelstein reaction using sodium iodide in acetone under reflux conditions to the corresponding iodopropanols and these may be used as an alternative to the chloropropanols.

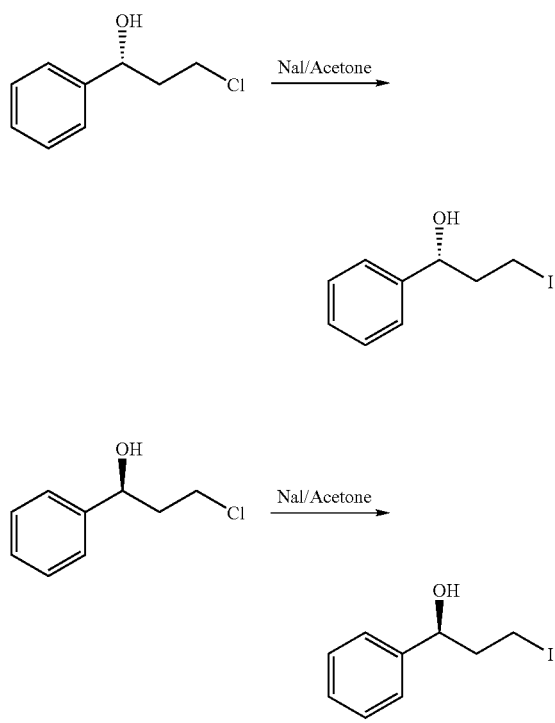

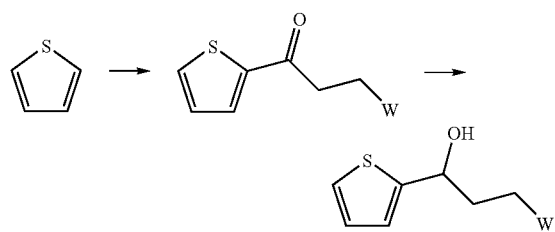

Where X is thienyl the corresponding thienyl-propanols can typically be prepared generally as follows (W is as defined above):

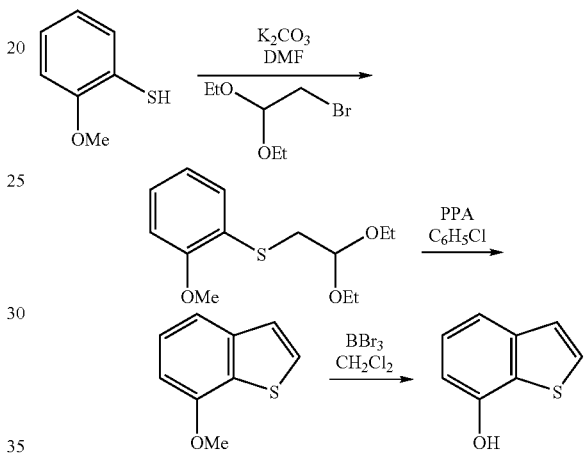

Subjecting thiophene to classical Friedel-Crafts acylation with an acid chloride such as chloropropionyl chloride in roughly equal quantities, with a strong Lewis acid such as aluminium chloride in a non-protic solvent such as dichloromethane or dichloroethane at temperatures ranging from −5° C. to reflux can result in the desired thienyl ketone. This ketone can be readily reduced to the desired alcohol either racemically using standard reducing agents such as sodium borohydride in a protic solvent such as the lower order alkyl alcohols, or Borane-THF complex in a polar non-protic solvent such as diethyl ether or THF. Chiral reduction of the ketone can be performed using a boron based chiral reducing agent in which high enantiomeric excesses can be obtained. Further details regarding this procedure can be found in J. Labelled Compd. Rad., 1995, 36, (3), 213 and references therein.

The benzothiophenes of the invention have been made by several routes. Thus a preferred route is by the alkylation of a thiophenol derivative with bromoacetaldehyde diethyl acetal followed by subsequent acid catalysed cyclisation with polyphosphoric acid in chlorobenzene with elimination of ethanol. Subsequent demethylation provided the hydroxybenzothiophene needed for subsequent ether formation.

Analogous cyclisation of phenylthioacetone derivatives with PPA can be used to synthesise 3-methyl derivatives of benzothiophene methyl ethers

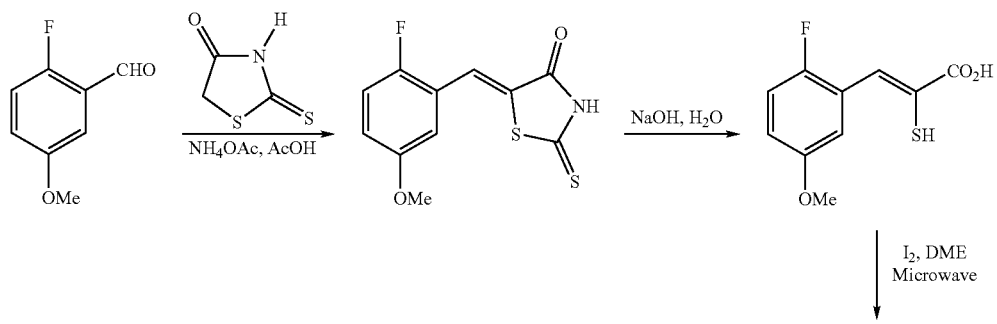

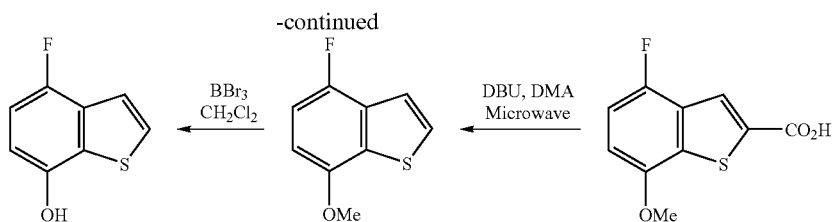

A further preferred route to substituted benzothiophenes is an iodine catalysed cyclisation of a mercaptopropenoic acid. Thus a benzaldehyde can be condensed with rhodanine and subsequently hydrolysed under basic conditions to a mercaptopropenoic acid. The resultant mercaptopropenoic acid can be cyclised using iodine and then decarboxylated with diazobicycloundecane in dimethylacetamide. Finally boron tribromide in dichloromethane may be used to demethylate the methyl ether to provide the hydroxybenzothiophene.

Where X is thienyl or phenyl the corresponding ethers can typically be prepared generally as follows (W and Y are as defined above).

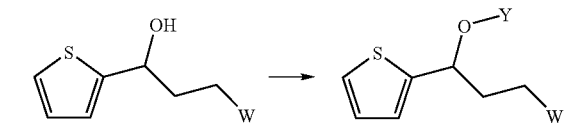

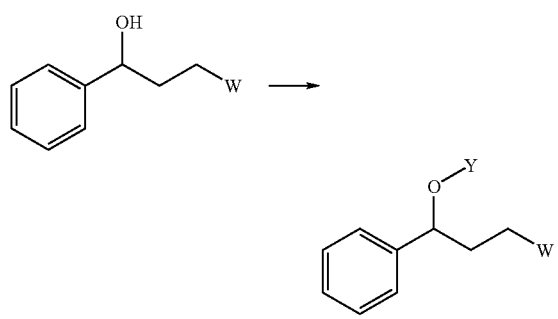

The chiral hydroxy intermediates can then be subjected to alkylation reactions. Various alkylation conditions can be used such as the Mitsunobu reaction, wherein roughly equal quantities of the heteroaryl alcohol phenol) and chloropropanol or iodopropanol are stirred at temperatures of between 0° C. and reflux in a polar non-protic solvent such as THF, with a complexing agent such as diethyl azodicarboxylate, or other derivative with a phosphine ligand such as triphenylphosphine. Alternatively 4,4-(dimethyl-1,1-dioxido-1,2,5-thiadiazolidin-2-yl)-triphenyl phosphonium in THF may be used in place of mixtures diethyl azodicarboxylate and triphenylphosphine. This type of reaction is well known and further combinations of the Mitsunobu reagents can be found in Organic Preparations and Procedures Int., 1996, 28, 2, 165 and references therein.

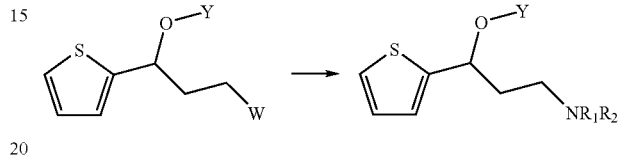

The corresponding ethers can be readily converted to the amines by heating in a sealed vessel with the appropriate alkyl amine in a lower alkyl alcohol solvent, at temperatures between 100° C. and 150° C. for between 1 and 6 hours. To aid handling of the resulting amines their organic acid salts can typically be prepared using equimolar quantities of the propanolamines with an organic acid such as oxalic and maleic acid. The reactants are generally combined in a mutual solvent such as ethyl acetate, and the salt normally precipitates out over time and can be isolated by filtration, or by removing the solvent in vacuo, re-dissolving in purified water and freeze drying to obtain the salt.

Compounds of formula I where $R_1$=methyl and $R_2$=H may be prepared by solid phase synthesis by the route shown below.

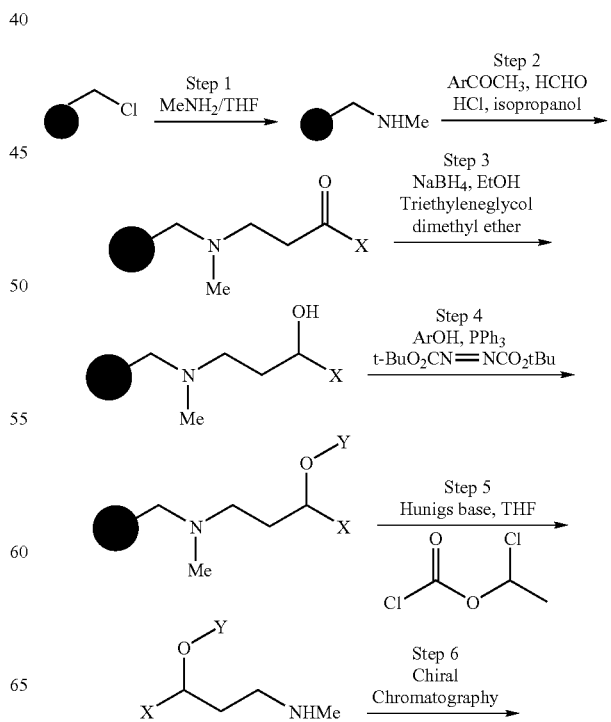

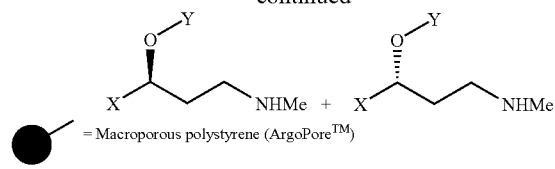

= Macroporous polystyrene (ArgoPore™)

The sequence is preferably performed on a macroporous polystyrene resin, e.g. Thus ArgoPore-Cl is converted with methylamine in methanol to a secondary amine bound to the resin. A Mannich type reaction is then performed on the resin bound amine with aqueous formaldehyde, hydrochloric acid a substituted acetophenone and isopropanol. The resultant aminoketone is then reduced with sodium borohydride in ethanol/triethyleneglycol dimethyl ether to give the amino alcohol. This is then subjected to a Mitsunobu reaction using di-t-butylazodicarboxylate, triphenyl phosphine and a heterocyclic phenol to give a resin bound heteroaryl aminoether. Removal of the aminoether from the resin is effected with 1-chloroethyl chloroformate and Hunigs base in THF. Finally resolution of the enantiomers is achieved using chiral chromatography.

The following Examples further illustrate the compounds of the present invention and methods for their synthesis.

In the following section, there is described the synthesis of precursors and common intermediates for the compounds of the present invention.

4-Fluoro-2-methoxybenzenethiol a) 2-Bromo-5-fluoroanisole

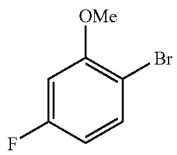

To a suspension of 2-bromo-5-fluorophenol (20.0 g, 104.7 mmol) and potassium carbonate (21.71 g, 157.1 mmol) in acetone (200 mL) was added dimethyl sulphate (10.90 mL, 115.2 mmol). The resulting suspension was allowed to stir at 60° C. for 2 h before being allowed to cool and then concentrated in vacuo. The residue was dissolved in ether (200 mL) and water (100 mL). The organic phase was washed with aqueous hydrochloric acid (2 N, 50 mL), saturated sodium bicarbonate solution (50 mL) with the resulting organic phase being dried (MgSO$_4$) and the solvent evaporated in vacuo to give a pale yellow oil (21.46 g, 100%). $\delta_H$ (300 MHz, CDCl$_3$) 7.45 (1H, dd, Ar), 6.70–6.55 (2H, m, Ar), 3.90 (3H, s, OCH$_3$).

b) 4-Fluoro-2-methoxybenzenethiol

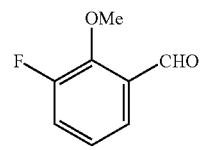

To a suspension of 2-bromo-5-fluoroanisole (2.00 g, 9.755 mmol) and elemental sulphur (0.468 g, 14.632 mmol) in dry THF (50 mL) was slowly added tert-butyl lithium in pentane (1.7 M, 12.6 mL, 21.46 mmol) at −78° C. The resulting suspension was allowed to stir at −78° C. for 60 mins before being poured onto saturated ammonium chloride solution (80 mL) and product extracted with diethyl ether (100 mL). The organic phase was washed with aqueous hydrochloric acid (2 N, 40 mL), with the resulting organic phase being dried (MgSO$_4$) and the solvent evaporated in vacuo to give a pale yellow oil. This was treated to a pad of silica gel, eluting with hexane:ethyl acetate [95:5] to give a pale yellow oil (1.50 g, 68%). $\delta_H$ (300 MHz, CDCl$_3$) 7.20 (1H, dd, Ar), 6.65–6.55 (2H, d, Ar), 3.90 (3H, s, OCH$_3$), 3.68 (1H, s, SH).

Similarly prepared was

3-Methoxy-5-trifluoromethylbenzenethiol as a pale yellow oil (14.473 g, 100%). $\delta_H$ (300 MHz, CDCl$_3$) 7.40–6.90 (3H, m, Ar), 3.87 (1H, s, SH), 3.80 (3H, s, OCH$_3$).

3-Fluoro-2-methoxybenzaldehyde

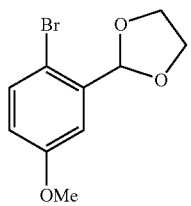

To a suspension of 3-fluoro-2-hydroxybenzaldehyde (5.328 g, 38.02 mmol) and potassium carbonate (7.88 g, 57.03 mmol) in acetone (60 mL) was added dimethyl sulphate (3.96 mL, 41.83 mmol). The resulting suspension was stirred at 60° C. for 2 h before being allowed to cool and then concentrated in vacuo. The residue was dissolved in dichloromethane (100 mL) and water (50 mL). The organic phase was washed with saturated sodium bicarbonate (50 mL) with the resulting organic phase being dried (MgSO$_4$) and the solvent evaporated in vacuo to give a pale yellow oil (6.262 g, 38.02 mmol, 100%). $\delta_H$ (300 MHz, CDCl$_3$) 10.40 (1H, s, CHO), 7.60 (1H, d, Ar), 7.30 (1H), m, Ar), 7.10 (1H, m, Ar), 4.10 (3H, s, OCH$_3$).

5-Methoxy-2-methylbenzaldehyde a) 4-Bromo-3-(1,3-dioxolan-2-yl)phenyl methyl ether A solution of 2-bromo-5-methoxybenzaldehyde (10.00 g, 46.5 mmol) in toluene (600 mL), ethanediol (3.88 mL, 69.8 mmol) and para-toluene sulphonic acid (50 mg) were heated under Dean-Stark conditions for 24 h. After this time the reaction was allowed to cool to room temperature before being washed with saturated aqueous sodium hydrogen carbonate (2×150 mL). The organic phase was dried (MgSO$_4$) and the solvent removed in vacuo to give a colourless oil (12.6 g, 100%); R$_f$=0.23 in hexane:ethyl acetate [10:1]; δ$_H$ (300 MHz, CDCl$_3$) 7.42 (1H, d, Ar), 7.25 (1H, d, Ar), 6.75 (1H, dd, Ar), 6.03 (1H, s, CHO), 4.20–4.01 (4H, m, 2×CH$_2$), 3.80 (3H, s, OCH$_3$).

b) 3-(1,3-Dioxolan-2-yl)-4-methylphenyl methyl ether

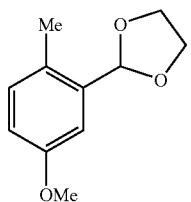

n-Butyl lithium in hexane (17.07 mL, 1.42 M, 25.1 mmol) was added dropwise at −78° C. to a stirred solution of 4-bromo-3-(1,3-dioxolan-2-yl)phenyl methyl ether (5.00 g, 19.3 mmol) in dry THF (60 mL). The resulting solution was allowed to stir at −78° C. for 30 mins before being quenched with iodomethane (2.40 mL, 38.6 mmol). The resulting solution was stirred at −78° C. for a further 20 mins before being quenched with saturated aqueous ammonium chloride solution (60 mL). The organic phase was dried (MgSO$_4$) and the solvent evaporated in vacuo. The residue was purified by flash chromatography eluting silica gel with hexane:ethyl acetate [10:1] to give a pale yellow oil (3.07 g, 82%); R$_f$=0.40 in hexane:ethyl acetate [10:1]; δ$_H$ (300 MHz, CDCl$_3$) 7.20–6.99 (2H, m, Ar), 6.75 (1H, dd, Ar), 5.92 (1H, s, CH), 4.20–4.01 (4H, m, 2×CH$_2$), 3.80 (3H, s, OCH$_3$), 2.32 (3H, s, CH$_3$).

c) 5-Methoxy-2-methylbenzaldehyde

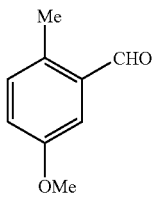

A solution of 2-(2-methyl-5-methoxyphenyl)-1,3-dioxalone (7.28 g, 37.5 mmol) in THF (1200 mL) and HCl (5%, 50 mL) was stirred at room temperature for 48 h. After this time the reaction was diluted with diethyl ether (100 mL) and washed with brine. The organic phase was dried (MgSO$_4$) and the solvent evaporated in vacuo. The residue was purified by flash chromatography eluting silica gel with hexane:ethyl acetate [95:5] to give a pale yellow oil (4.93 g, 88%); R$_f$=0.31 in hexane:ethyl acetate [10:1]; δ$_H$ (300 MHz, CDCl$_3$) 10.28 (1H, s, CHO), 7.35–6.99 (3H, m, Ar), 3.82 (3H, s, OCH$_3$), 2.62 (3H, s, CH$_3$).

1-[(5-Fluoro-2-methoxyphenyl)thio]acetone

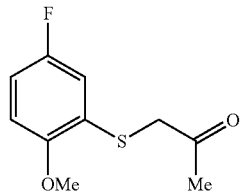

tert-Butyl lithium in pentane (6.30 mL, 10.7 mmol) was added dropwise at −78° C. over 35 mins to a stirred suspension of 2-bromo-4-fluoroanisole (1.00 g, 4.87 mmol) and elemental sulfur (234 mg, 7.31 mmol) in dry THF (10 mL). The resulting yellow solution was stirred and −78° C. for 15 mins before chloroacetone (894 mg, 9.74 mmol) was added. The resulting solution was allowed to stir at −78° C. for 1 hr before being quenched with NH$_4$Cl (sat., 20 mL). The organic phase was extracted and dried (MgSO$_4$) and the solvent removed in vacuo. The residue was purified by flash chromatography eluting silica gel with hexane:ethyl acetate [4:1] to yield a colourless oil (1.03 g, 98%) which slowly solidified on standing; R$_f$=0.34 in hexane:ethyl acetate [4:1]; δ$_H$ (300 MHz, CDCl$_3$) 7.08–6.98 (1H, dd, Ar), 6.95–6.82 (1H, m, Ar), 6.80–6.71 (1H, dd, Ar), 3.91 (3H, s, OCH$_3$), 3.75 (2H, s, CH$_2$), 2.30 (3H, s, CH$_3$).

1-[(2-Fluoro-5-methoxyphenyl)thio]acetone

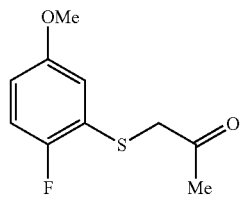

To a solution of 2,2,6,6-tetramethylpiperidine (8.03 mL, 47.6 mmol) in THF (20 mL) at −78° C. was added a solution of 2.5 M n-butyllithium in hexanes (19.04 mL, 47.6 mmol). After stirring for 30 minutes at −78° C. a solution of 4-fluoroanisole (5 g, 39.7 mmol) in THF (10 mL) was added dropwise. After a further 30 minutes elemental sulphur (1.78 g, 55.5 mmol) was added and stirred until almost all of the sulphur has disappeared. Chloroacetone (3.79 mL, 47.6 mmol) was then added and the solution warmed to room temperature over 2 hours. The reaction was quenched by pouring into saturated ammonium chloride (50 mL) and extraction with diethyl ether (2×50 mL). The combined organic extracts were dried (MgSO$_4$) and the solvent removed in vacuo to give a brown oil which was purified by flash chromatography with a gradient of 0–5% diethyl ether in hexane to give the title compound (1.96 g, 23%); δ$_H$ (300 MHz, CDCl$_3$) 7.02–6.86 (2H, m, ArH), 6.80–6.71 (1H, m, ArH), 3.78 (3H, s, OCH$_3$), 3.68 (2H, s, CH$_2$) and 2.29 (3H, s, CH$_3$).

(S)-(−)-3-Iodo-1-phenyl-1-propanol

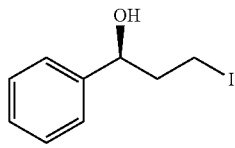

To a solution of (S)-(−)-3-chloro-1-phenyl-1-propanol (5 g, 29.3 mmol) in acetone (50 mL) was added sodium iodide (4.83 g, 32.2 mmol). The resulting solution was heated at reflux for 16 h. The solution was cooled, filtered and concentrated in vacuo. The residue was purified by flash chromatography eluting silica gel with hexane:ethyl acetate [100:0 to 3:1] to yield the iodo compound (7.44 g, 97%); $\delta_H$ (300 MHz, CDCl$_3$) 7.36 (5H, m, Ar), 4.83 (1H, m, O—CH), 3.34–3.15 (2H, m, CH$_2$), 2.28–2.15 (2H, m, CH$_2$).

(R)-(+)-3-Iodo-1-phenyl-1-propanol

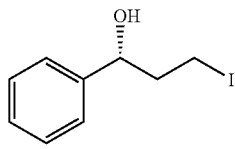

To a solution of (R)-(+)-3-chloro-1-phenyl-1-propanol (5 g, 29.3 mmol) in acetone (50 mL) was added sodium iodide (4.83 g, 32.2 mmol). The resulting solution was heated at reflux for 16 h. The solution was cooled, filtered and concentrated in vacuo. The residue was purified by flash chromatography eluting silica gel with hexane:ethyl acetate [100:0 to 3:1] to yield the title compound as a white solid (7.51 g, 98%); $\delta_H$ (300 MHz, CDCl$_3$) 7.36 (5H, m, Ar), 4.83 (1H, m, O—CH), 3.34–3.15 (2H, m, CH$_2$), 2.28–2.15 (2H, m, CH$_2$).

1-Benzothien-7-yl methyl ether
a) 1-[(2,2-Diethoxyethyl)thio]-2-methoxybenzene

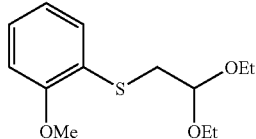

To a suspension of 2-methoxybenzenethiol (10 g, 71.4 mmol) and potassium carbonate (20 g, 143 mmol) in dry N,N-dimethylformamide (100 mL) was added dropwise over 20 mins a solution of bromoacetaldehyde diethyl acetal (10.3 mL, 71.4 mmol) in dry N,N-dimethylformamide (50 mL). The resulting suspension was allowed to stir at room temperature for 45 mins before being diluted with water (500 mL) and extracted with hexane (200 mL). The organic phase was further extracted with brine (4×100 mL), with the resulting organic phase being dried (MgSO$_4$) and the solvent removed in vacuo to give a pale yellow oil (18.6 g) which was ca 95% pure. This material was further purified by flash chromatography eluting silica gel with hexane:ether [10:1] to give a colourless oil (18 g, 98%). $\delta_H$ (300 MHz, CDCl$_3$) 7.34 (1H, d, Ar), 7.2 (1H, m, Ar), 6.92–6.80 (2H, m, Ar), 4.62 (1H, t, J=7 Hz, CH(OEt)$_2$), 3.85 (3H, s, OCH$_3$), 3.70–3.42 (4H, m, OCH$_2$CH$_3$), 3.10 (2H, d, J=7 Hz, SCH$_2$), 1.12 (6H, t, J=7 Hz, OCH$_2$CH$_3$).

Similarly prepared were

1-[(2,2-Diethoxyethyl)thio]-4-fluoro-2-methoxybenzene as a colourless oil (0.828 g, 3.018 mmol, 46%). $\delta_H$ (300 MHz, CDCl$_3$) 7.38 (1H, dd, Ar), 6.90 (2H, m, Ar), 4.62 (1H, t, J=7 Hz, CH(OEt)$_2$), 3.85 (3H, s, OCH$_3$), 3.70–3.45 (4H, m, OCH$_2$CH$_3$), 3.00 (2H, d, J=7 Hz, SCH$_2$), 1.18 (6H, t, J=7 Hz, OCH$_2$CH$_3$).

1-[(2,2-Diethoxyethyl)thio]-3-methoxy-5-trifluoromethylbenzene as a pale orange oil (6.87 g, 21.18 mmol, 34%). $\delta_H$ (300 MHz, CDCl$_3$) 7.20 (1H, s, Ar), 7.00 (1H, s, Ar), 6.90 (1H, s, Ar), 4.65 (1H, t, J=7 Hz, CH(OEt)$_2$), 3.80 (3H, s, OCH$_3$), 3.70–3.50 (4H, m, OCH$_2$CH$_3$), 3.15 (2H, d, J=7 Hz, SCH$_2$), 1.20 (6H, t, J=7 Hz, OCH$_2$CH$_3$).

b) 1-Benzothien-7-yl methyl ether

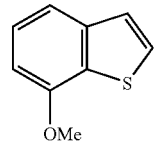

A solution of 1-[(2,2-diethoxyethyl)thio]-2-methoxybenzene (18 g, 70.3 mmol) in dry chlorobenzene (100 mL) was added slowly to a stirred solution of polyphosphoric acid (50 g) in dry chlorobenzene (300 mL) at 145° C. After addition was complete the resulting black solution was stirred at 155° C. for a further 18 hrs. After this time the reaction was allowed to cool to room temperature before being filtered through a pad of CELITE™, the solid cake was washed with dichloromethane (200 mL) and the combined organic extracts were concentrated in vacuo. The residue was purified by flash chromatography eluting silica gel with hexane:ethyl acetate [95:5] to give a pale yellow oil (8.7 g, 75%); $\delta_H$ (300 MHz, CDCl$_3$) 7.45–7.29 (4H, m, Ar), 6.75 (1H, d, Ar), 4.00 (3H, s, OCH$_3$).

Similarly prepared were

5-Fluoro-1-benzothien-7-yl methyl ether as a pale yellow oil (0.132 g, 0.724 mmol, 24%); $\delta_H$ (300 MHz, CDCl$_3$) 7.50 (1H, d, Ar), 7.28 (1H, d, Ar), 7.10 (1H, d, Ar), 6.58 (1H, d, Ar), 4.00 (3H, s, OCH$_3$).

4-Trifluoromethyl-1-benzothien-6-yl methyl ether as a yellow oil (2.832 g, 12.19 mmol, 58%); $\delta_H$ (300 MHz, CDCl$_3$) 7.50–7.35 (3H, m, Ar), 7.28 (1H, s, Ar), 3.90 (3H, s, OCH$_3$).

4-Fluoro-7-methoxy-1-benzothiophene a) 5-(2-Fluoro-5-methoxybenzylidene)-2-thioxo-1,3-thiazolidin-4-one

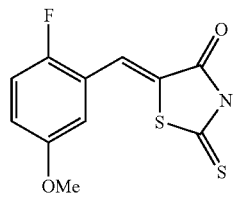

To a suspension of 2-fluoro-5-methoxybenzaldehyde (5.00 g, 32.46 mmol) and rhodanine (4.31 g, 32.46 mmol) in dry toluene (1000 mL) was added ammonium acetate (50 mg) and acetic acid (2 mL). The resulting suspension was allowed to stir at 120° C. for 12 h under Dean-Stark apparatus before being allowed to cool and filtered. Resultant solid was washed with hexane and allowed to dry in vacuo to give an orange crystalline solid (8.00 g, 91%); $\delta_H$ (300 MHz, CDCl$_3$) 7.50 (1H, s, CH=C); 7.31 (1H, t, Ar), 7.20–7.11 (1H, m, Ar), 6.95–6.89 (1H, m, Ar), 3.80 (3H, s, OCH$_3$).

Similarly prepared were 5-(3-Fluoro-2-methoxybenzylidene)-2-thioxo-1,3-thiazolidin-4-one as an orange solid (7.942 g, 78%). $\delta_H$ (300 MHz, CDCl$_3$) 7.82 (1H, s, ArCHCR$_2$), 7.30–7.10 (3H, m, Ar), 4.05 (3H, s, OCH$_3$).

5-(2-Methyl-5-methoxybenzylidene)-2-thioxo-1,3-thiazolidin-4-one as an orange crystalline solid (8.00 g, 91%); $\delta_H$ (300 MHz, CDCl$_3$) 7.80 (1H, s, Ar), 7.29–7.10 (1H, m, Ar), 6.95–6.84 (2H, m, Ar and CH=C), 3.83 (3H, s, OCH$_3$), 2.37 (3H, s, CH$_3$).

b) (2Z)-3-(2-Fluoro-5-methoxyphenyl)-2-mercapto-2-propenoic acid

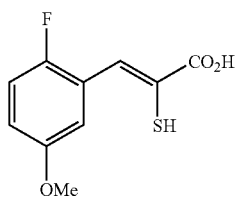

5-(2-Fluoro-5-methoxybenzylidene)-2-thioxo-1,3-thiazolidin-4-one (8.00 g, 9.7 mmol) was added in one portion to 25% w/v sodium hydroxide solution (40 mL). This was allowed stir at reflux for 1 h. After this time the reaction was allowed to cool to room temperature and poured onto water (50 mL). This was washed with dichloromethane (50 mL), and the aqueous layer acidified to pH 2 with aqueous hydrochloric acid (2 N, 50 mL) to give a white suspension. Product was extracted with ether (2×60 mL), dried (MgSO$_4$) and solvent removed in vacuo to give a white solid (6.71 g, 100%); $\delta_H$ (300 MHz, CD$_3$OD) 7.85 (1H, s, Ar), 7.46–7.35 (1H, m, Ar), 7.11 (1H, t, Ar), 7.01–6.75 (2H, m, CH=, and SH), 3.80 (3H, s, OCH$_3$).

Similarly prepared were (2Z)-3-(3-Fluoro-2-methoxyphenyl)-2-mercapto-2-propenoic acid as a solid (1.596 g, 94%); $\delta_H$ (300 MHz, CDCl$_3$) 8.12 (1H, s, ArCHCR$_2$), 7.60 (1H, d, Ar), 7.15–7.00 (2H, m, Ar), 4.55 (1H, s, SH), 3.98 (3H, s, OCH$_3$).

(2Z)-3-(2-Methyl-5-methoxyphenyl)-2-mercapto-2-propenoic acid as a white solid (6.71 g 100%); $\delta_H$ (300 MHz, CDCl$_3$) 8.00 (1H, s, CH=C), 7.30–7.09 (2H, m, Ar), 6.88–6.78 (1H, m, Ar), 3.80 (3H, s, OCH$_3$), 2.25 (3H, s, CH$_3$).

c) 4-Fluoro-7-methoxy-1-benzothiophene-2-carboxylic acid

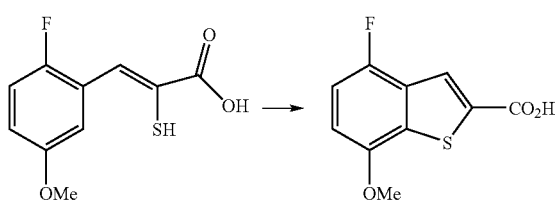

(2Z)-3-(2-Fluoro-5-methoxyphenyl)-2-mercapto-2-propenoic acid (1.00 g, 4.38 mmol) was added in one portion to a solution of iodine (1.66 g, 6.56 mmol) in dimethoxyethane (10 mL). This was heated in the microwave with 300 W at 160° C. for 10 mins. After this time the reaction was allowed to cool to room temperature and poured onto saturated sodium metabisulphite (200 mL) and ether (400 mL). Ether layer was separated and product extracted with aqueous sodium hydroxide (2 N, 2×100 mL). This was then acidified to pH 2 with aqueous hydrochloric acid (2 N, 250 mL), and product extracted with ether (2×150 mL). The combined organic extracts were dried (MgSO$_4$) and concentrated in vacuo to give a white solid (580 mg, 30%); $\delta_H$ (300 MHz, CD$_3$OD) 8.00 (1H, s, Ar), 7.30–7.19 (1H, m, Ar), 7.10–7.00 (1H, m, Ar), 3.95 (3H, s, OCH$_3$).

Similarly prepared was

4-Methyl-7-methoxy-1-benzothiophene-2-carboxylic acid as white solid (580 mg, 30%); $\delta_H$ (300 MHz, CDCl$_3$) 8.20 (1H, s, Ar), 7.12 (1H, d, Ar), 6.75 (1H, d, Ar), 3.99 (3H, s, OCH$_3$), 2.59 (3H, s, CH$_3$).

d) 4-Fluoro-7-methoxy-1-benzothiophene

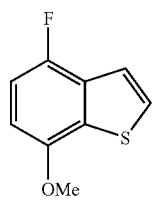

4-Fluoro-7-methoxy-1-benzothiophene-2-carboxylic acid (2.00 g, 8.84 mmol) was added in one portion to DBU (8 mL) and dimethyl acetamide (10 mL). This was heated in the microwave with 300 W at 200° C. for 1 h. The reaction mixture was allowed to cool and poured onto water (100 mL). Product was extracted with hexane (2×100 mL), washed with aqueous hydrochloric acid (2 N, 50 mL), aqueous sodium hydroxide (2 N, 50 mL), and the combined organic extracts were dried (MgSO$_4$) and concentrated in vacuo. The residue was purified by flash chromatography eluting silica gel with hexane:ethyl acetate [96:4] to give an oil (1.12 g, 70%); $\delta_H$ (300 MHz, CDCl$_3$) 7.4 (2H, s, Ar), 6.9 (1H, t, Ar), 6.60 (1H, dd, Ar), 3.91 (3H, s, OCH$_3$).

Similarly prepared was

4-Methyl-7-methoxy-1-benzothiophene as an oil (1.12 g, 70%); $\delta_H$ (300 MHz, CDCl$_3$) 7.46–7.32 (2H, m, Ar), 7.10 (1H, d, Ar), 6.66 (1H, d, Ar), 3.98 (3H, s, OCH$_3$), 2.52 (3H, s, CH$_3$).

5-Fluoro-4-methoxy-1-benzothiophene (2Z)-3-(3-Fluoro-2-methoxyphenyl)-2-mercapto-2-propenoic acid (4.865 g, 21.315 mmol) was added in one portion to a solution of iodine (8.255 g, 31.973 mmol) in dimethoxyetheane (30 mL). This was heated in the microwave with 300 W at 120° C. for 25 mins. After this time the reaction was allowed to cool to room temperature and poured onto saturated sodium metabisulphite (200 mL) and ether (400 mL). Ether layer was separated and product extracted with aqueous sodium hydroxide (2 N, 2×100 mL). This was then acidified to pH 2 with aqueous hydrochloric acid (2 N, 250 mL), and product extracted with ether (2×150 mL). The combined organic extracts were dried (MgSO$_4$) and concentrated in vacuo to give a tan coloured solid (3.240 g, 14.322 mmol, 67%). Which was used without further purification in the next step. 5-Fluoro-4-methoxy-1-benzothiophene-2-carboxylic acid (0.883 g, 3.903 mmol) was added in one portion to DBU (2.04 mL, 13.661 mmol) and dimethyl acetamide (10 mL). This was heated in the microwave with 300 W at 200° C. for 1 h. Reaction was allowed to cool and poured onto water (100 mL). Product was extracted with hexane (2×100 mL), washed with aqueous hydrochloric acid (2 N, 50 mL), aqueous sodium hydroxide (2 N, 50 mL), and the combined organic extracts were dried (MgSO$_4$) and concentrated in vacuo. The residue was purified by flash chromatography eluting silica gel with hexane:ethyl acetate [96:4] to give a pale yellow oil (0.167 g, 23%); $\delta_H$ (300 MHz, CDCl$_3$) 7.60–6.80 (4H, m, Ar), 4.10 (3H, s, OCH$_3$).

7-Fluoro-4-methoxy-1-benzothiophene a) 2-(5-Fluoro-2-methoxyphenyl)-2-hydroxy-N,N-dimethylethanethioamide

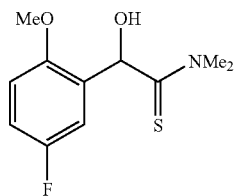

To a solution of lithium diisopropylamide, 2M in THF/n-heptane (210 mL, 583 mmol) was added THF (100 mL) and the solution cooled to −78° C. under nitrogen. This was then added dropwise over 1 h to a solution of the 5-fluoro-2-methoxybenzaldehyde (50 g, 0.32 mmol) and N,N-dimethylthioformamide (34.7 g, 389 mmol) in dry THF (200 mL). This was warmed to −5° C. and quenched with water (400 mL). The solution was filtered and washed with diethyl ether, the aqueous layer was extracted with ether (1 L). The combined organic layers were washed with water (500 mL), dried (MgSO$_4$) and the solvent removed in vacuo to give a crystalline suspension in oil. This was triturated in ether and filtered to give a crystalline solid (21.8 g, 28%); $\delta_H$ (300 MHz, CDCl$_3$) 7.16–6.81 (3H, m, ArH), 5.81–5.75 (1H, m, CHOH), 5.31–5.22 (1H, m, OH), 4.89 (3H, s, OCH$_3$), 3.50 (3H, s, N(CH$_3$)$_2$) and 3.08 (3H, s, N(CH$_3$)$_2$).

b) N-(7-Fluoro-4-methoxy-1-benzothien-2-yl)-N,N-dimethylamine

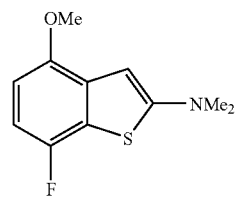

A solution of 2-(5-fluoro-2-methoxyphenyl)-2-hydroxy-N,N-dimethylethanethioamide (0.5 g, 2.1 mmol) in Eaton's reagent (5 mL) were combined and heated rapidly to 60° C. and left for 1 h. After cooling to room temperature over 2 hours the mixture was dropwise addition into prechilled aqueous sodium hydroxide (2 N, 16.25 mL) with constant stirring. This solution was then extracted with methyl tert-butyl ether (5×20 mL) and the combined organic extracts were dried (MgSO$_4$) and the solvent removed in vacuo to give a yellow solid. This was purified by flash chromatography with a gradient of 0–2% diethyl ether in hexane and gave 0.2 g of yellow solid containing an impurity, this was triturated with hexane to leave a colourless solid (0.155 g, 34%) of the title compound; $\delta_H$ (300 MHz, CDCl$_3$) 6.70–6.52 (2H, m, ArH), 6.12–6.10 (1H, m, ArH) 3.90 (3H, s, OCH$_3$) and 3.2 (6H, s, N(CH$_3$)$_2$), M+H=226.1.

c) 7-Fluoro-4-methoxy-1-benzothiophen-2(3H)-one

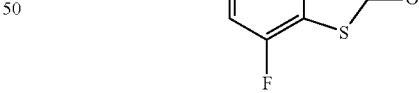

To a solution of N-(7-fluoro-4-methoxy-1-benzothien-2-yl)-N,N-dimethylamine (1.73 g, 7.7 mmol) in THF (25 mL) was added aqueous hydrochloric acid (1 N, 25 mL) and this was heated to 80° C. for 3 h. After cooling to room temperature then extracted with ether (100 mL), dried (MgSO$_4$) and the solvent evaporated in vacuo to give a yellow solid. The residue was purified by flash chromatography in 5% ethyl acetate in hexane to give (1.3 g, 84%) of the title compound; $\delta_H$ (300 MHz, CHCl$_3$) 6.97–6.87 (1H, m, ArH), 6.62–6.55 (1H, m, ArH), 3.91 (2H, s, CH$_2$) and 3.85 (3H, s, OCH$_3$).

d) 7-Fluoro-4-methoxy-1-benzothiophene

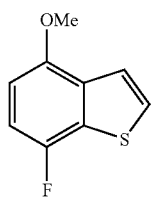

To a solution of 7-fluoro-4-methoxy-1-benzothiophen-2(3H)-one (1.06, 5.4 mmol) in dichloromethane (10 mL) at 0° C. was added slowly a solution of diisobutylaluminium hydride in dichloromethane (1 M, 8.04 mL, 8.0 mmol). After 30 mins the reaction was quenched by careful addition of aqueous hydrochloric acid (6 N, 25 mL). The mixture was concentrated to remove the dichloromethane, the aqueous residue was then stirred at 35° C. for 2 h. The aqueous solution was extracted with diethyl ether (3×50 mL), washed with aqueous sodium hydroxide (2 N, 50 mL), brine (50 mL) then dried (MgSO$_4$) and the solvent evaporated in vacuo to give the title compound (0.86 g, 87%) as a purple oil; $\delta_H$ 7.44–7.38 (1H, m, ArH), 7.36–7.24 (1H, m, ArH), 6.88–6.80 (1H, m, ArH), 6.57–6.49 (1H, m, ArH) and 3.82 (3H, s, OCH$_3$).

7-Fluoro-4-methoxy-1-benzothiophene
a) 2,3-Difluoro-6-methoxybenzaldehyde

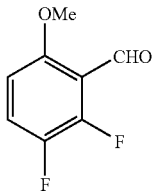

A solution of lithium diisopropylamide, 2M in THF/n-heptane (171 mL, 341 mmol) was further diluted with dry THF (250 mL) and cooled under nitrogen to −75° C. 3,4-Difluoroanisole (46.8 g, 325 mmol) in dry THF (100 mL) was added dropwise and the mixture stirred at −75° C. for 1 h. Dry N,N-dimethylformamide (27.6 mL, 358 mmol) was added dropwise and the mixture stirred for 10 mins at −70° C. Acetic acid (30 mL) and water (400 mL) were added, warming the temperature to 10° C. Extracted into diethyl ether (2×300 mL). Combined extracts were washed with water (250 mL), aqueous hydrochloric acid (0.2 N, 400 mL) and brine (2×250 mL), dried (MgSO$_4$) and the solvent evaporated in vacuo to give a red/orange oil which crystallised. Purification was by recrystallisation from diethyl ether/petroleum ether 40–60 to give (53.0 g, 95%) of solid; $\delta_H$ (300 MHz, CDCl$_3$) 10.40 (1H, s, CHO), 7.37 (1H, q, ArH), 6.71 (1H, m, ArH), and 3.93 (3H, s OCH$_3$).

b) Methyl 7-fluoro-4-methoxy-1-benzothiophene-2-carboxylate

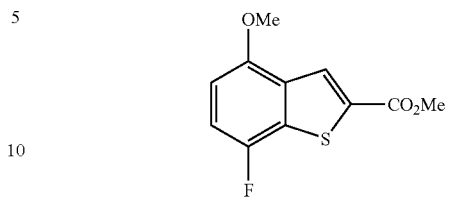

Methyl thioglycolate (28.8 mL, 320 mmol) was added under nitrogen to a solution of triethylamine (86.6 mL) in dry N,N-dimethylformamide (220 mL) at 80° C. Stirred at 100° C. for 15 mins. A solution of 2,3-difluoro-6-methoxybenzaldehyde (55.1 g, 320 mmol) in N,N-dimethylformamide (80 mL) was added and the mixture heated at 130° C. for 3 h. Allowed to cool then poured onto ice-water (2 L). The resulting yellow solid was filtered, washing with water (2×200 mL). Dried under vacuum over phosphorus pentoxide at room temperature overnight to give the title compound (67.2 g, 87%); $\delta_H$ (300 MHz, CDCl$_3$) 8.20 (1H, d, ArH), 7.06 (1H, t, ArH), 6.68 (1H, m, ArH) and 3.99 (6H, s, OCH$_3$ and CO$_2$CH$_3$).

c) 7-Fluoro-4-methoxy-1-benzothiophene-2-carboxylic acid

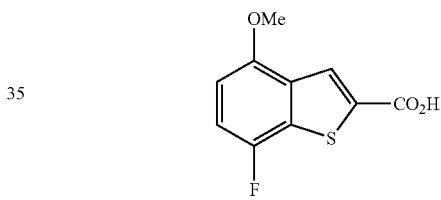

A mixture of methyl 7-fluoro-4-methoxy-1-benzothiophene-2-carboxylate (67.2 g, 280 mmol), sodium hydroxide (45 g, 1.12 mol), methanol (800 mL) and water (400 mL) were stirred at ambient overnight. The methanol was evaporated and the mixture cooled to 0° C. Acidified with concentrated hydrochloric acid and stirred for 20 mins. The yellow solid was filtered, washing with water (3×100 mL). Dried under vacuum at 45° C. overnight, over phosphorus pentoxide to give the title compound (61.4 g, 97%); $\delta_H$ (300 MHz, d$_6$-DMSO) 8.10 (1H, d, ArH) 7.44 (1H, t, ArH) 7.00 (1H, m, ArH) and 4.02 (3H, s, OCH$_3$).

d) 7-Fluoro-4-methoxy-1-benzothiophene

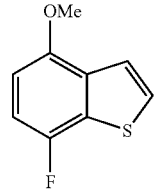

A mixture of 7-fluoro-4-methoxy-1-benzothiophene-2-carboxylic acid (61.4 g, 271 mmol) and copper powder (22.4 g, 352 mmol) in quinoline (500 mL) was heated at 190° C.

for 1 h. Cooled to ambient and poured onto aqueous hydrochloric acid (2 N, 750 mL). Stirred with ethyl acetate (500 mL) for 15 minutes. Filtered through Celite, washing with ethyl acetate. The aqueous layer was extracted into ethyl acetate and the combined organic layers were washed with aqueous hydrochloric acid (2 N, 500 mL), water (500 mL), brine (500 mL), dried over MgSO$_4$ and evaporated in vacuo. Purified by column chromatography, eluting silica gel with iso-hexane/diethyl ether 0–5% to give the product as a brown oil which crystallised to give the title compound (41.3 g, 84%); δ$_H$ (300 MHz, CDCl$_3$) 7.51 (1H, m, ArH), 7.38 (1H, d, ArH), 6.98 (1H, t, ArH), 6.65 (1H, dd, ArH) and 3.92 (3H, s, OCH$_3$).

3-Chloro-4-fluoro-7-methoxy-1-benzothiophene a) (2E)-3-(2-Fluoro-5-methoxyphenyl)-2-propenoic acid

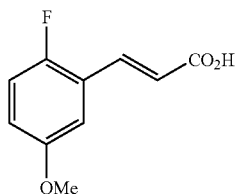

A solution of 2-fluoro-5-methoxybenzaldehyde (10.00 g, 64.9 mmol), malonic acid (13.4 g, 128.8 mmol), piperidine (2.00 mL) and pyridine (100 mL) was heated to 110° C. for 2 h. After this time the solvent was removed in vacuo and the residue taken up in ethyl acetate and washed with aqueous hydrochloric acid (2N, 100 mL). The organic solvent was dried (MgSO$_4$) and the solvent evaporated in vacuo. The solid was recrystallised from hot etahanol to give a white solid (12.2 g, 95%); δ$_H$ (300 MHz, DMSO) 7.60 (1H, d, J 7 Hz, CH=C), 7.31–7.28 (1H, m, Ar), 7.20 (1H, t, Ar), 7.07–6.97 (1H, m, Ar), 6.62 (1H, d, J 8 Hz, CH=CH), 3.80 (3H, s, OCH$_3$).

b) Methyl 3-chloro-4-fluoro-7-methoxy-1-benzothiophene-2-carboxylate

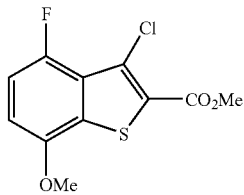

Thionyl chloride (3.7 mL, 50.8 mL) was added to a stirred solution of (2E)-3-(2-fluoro-5-methoxyphenyl)-2-propenoic acid (2.5 g, 12.7 mmol) and pyridine (100 μl). The resulting yellow suspension was stirred at 120° C. for 2 h before being allowed to cool to room temperature. The mixture was diluted with dichloromethane (50 mL) and concentrated in vacuo. The resulting yellow solid was taken up in methanol (100 mL) and heated to 70° C. for 1 hr. After this time the solvent was removed in vacuo to leave a white solid (984 mg, 28%); δ$_H$ (300 MHz, CDCl$_3$) 7.09–6.98 (1H, m, Ar), 6.80–6.71 (1H, dd, Ar), 3.98 (6H, s, OCH$_3$ and CO$_2$CH$_3$).

c) 3-Chloro-4-fluoro-7-methoxy-1-benzothiophene-2-carboxylic acid.

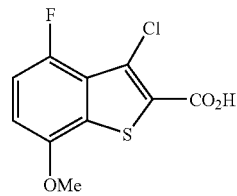

Methyl 3-chloro-4-fluoro-7-methoxy-1-benzothiophene-2-carboxylate (2.00 g, 7.29 mmol) was suspended in THF:H$_2$O [10:1] and lithium hydroxide (260 mg) added, the resulting suspension was heated to 40° C. for 1 h. After cooling to room temperature the mixture was extracted with diethyl ether (50 mL) and the aqueous phase acidified to pH 2 and the solid collected by filtration and vacuum dried to give a white solid (1.09 g, 58%); δ$_H$ (300 MHz, DMSO) 7.32–7.20 (1H, m, Ar), 7.15–7.05 (1H, dd, Ar), 3.98 (3H, s, OCH$_3$).

d) 3-Chloro-4-fluoro-7-methoxy-1-benzothiophene.

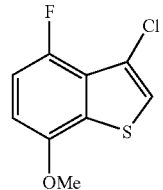

A mixture of 3-chloro-4-fluoro-7-methoxy-1-benzothiophene-2-carboxylic acid (1.09 g, 4.19 mmol) and diazobicycloundecane (DBU) (2 mL) in dimethylacetamide (15 mL) was heated in a sealed vessel in a microwave (300 W, 100%) for 1 h. After cooling to room temperature the mixture was diluted with diethyl ether (100 mL) and washed with brine (2×100 mL). The organic phase was dried (MgSO$_4$) and the solvent removed in vacuo. The residue was purified by flash chromatography eluting silica gel with hexane:diethyl ether [10:1] to yield a white solid (520 mg, 57%); δ$_H$ (300 MHz, CDCl$_3$) 7.24 (1H, s, Ar), 7.05–6.92 (1H, m, Ar), 6.70–6.60 (1H, dd, Ar), 3.96 (3H, s, OCH$_3$).

4-Fluoro-7-methoxy-3-methyl-1-benzothiophene

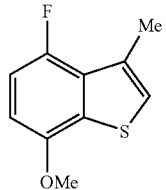

1-[(5-fluoro-2-methoxyphenyl)thio]acetone (1.00 g, 4.67 mmol) was added to a stirred solution of polyphosphoric acid (2.00 g) and chlorobenzene (70 mL). The resulting solution was stirred rapidly at 160° C. for 18 h. After this time the solution was allowed to cool to room temperature and washed with water (50 mL). The aqueous phase was extracted with dichloromethane (3×30 mL) and the combined organic extracts dried (MgSO₄). The solvent was removed in vacuo and the residue purified by flash chromatography eluting silica gel with hexane:ethyl acetate [10:1] to give a pale yellow oil (700 mg, 76%); $R_f$=0.72 in hexane:ether [10:1]; $δ_H$ (300 MHz, CDCl₃) 7.44–7.20 (1H, m, Ar), 6.99–6.82 (1H, m, Ar), 6.62–6.55 (1H, dd, Ar), 3.95 (3H, s, OCH₃), 2.56 (3H, s, CH₃).

Similarly prepared was

7-Fluoro-4-methoxy-3-methyl-benzothiophene as an oil (1.43 g, 91%); $δ_H$ (300 MHz, CDCl₃) 7.22 (1H, s, ArH), 6.89–6.81 (1H, m, ArH), 6.59–6.52 (1H, m, ArH), 3.81 (3H, s, OCH₃) and 2.56 (3H, s, CH₃).

2-Fluoro-7-methoxy-1-benzothiophene

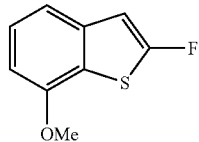

A solution of 1-benzothien-7-yl methyl ether (230 mg, 1.40 mmol) in dry THF (5 mL) was added dropwise to a freshly prepared solution of 2,2,6,6 tetramethyl-lithio-piperidine (1.68 mmol) in THF (10 mL) at −78° C. The resulting solution was stirred at this temperature for 30 mins before perchloryl fluoride gas was condensed into the reaction. After the strong exotherm had stopped the mixture was allowed to stir at −78° C. for a further 30 mins. After this time the reaction was quenched with NH₄Cl (sat, 20 mL) and diluted with diethyl ether. The organic phase was dried (MgSO₄) and the solvent removed in vacuo. The residue was purified by flash chromatography eluting silica gel with hexane to yield a colourless oil (128 mg, 50%); $δ_H$ (300 MHz, CDCl₃) 7.32–7.20 (2H, m, Ar), 6.80–6.62 (2H, m, Ar), 3.95 (3H, s, OCH₃).

Similarly prepared was

2-Fluoro-4-methoxy-1-benzothiophene as a colourless oil (420 mg, 48%); $δ_H$ (300 MHz, CDCl₃) 7.32–7.20 (2H, m, Ar), 6.80–6.62 (2H, m, Ar), 3.95 (3H, s, OCH₃).

7-Methoxy-1-benzothiophene-2-carbonitrile

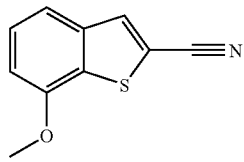

To a solution of 1-benzothien-7-yl methyl ether (1 g, 6.1 mmol) in THF (12 mL) at −78° C. was added a solution of 2.5 M n-butyllithium in hexanes (2.9 mL, 7.3 mmol). After stirring for 1.5 hr this solution was added dropwise to a solution of tosyl cyanide (1.66 g, 9.1 mmol) in THF (8 mL), this was left stirring at −78° C. for 0.5 hr and then warmed to room temperature. After 16 h this was poured onto ice-water and extracted with dichloromethane (3×50 mL). The combined organic extracts were washed with water, dried (MgSO₄) and the solvent removed in vacuo to give an oil. This was purified by flash chromatography with a gradient of 0–30% ethyl acetate in hexane to give the title compound (0.31 g, 27%); $δ_H$ (300 MHz, CDCl₃) 7.79 (1H, s, 3-ArH), 7.46–7.38 (1H, m, 4-ArH), 7.37–7.31 (1H, m, 5-ArH), 6.88–6.82 (1H, m, 6-ArH) and 3.94 (3H, s, OCH₃). Starting material 1-benzothien-7-yl methyl ether was recovered from the reaction (0.56 g, 56%); $δ_H$ (300 MHz, CDCl₃) 7.45–7.29 (4H, m, ArH), 6.75 (1H, m, ArH), 4.00 (3H, s, OCH₃).

7-Methoxy-1-benzothiophene-2-carbonitrile a) 2-Iodo-7-methoxy-1-benzothiophene

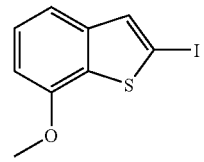

In a 4 L mechanically stirred reactor, a solution of 1-benzothien-7-yl methyl ether (105 g, 0.64 mol) in anhydrous THF (2 L) is cooled down to −74° C. n-Butyl lithium in hexane is added (2.5 N, 285 mL, 0.71 mol) within 45 min, keeping temperature below −70° C. The mixture is stirred 30 min at −78° C. and a solution of iodine (179 g, 0.70 mol) in anhydrous THF (1 L) is added within 1 h, keeping temperature below −70° C. After addition, the mixture is allowed to come up to room temperature over 2 h and brine (500 mL) is added. The layers are roughly separated and the organic layer is partially evaporated. Additional brine (200 mL) is added to the residual aqueous layer (mixed with some THF). After decantation, the organic and aqueous layers are separated. The aqueous layer is extracted with ethyl acetate (500 mL). The organic layers are pooled, washed with aqueous sodium thiosulphate, dried (MgSO₄) and the solvent evaporated in vacuo to give the crude iodo derivative (173.6 g, 93%) The solid is recrystallized from isopropanol (150 mL) to give pure compound (145.5 g, 88%); $δ_H$ (600 MHz, CDCl₃) 7.51 (s, 1H), 7.32 (d(br), J=7.89 Hz, 1H), 7.26 (t, J=7.89 Hz, 1H), 6.72 (d(br), J=7.89 Hz, 1H), 3.97 (s, 3H).

b) 7-Methoxy-1-benzothiophene-2-carbonitrile

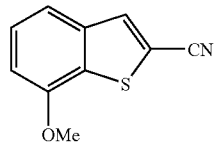

A solution of 2-iodo-7-methoxy-1-benzothiophene (10.0 g, 0.35 mol), copper (1) cyanide (6.17 g, 0.68 mol) and anhydrous N,N-dimethylformamide (40 mL) are warmed to 130° C. After 2.5 h at 130° C. no starting material is detectable as measured by HPLC at 220 nm. The reaction is cooled to 40° C. and a solution 25% v/v ethylenediamine in water (30 mL) and toluene (20 mL) are added. The mixture is stirred to room temperature. Additional toluene (30 mL) is added and the heterogeneous mixture is filtered. The layers of the mother liquors are separated and the aqueous layer is extracted with toluene (3×50 mL). The combined organic extracts were washed with water (2×50 mL), dried (MgSO$_4$) and the solvent evaporated in vacuo to give the title compound (5.78 g, 88%), which was used without further purification; δ$_H$ (300 MHz, CDCl$_3$) 7.79 (1H, s, 3-ArH), 7.46–7.38 (1H, m, 4-ArH), 7.37–7.31 (1H, m, 5-ArH), 6.88–6.82 (1H, m, 6-ArH) and 3.94 (3H, s, OCH$_3$).

4-Methoxy-1-benzothiophene-2-carbonitrile

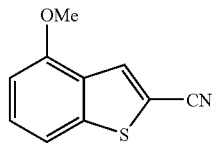

(Ref: Cheutin et al.; C. R. Hebd. Seances Acad. Sci; 261; 1965; 705.) A solution of 4-methoxy-1-benzothiophene-2-carboxylic acid (1.19 g, 5.7 mmol) in pyidine (25 mL) at 0° C. was treated with methanesulfonyl chloride (0.49 mL, 6.3 mmol) keeping the temperature at 0° C., stirring was continued for 2 h. Ammonia gas was then bubbled through the mixture for 5 minutes, followed by nitrogen for 10 mins. The reaction mixture was then treated with a large excess of mesyl chloride (4.43 mL, 57 mmol) and stirred for 16 h at room temperature. The solvent evaporated in vacuo to give a brown residue which was purified by flash chromatography with 10% ethyl acetate in hexane to give a colourless solid (800 mg, 74%); δ$_H$ (300 MHz, CDCl$_3$) 8.00 (1H, s, 3-ArH), 7.48–7.35 (2H, m, ArH), 6.80–6.77 (1H, m, ArH) and 3.92 (3H, s, OCH$_3$).

4-Fluoro-7-methoxy-1-benzothiophene-2-carbonitrile a) 4-Fluoro-7-methoxy-1-benzothiophene-2-carboxamide

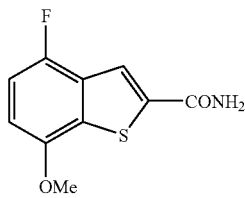

A solution of 4-fluoro-7-methoxy-1-benzothiophene-2-carboxylic acid (1.5 g, 6.6 mmol) in thionyl chloride (4 mL) was heated to 50° C. for 30 minutes, then the solvent removed in vacuo. The residue was taken up in dichloromethane (60 mL) and methanol (0.5 mL) and then added to a solution of concentrated ammonium hydroxide (40 mL) and dichloromethane (40 mL) at 5° C. After 10 min the solution was warmed to room temperature and stirred for 2 h. The dichloromethane was evaporated in vacuo and the solid filtered to give a pale browm solid (0.75 g, 51%); δ$_H$ (300 MHz, D$_4$-Methanol) 7.95 (1H, s, 3-ArH), 7.02–6.92 (1H, m, ArH), 6.83–6.77 (1H, m, ArH), 3.89 (3H, s, OCH$_3$) and 3.23–3.28 (2H, m, CONH$_2$).

b) 4-Fluoro-7-methoxy-1-benzothiophene-2-carbonitrile

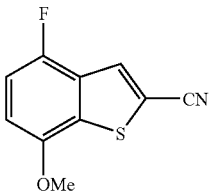

A solution of 4-fluoro-7-methoxy-1-benzothiophene-2-carboxamide (0.756 g, 3.3 mmol) in phosphorus oxychloride (6.2 mL, 6.6 mmol) was refluxed for 3 h then cooled and the solvent evaporated in vacuo to give the title compound. Purified by flash chromatography with a gradient of 0–30% ethyl acetate in iso-hexane to give a colourless solid (0.635 g, 91%); δ$_H$ (300 MHz, CDCl$_3$) 7.95 (1H, s, 3-ArH), 7.10–7.01 (1H, m, ArH), 6.85–6.77 (1H, m, ArH) and 3.98 (3H, s, OCH$_3$).

4-Cyano-7-methoxy benzo[b]thiophene.

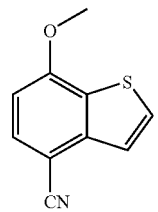

To a stirred solution of 4-bromo-7-methoxy benzo[b]thiophene (1.05 g, 4.32 mmol, 1 equiv.) in dry DMF (40 mL) was added copper(I)cyanide (3.885 g, 43.4 mmol, 10 equiv.) and the reaction mixture was heated at 150° C. overnight. The reaction mixture was cooled to ~120° C. and then solid iron(III)chloride (1.58 g, 9.74 mmol) was added followed by 1 N HCl (CAUTION: HCN evolution—perform in a well vented hood!) The reaction mixture was heated at ~100° C. for 2 hr before cooling to room temperature. Water, brine, and ethyl acetate were added and the layers were separated. The organic layer was washed with brine (3 times), dried over anhydrous magnesium sulfate, filtered, and concentrated under reduced pressure. The crude residue thus obtained was purified via medium pressure liquid chromatography eluting with 10% ethyl acetate/90% hexanes to afford the title compound (564 mg, 69%) as a colorless solid; □$_H$ (400 MHz, CDCl$_3$) 4.06 (3H, s), 6.81 (1H, d, J=8 Hz), 7.56 (1H, d, J=6 Hz), 7.65 (1H, d, J=6 Hz), 7.71 (1H, d, J=8 Hz).

Ref: (J. Chem. Soc. Perkin Trans 1 1983, 2973).

6-Methoxy-1-benzothiophene-2-carbonitrile a) O-(2-Formyl-5-methoxyphenyl) dimethylthiocarbamate

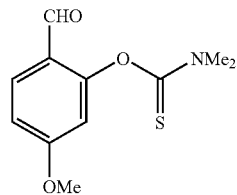

A solution of N,N-dimethylcarbamoyl chloride (4.46 g, 35.7 mmol) in THF (20 mL) was added over 15 minutes to a stirred cooled (0° C.), solution of 2-hydroxy-4-methoxybenzaldehyde (5 g, 32.9 mmol) and potassium hydroxide (2 g, 35.7 mmol) in water (25 mL) such that the temperature did not rise above 10° C. The mixture was stirred for 10 minutes at room temperature then extracted with ethyl acetate (3×50 mL), the combined organic layers were washed successively with 2M sodium hydroxide (100 mL), 2N hydrochloric acid (100 mL), brine (100 mL) then dried (MgSO$_4$) and the solvent removed in vacuo to give a yellow solid (6.8 g, 86%) which was used without further purification; δ$_H$ (300 MHz, CDCl$_3$) 7.88–7.80 (1H, m, ArH), 7.95–7.85 (1H, m, ArH), 6.65–6.60 (1H, m, ArH), 3.88 (3H, s, OCH$_3$), 3.46 (3H, s, N(CH$_3$)$_2$) and 3.40 (3H, s, N(CH$_3$)$_2$).

b) S-(2-Formyl-5-methoxyphenyl) dimethylthiocarbamate

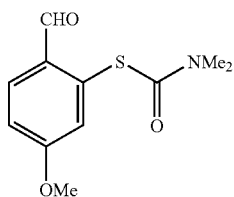

A pre-warmed solution of O-(2-formyl-5-methoxyphenyl) dimethylthiocarbamate (2 g, 8.3 mmol) in diphenyl ether (4 mL) was added to diphenyl ether (36 mL) at 230° C. The mixture was heated at 230° C. for 1.5 h. The reaction mixture was loaded neat onto flash chromatography column and solvent eluted with iso-hexane. Product eluted with a gradient of 0–30% ethyl acetate in iso-hexane. Further purified by flash chromatography with a gradient of 0–20% ethyl acetate in dichloromethane, followed by triturating with iso-hexane gave a solid which was recrystallised from ethyl acetate hexane to give the title compound (1.21 g, 61%); δ$_H$ (300 MHz, CDCl$_3$) 8.04–7.95 (1H, m, ArH), 7.09–6.99 (2H, m, ArH), 3.89 (3H, s, OCH$_3$), 3.16 (3H, br. s, N(CH$_3$)$_2$) and 3.02 (3H, br, s, N(CH$_3$)$_2$).

c) 6-Methoxy-1-benzothiophene-2-carbonitrile

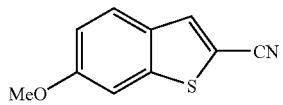

(Ref: Gallagher, T; Pardoe, D. A.; Porter, R.; Tetrahedron Lett.; 2000, 41(28), 5415–5418.) To a solution of S-(2-formyl-5-methoxyphenyl) dimethylthiocarbamate (1.08 g, 4.5 mmol) in water (4 mL) and methanol (8 mL) was added sodium hydroxide (199 mg, 4.9 mmol), this was heated to reflux for 16 hours. The reaction was cooled to room temperature and chloroacetonitrile (0.28 mL, 4.5 mmol) was added in one portion and the mixture the stirred at room temperature for 1 hour. The methanol was removed in vacuo, and water (10 mL) added. The aqueous layer was extracted with diethyl ether (3×20 mL), dried (MgSO$_4$) and the solvent removed in vacuo. The residue was purified by flash chromatography with a gradient of 0–30% ethyl acetate in iso-hexane to give the title compound as a colourless solid (390 mg, 46%); δ$_H$ (300 MHz, CDCl$_3$) 7.80–7.70 (1H, m, ArH), 7.29 (2H, m, ArH), 7.11–7.01 (1H, m, ArH) and 3.85 (3H, s, OCH$_3$). M+23=212.0. ν$_{max}$/cm$^{-1}$ [film] 2213.50 (m).

1-Benzothiophen-4-ol a) 5-Bromo-6,7-dihydro-1-benothiophen-4(5H)-one

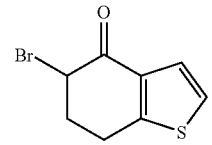

Ref: J. Chem. Res. (S) 1993, 192–193. Bromine (6.4 g, 40 mmol) in dry carbon tetrachloride containing a few drops of diethyl ether (20 mL) was added dropwise to a well stirred solution 6,7-dihydro-1-benothiophen-4(5H)-one (6.08 g; 40 mmol) in dry diethyl ether (250 mL) allowing the solution to decolourise between additions and the temperature maintained at −10° C. Once the addition was complete, the solution was allowed to warm slowly to room temperature. Water (200 mL) was slowly added and the mixture transferred to a separating funnel with ether (100 mL). The organic phase was washed with water (100 mL), dried over magnesium sulfate and evaporated to an oil which solidified on standing (8.56 g, 88%), this material was used without further purifictaion. δ$_H$ (300 MHz, CD$_3$OD) 7.36 (1H, d, Ar) 7.30 (1H, d, Ar), 4.63 (1H, t, CH) 3.20 (2H, m, CH$_2$), 2.56 (2H, m, CH$_2$).

b) 1-Benzothiophen-4-ol

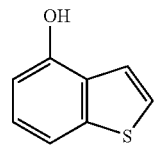

5-Bromo-6,7-dihydro-1-benothiophen-4(5H)-one (11.4 g, 50 mmol), lithium bromide (10 g) and lithium carbonate (7.4 g) were refluxed for 3 h in dry N,N-dimethylformamide (250 mL) under nitrogen. The solvent was evaporated in vacuo and the residue treated with cold aqueous hydrochloric acid (1 N, 250 mL). Extracted into diethyl ether (3×200 mL). The ethereal layer was extracted with 10% aqueous sodium hydroxide solution (2×). Combined aqueous layers were acidified and extracted into ether. Dried over magnesium sulfate and evaporated to an oil. Purified by chromatography eluting silica gel with ethyl acetate—hexane (4–6%). Combined fractions were evaporated to a light yellow oil which crystallised on standing, this material was triturated with cyclohexane to give white plates (3.6 g; 51%). δ$_H$ (300 MHz, CD$_3$OD) 7.45 (1H, d, Ar), 7.30–7.40 (2H, m, Ar), 7.12 (1H, m, Ar), 6.70 (1H, m, Ar).

Boron Tribromide Demethylation: General Procedure

1-Benzothiophen-7-ol

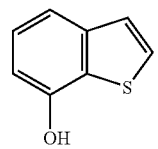

A solution of boron tribromide (115 μl, 1.21 mmol) was added dropwise at room temperature to a stirred solution of 1-benzothiophen-7-ol (200 mg, 1.21 mmol) in dry dichloromethane (10 mL). The resulting solution was allowed to stir at room temperature for a further 1 hr, after which the solvent was removed in vacuo and the residue taken up in ethyl acetate (20 mL) and extracted with aqueous hydrochloric acid (2 N, 10 mL). The organic phase was dried (MgSO$_4$) and the solvent was removed in vacuo. The resulting dark yellow oil was purified by flash chromatography eluting silica gel with hexane:ethyl acetate [4:1] to yield a white solid (68 mg, 38%); $\delta_H$ (300 MHz, CDCl$_3$) 7.50–7.39 (2H, m, Ar), 7.29–7.21 (1H, m, Ar), 7.21–7.15 (1H, m, Ar), 6.70 (1H, d, Ar), 5.15 (1H, bs, OH).

Similarly prepared were

5-Fluoro-1-benzothiopbene-7-ol as a brown crystalline solid (393 mg, 42%); $\delta_H$ (300 MHz, CDCl$_3$) 7.50 (1H, d, Ar), 7.28 (1H, d, Ar), 7.10 (1H, dd, Ar), 6.58 (1H, dd, Ar), 5.40 (1H, s, OH).

4-Trifluoromethyl-1-benzothiophen-6-ol as a brown crystalline solid (1.576 g, 62%); $\delta_H$ (300 MHz, CDCl$_3$) 7.50–7.40 (3H, m, Ar), 7.22 (1H, d, Ar), 5.30 (1H, bs, OH).

5-Fluoro-1-benzothiophen-4-ol as a white crystalline solid (0.074 g, 21%); $\delta_H$ (300 MHz, CDCl$_3$) 7.50 (1H, d, Ar), 7.42 (1H, d, Ar), 7.35 (1H, m, Ar), 7.10 (1H, t, Ar), 5.40 (1H, bs, OH).

4-Methyl-1-benzothiophen-7-ol as an oil (290 mg, 79%); $\delta_H$ (300 MHz, CDCl$_3$) 7.44 (1H, d, Ar), 7.32 (1H, d, Ar), 7.00 (1H, d, Ar), 6.61 (1H, d, Ar), 4.92 (1H, s, OH), 2.52 (3H, s, CH$_3$).

7-Fluoro-1-benzothiophen-4-ol as a solid (0.68 g, 79%); $\delta_H$ 7.45 (1H, m, ArH), 7.40 (1H, d, ArH), 6.90 (1H, t, ArH) and 6.74 (1H, m, ArH) and 5.00 (1H, br. s, OH).

3-Chloro-4-fluoro-1-benzothiophen-7-ol as a white solid (145 mg, 97%); $\delta_H$ (300 MHz, CDCl$_3$) 7.25 (1H, s, Ar), 7.05–6.85 (1H, m, Ar), 6.72–6.61 (1H, dd, Ar).

3-Methyl-4-fluoro-1-benzothiophen-7-ol as a white solid (447 mg, 69%); $\delta_H$ (300 MHz, CDCl$_3$) 7.28 (1H, s, Ar), 6.99 (1H, s, OR), 6.90–6.78 (1H, m, Ar), 6.60 (1H, dd, Ar), 2.57 (3H, s, CH$_3$).

7-Fluoro-3-methyl-1-benzothiophen-4-ol as a solid (0.77 g, 70%); $\delta_H$ (300 MHz, CDCl$_3$) 7.26 (1H, s, ArH), 6.85–6.77 (1H, m, ArH), 6.58–6.50 (1H, m, ArH), 4.98 (1H, s, OH) and 2.65 (3H, s, CH$_3$).

2-Fluoro-1-benzothiophen-7-ol as a colourless oil (502 mg, 50%); $\delta_H$ (300 MHz, CDCl$_3$) 7.35–7.12 (3H, m, Ar), 6.72–6.63 (1H, dd, Ar).

2-Fluoro-1-benzothiophen-4-ol as a colourless oil (213 mg, 55%); $\delta_H$ (300 MHz, CDCl$_3$) 7.44 (1H, d, Ar), 7.41–7.12 (2H, m, Ar), 6.72–6.63 (1H, dd, Ar).

7-Hydroxy-1-benzothiophene-2-carbonitrile as a solid (3.9 g, 74%). $\delta_H$ (250 MHz, DMSO-D6) 6.98 (dd, J=7.87, 0.94 Hz, 1H) 7.37 (t, J=7.87 Hz, 1H) 7.49 (dd, J=7.87, 0.94 Hz, 1H) 8.34 (s, 1H) 10.87 (s, 1H). Negative FIA: M−1=174.1.

4-Hydroxy-1-benzothiophene-2-carbonitrile as a solid (0.65 g, 95%) $\delta_H$ (300 MHz, CDCl$_3$) 8.05 (1H, s, 3-ArH), 7.43–7.34 (2H, m, ArH), 7.80–7.75 (1H, m, ArH) and 5.68 (1H, br. s, OH). Negative FIA: M−1=174.1.

4-Fluoro-7-hydroxy-1-benzothiophene-2-carbonitrile as a solid (160 mg, 27%); $\delta_H$ (300 MHz, CDCl$_3$) 7.94 (1H, s, 3-ArH), 7.04–6.92 (1H, m, ArH), 6.85–6.76 (1H, m, ArH) and 5.52 (1H, br. s, OH).

6-Hydroxy-1-benzothiophene-2-carbonitrile as a solid; (0.36 g, 64%); $\delta_H$ (300 MHz, D$_4$-Methanol) 7.85 (1H, s, ArH), 7.73–7.62 (1H, m, ArH), 7.16 (1H, s, ArH) and 6.95–6.83 (1H, m, ArH). M+1=176.1.

1-Benzofuran-7-ol, synthesised from 7-methoxy-1-benzofuran, (Ref: Musser, J. H.; Chakraborty, U; Bailey, K; Sciortino, S; Whyzmuzis, C; Amin, D; Sutherland, C. A. J. Med. Chem. (1987), 30(1), 62–7.) as a solid (0.73 g, 82%); $\delta_H$ (300 MHz, CDCl$_3$) 7.61 (1H, d, Ar), 7.16 (2H, m, Ar), 6.82 (2H, m, Ar), 5.37 (1H, bs, —OH).

6-Fluoro-1-benzothiophene-7-ol

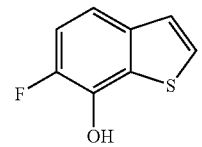

(Ref: Briner, K; Burkholder, T. P; Conway, R. G; Cunningham, B. E; Finley, D. R; Heinz, L. J; Jesudason, C. D; Kohlman, D. T; Liang, S. X; Xu, Y. C. Preparation and use of serotonergic benzothiophenes. WO 0109126 A1. Chem. Abs. 134:162912). To a solution of 7-bromo-6-fluoro-1-benzothiophene (0.2 g, 0.9 mmol) and trimethylborate (0.2 mL, 1.8 mmol) at −78° C. was added tert-butyllithium dropwise. After 10 mins at −78° C. the reaction was quenched by pouring onto saturated ammonium chloride. This was extracted with ethyl acetate (3×10 mL) and the solvent removed in vacuo from the combined organic extracts. The residue was taken up in ethyl acetate (4 mL) and 10% aqueous hydrochloric acid (4 mL) was added, the mixture was stirred at room temperature for 1 h. The organic layer was separated and the aqueous layer extracted with ethyl acetate (2×10 mL). The combined organic extracts were dried (MgSO$_4$) and the solvent removed in vacuo. The residue was taken up in THF (10 mL), water (2 mL) and cooled to 0° C. then 10% aqueous sodium hydroxide (2 mL) and 28% hydrogen peroxide (1 mL) were added to this and stirred for 0.5 h at 0° C. The mixture was warmed to room temperature and stirred for 2 hours, before a acetic acid (3 mL) was added. The mixture was extracted with ethyl acetate (3×10 mL), dried (MgSO$_4$) and the solvent removed in vacuo, to give a purple solid. This was purified by flash chromatography with a gradient of 0–20% ethyl acetate in iso-hexane to give the title compound (56 mg, 38%); $\delta_H$ (300 MHz, CDCl$_3$) 7.41 (4H, m, ArH).

4-Cyano-7-hydroxy benzo[b]thiophene

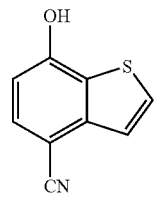

To a solution of 4-cyano-7-methoxy benzo[b]thiophene (450 mg, 2.38 mmol, 1 equiv.) in dry DMF (20 mL) was added sodium ethanethiolate (80% technical grade, 1.34 g, ~13 mmol, ~5 equiv.) and the reaction mixture was heated at 150° C. for 2 hr. The mixture was cooled to room temperature and ethyl acetate and 1N HCl were added and the layers were separated. The aqueous layer was extracted with ethyl acetate and the combined organic extracts were washed with brine (3 times), dried over anhydrous magnesium sulfate, filtered, and concentrated under reduced pressure. The acquired material thus obtained was purified via medium pressure liquid chromatography eluting with 30% ethyl acetate/70% hexanes to afford the title compound (414 mg, 99%) as a colorless solid; ☐$_H$ (400 MHz, CD$_3$OD) 6.80 (1H, d, J=8 Hz), 7.47 (1H, d, J=6 Hz), 7.64 (1H, d, J=8 Hz), 7.83 (1H, d, J=6 Hz).

1-Methyl-1H-indol-5-ol

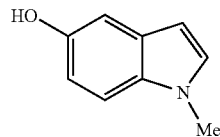

(Ref: Taborsky, R. G.; Delvigs, P; Palaic, D; Bumpus, F. M. J. Med. Chem. (1967), 10(3), 403–7). To a solution of 5-benzyloxy-1-methyl-1H-indole (2 g, 8.9 mmol) in ethanol (20 mL) was added potassium hydroxide (0.62 g, 11.2 mmol). The resulting solution was allowed to stir at room temperature for 10 mins before evaporating the ethanol in vacuo. The residue was taken up in acetone (75 mL) and sodium sulfate (6.4 g, 44.8 mmol) was added, followed by dimethyl sulfate (0.87 mL, 8.9 mmol) via syringe. The solution was stirred for 0.5 h, then filtered and evaporated in vacuo. The resulting residue was then taken up in ethanol (50 mL) and 10% palladium on charcoal (0.4 g) was added. This solution was stirred under a hydrogen atmosphere for 4 h, then filtered through celite and the solvent evaporated in vacuo. This material was purified by flash chromatography, eluting silica gel with hexane:ethyl acetate (100:0 to 50:50) to give the product. (0.48 g, 37%); δ$_H$ (300 MHz, CDCl$_3$) 7.15 (1H, d, Ar), 7.01 (2H, m, Ar), 6.8 (1H, m, Ar), 6.32 (1H, m, Ar), 3.73 (3H, s, NCH$_3$).

1-Methyl-1H-indol-7-ol
a) 7-Benzyloxy-1-methyl-1H-indole

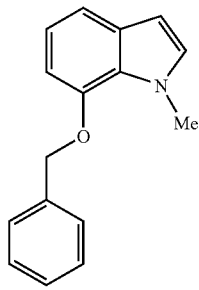

To a solution of 7-benzyloxy-1H-indole (Ref: Dobson, D; Todd, A; Gilmore, J. Synth. Commun. (1991), 21(5), 611–17) (1.29 g, 5.78 mmol) in ethanol (30 mL) was added potassium hydroxide (0.41 g, 7.23 mmol) and dichloromethane (5 mL) of to help solubilize the starting material. The resulting solution was allowed to stir at room temperature for 10 min before evaporating the solvent in vacuo. The residue was taken up in acetone (75 mL) and sodium sulfate (4.9 g, 34.7 mmol) was added followed by dimethyl sulfate via syringe (0.62 mL, 6.3 mmol). The solution was stirred for 1 h, then filtered and evaporated in vacuo. This material was purified by flash chromatography, eluting silica gel with hexane:ethyl acetate (100:0 to 10:1) to give the product. (1.12 g, 82%); Mass spectrum (ion spray): m/z=238.1 (M+1).

b) 1-Methyl-1H-indol-7-ol

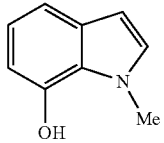

To a solution of 7-benzyloxy-1methyl-1H-indole in 20 mL of ethanol was added 10% palladium on charcoal (0.2 g). This solution was stirred under balloon pressure hydrogen atmosphere for 4 h, then filtered through celite and concentrated in vacuo. This material was purified by flash chromatography, eluting silica gel with hexane:ethyl acetate (100:0 to 50:50) to give the product (0.58 g, 87%); Mass spectrum (TOF): m/z=147.1 (M).

(1R)-3-Chloro-1-(2-thienyl)-1-pronanol
a) 3-Chloro-1-(2-thienyl)-1-propanone

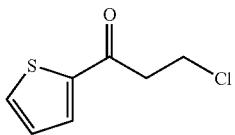

Chloropropionyl chloride (12 mL, 130 mmol) in dry dichloromethane (50 mL) was added dropwise at −5° C. to a stirred suspension of aluminium chloride (18.8 g, 141 mmol) in dry dichloromethane (100 mL). The resulting suspension was allowed to stir at −5° C. for 10 mins before a solution of thiophene (10 g, 118 mmol) in dry dichloromethane (50 mL) was added dropwise. The resulting orange solution was stirred at −5° C. for 1 hr before being carefully dropped onto crushed ice (200 g). The organic phase was separated and dried (MgSO$_4$), the solvent was then passed through a pad of celite/charcoal to remove any colour. Removal of the solvent in vacuo resulted in the title compound as a colourless oil (20 g, 100%); δ$_H$ (300 MHz, CDCl$_3$) 7.75 (1H, d, Ar), 7.68 (1H, d, Ar), 7.15 (1H, m, Ar), 3.90 (2H, t, J=7 Hz, CH$_2$), 3.38 (2H, t, J=7 Hz, CH$_2$).

b) (1R)-3-Chloro-1-(2-thienyl)-1-propanol

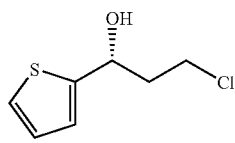

Borane dimethylsulfide complex (2.75 mL, 28.6 mmol) was added at room temperature to a stirred solution of (S)-2-methyl-CBS-oxazaborolidine (2.87 mL, 1M) in dry THF (50 mL). The resulting solution was stirred at room temperature to 10 mins before a solution of 3-chloro-1-(2-thienyl)-1-propanone (2.5 g, 14.3 mmol) in dry THF (100 mL) was added dropwise over 1 hr. After complete addition the resulting solution was stirred at room temperature for a further 1 hr before the solvent was removed in vacuo. The residue was taken up in ether (200 mL) and washed with NH$_4$Cl (sat, 100 mL). The organic phase was dried (MgSO$_4$) and concentrated in vacuo. The residue was purified by flash chromatography eluting silica gel with hexane:ether [7:3] to yield a colourless oil (2.1 g, 84%); Optical purity determined by capillary electrophoresis to be 83% ee; $\delta_H$ (300 MHz, CDCl$_3$) 7.25 (1H, d, Ar), 7.08–6.9 (2H, m, Ar), 5.28–5.20 (1H, m, CHO), 3.80–3.52 (2H, m, CH$_2$), 2.35–2.12 (2H, m, CH$_2$).

7-[(1S)-3-Chloro-1-phenylpropyl]oxy-1-benzothiophene

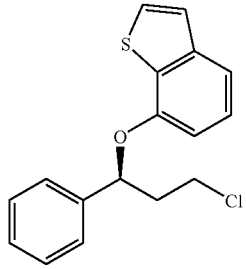

4,4-(Dimethyl-1,1-dioxido-1,2,5-thiadiazolidin-2-yl)-triphenyl phosphonium (327 mg, 0.80 mmol) was added in one portion to a stirred solution of (R)-(+)-3-chloro-1-phenyl-1-propanol (90 mg, 0.53 mmol) and 1-benzothiophen-7-ol (80 mg, 0.53 mmol) in dry THF (5 mL) under an inert atmosphere on nitrogen. The resulting suspension was allowed to stir for a further 18 hrs before the solvent was removed in vacuo. The residue was triturated with hexane (ca. 15 mL) and the solid filtered, the filtrate was concentrated in vacuo and the resulting pale yellow oil was purified by flash chromatography eluting silica gel with hexane:ether [95:5] to yield the title compound as a colourless oil (60 mg, 37%); R$_f$=0.8 in hexane:ether [10:1]; $\delta_H$ (300 MHz, CDCl$_3$) 7.66–7.00 (9H, m, Ar); 6.55 (1H, d, Ar); 5.80–5.72 (1H, m, CHO), 3.91–3.60 (2H, m, CH$_2$), 2.62–2.50 (1H, m, CHH), 2.38–2.22 (1H, m, CHH).

Similarly prepared were

4-[(1S)-3-Chloro-1-phenylpropyl]oxy-1-benzothiophene as a colourless oil (120 mg,

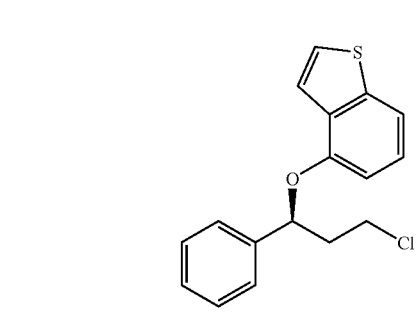

51%); $\delta_H$ (300 MHz, CDCl$_3$) 7.59–7.01 (9H, m, Ar); 6.55 (1H, d, Ar), 5.60–5.42 (1H, m, CHO), 3.84–3.70 (1H, m, CHH), 3.68–3.52 (1H, m, CHH), 2.62–2.48 (1H, m, CHH), 2.35–2.29 (1H, m, CHH).

5-[(1S)-3-Chloro-1-phenylpropyl]oxy-1-benzothiophene (from 1-benzothiophen-5-ol Ref: Perez-Silanes, S.; Martinez-Esparza, J.; Oficialdegui, A. M.; Villanueva, H.; Orus, L.; Monge, A; J. Heterocyclic Chem. 2001, 38(5) 1025.)

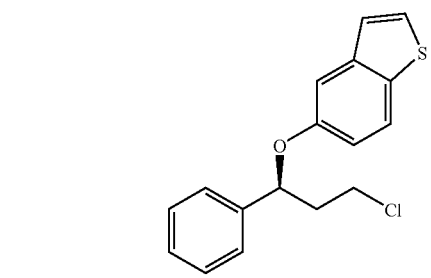

as a colourless oil (480 mg, 80%); $\delta_H$ (300 MHz, CDCl$_3$) 7.55 (1H, d, Ar), 7.65–6.81 (9H, m, Ar), 5.37–5.25 (1H, m, CHO), 3.79–3.65 (1H, m, CHH), 3.60–3.50 (1H, m, CHH), 2.48–2.32 (1H, m, CHH), 2.20–2.09 (1H, m, CHH).

6-[(1S)-3-Chloro-1-phenylpropyl]oxy-1-benzothiophene (prepared from 1-benzothiophen-6-ol Ref: Hansch, C.; Schmidhalter, B., J. Org. Chem.; 1955, 20,

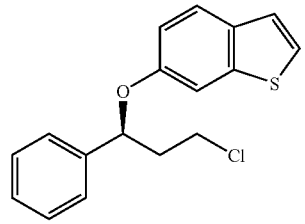

1056) as a colourless oil (363 mg, 66%); $\delta_H$ (400 MHz, CDCl$_3$) 7.62 (1H, d, J=8.0 Hz, Ar), 7.41–7.17 (8H, m, Ar), 7.0 (1H, dd, J=4, 8 Hz, Ar), 5.43 (1H, dd, J=4, 12 Hz, CHO), 3.88–3.81 (1H, m, CHH), 3.67–3.61 (1H, m, CHH), 2.54–2.47 (1H, m, CHH), 2.29–2.22 (1H, m, CHH).

7-{[(1S)-3-Chloro-1-phenylpropyl]oxy}-4-fluoro-1-benzothiophene

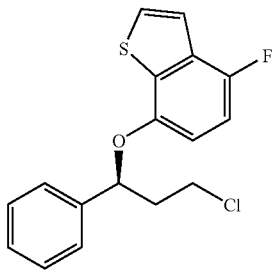

Procedure identical to above to give a colourless oil (670 mg, 76%); δ$_H$ (300 MHz, CDCl$_3$) 7.88–7.00 (8H, m, Ar); 6.55 (1H, d, Ar), 5.80–5.72 (1H, m, CHO), 3.91–3.60 (2H, m, CH$_2$), 2.62–2.50 (1H, m, CHH), 2.38–2.22 (1H, m, CHH).

7-{[(1S)-3-Chloro-1-phenylpropyl]oxy}-4-fluoro-3-methyl-1-benzothiophene

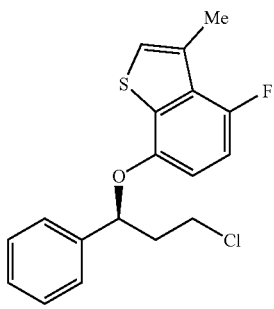

as a colourless oil (240 mg, 60%); δ$_H$ (300 MHz, CDCl$_3$) 7.42–7.20 (6H, m, Ar), 6.80–6.74 (1H, m, Ar), 7.45 (1H, dd, Ar), 5.58–5.48 (1H, m, CHO), 4.91–4.80 (1H, m, CHH), 4.71–4.59 (1H, m, CHH), 2.62–2.48 (4H, m, CHH and CH$_3$), 2.42–2.28 (1H, m, CHH).

7-{[(1S)-3-Chloro-1-phenylpropyl]oxy}-4-fluoro-3-chloro-1-benzothiophene.

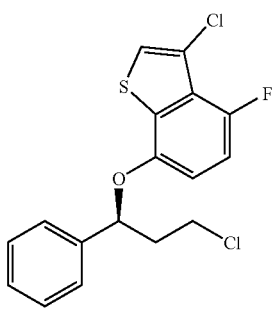

as a colourless oil (483 mg, 92%); δ$_H$ (300 MHz, CDCl$_3$) 7.40–7.12 (6H, m, Ar), 6.85–6.70 (1H, m, Ar), 6.58–6.47 (1H, m, Ar), 5.55–5.45 (1H, m, CHO), 3.90–3.78 (1H, m, CHH), 3.69–3.59 (1H, m, CHH), 2.61–2.48 (1H, m, CHH), 2.32–2.19 (1H, m, CHH).

7-{[(1S)-3-Chloro-1-phenylpropyl]oxy}-4-methyl-1-benzothiophene

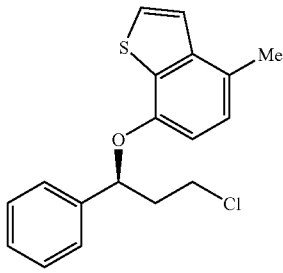

Procedure identical to above to give a colourless oil (670 mg, 76%); δ$_H$ (300 MHz, CDCl$_3$) 7.47–7.20 (7H, m, Ar), 6.89 (1H, d, Ar), 6.49 (1H, d, Ar), 5.59–5.50 (1H, m, CHO), 3.95–3.80 (1H, m, CHH), 3.72–3.62 (1H, m, CHH), 2.62–2.41 (4H, m, CHH and CH$_3$), 2.32–2.20 (1H, m, CHH).

7-{[(1S)-3-Chloro-1-phenylpropyl]oxy}-2-fluoro-1-benzothiophene

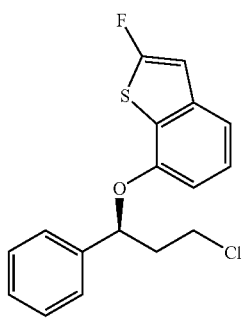

as a colourless oil (350 mg, 74%); δ$_H$ (300 MHz, CDCl$_3$) 7.45–7.02 (8H, m, Ar), 6.64–6.52 (1H, dd, Ar), 5.63–5.50 (1H, m, CHO), 3.90–3.75 (1H, m, CHH), 3.69–3.55 (1H, m, CHH), 2.62–2.48-(1H, m, CHH), 2.32–2.18 (1H, m, CHH).

7-{[(1S)-3-Chloro-1-phenylpropyl]oxy}-2-fluoro-1-benzothiophene

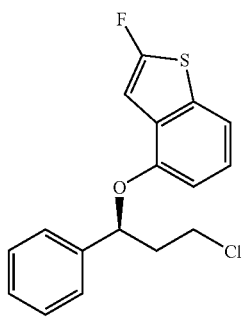

as a colourless oil (128 mg, 61%); δ$_H$ (300 MHz, CDCl$_3$) 7.48–6.50 (9H, m, Ar), 5.58–5.48 (1H, m, CHO), 3.90–3.78 (1H, m, CHH), 3.70–3.58 (1H, m, CHH), 2.61–2.45 (1H, m, CHH), 2.37–2.20 (1H, m, CHH).

7-[(1S)-3-Chloro-1-phenylpropyl]oxy-5-fluoro-1-benzothiophene

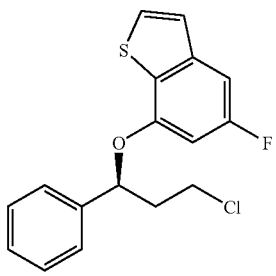

as a colourless oil (300 mg, 84%); $R_f$=0.5 in hexane:EtOAc [90:10]; $\delta_H$ (300 MHz, CDCl$_3$) 7.48 (1H, d, Ar), 7.40–7.20 (6H, m, Ar); 7.05 (1H, dd, Ar), 6.40 (1H, dd, Ar), 5.52 (1H, m, CHO), 3.91–3.60 (2H, m, CH$_2$), 2.62–2.20 (2H, m, CH$_2$).

6-[(1S)-3-Chloro-1-phenylpropyl]oxy-4-trifluoromethyl-1-benzothiophene

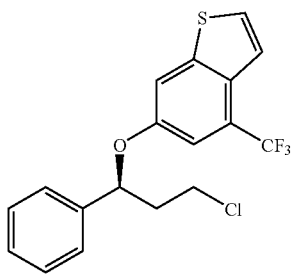

as a pale yellow oil (216 mg, 76%); $R_f$=0.4 in hexane:EtOAc [90:10]; $\delta_H$ (300 MHz, CDCl$_3$) 7.40–7.20 (9H, m, Ar); 5.45 (1H, m, CHO), 3.90–3.50 (2H, m, CH$_2$), 2.58–2.20 (2H, m, CH$_2$).

4-[(1S)-3-Chloro-1-phenylpropyl]oxy-5-fluoro-1-benzothiophene

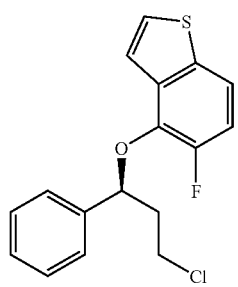

as a colourless oil (36 mg, 47%); $R_f$=0.4 in hexane:ethyl acetate [90:10]; $\delta_H$ (300 MHz, CDCl$_3$) 7.40–7.20 (8H, m, Ar); 7.00 (1H, t, Ar), 5.58 (1H, m, CHO), 3.90–3.60 (2H, m, CH$_2$), 2.80–2.22 (2H, m, CH$_2$).

4-{[(1S)-3-Chloro-1-phenyl-propyl]oxy}-7-fluoro-1-benzothiophene

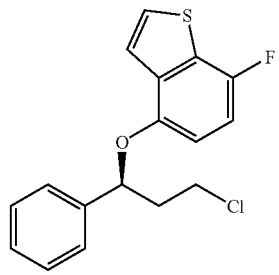

as a solid (0.30 g, 79%); $\delta_H$ (300 MHz, CDCl$_3$) 7.52–7.50 (1H, m, ArH), 7.35–7.15 (6H, m, ArH), 6.71–6.65 (1H, m, ArH), 6.42–6.39 (1H, m, ArH), 5.42–5.36 (1H, m, CHO), 3.80–3.70 (1H, m, CH$_2$CHHCl), 3.61–3.51 (1H, m, CH$_2$CHHCl), 2.52–2.41 (1H, m, CHHCH$_2$Cl) and 2.28–2.13 (1H, m, CHHCH$_2$Cl).

4-{[(1S)-3-Chloro-1-phenyl-propyl]oxy}-7-fluoro-3-methyl-1-benzothiophene

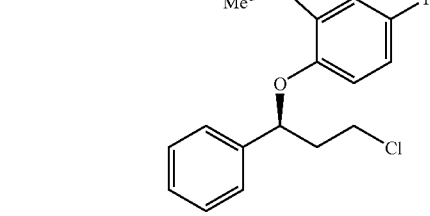

as a solid (0.25 g, 67%); $\delta_H$ (300 MHz, CDCl$_3$) 7.42–7.22 (5H, m, ArH), 6.97 (1H, s, ArH), 6.70–6.68 (1H, m, ArH), 6.45–6.40 (1H, m, ArH), 5.52–5.43 (1H, m, CHO), 3.83–3.75 (1H, m, CH$_2$CHHCl), 3.63–3.56 (1H, m, CH$_2$CHHCl), 2.76 (3H, s, OCH$_3$), 2.60–2.49 (1H, m, CHHCH$_2$Cl) and 2.34–2.22 (1H, m, CHHCH$_2$Cl).

7-{[(1S)-3-Chloro-1-phenylpropyl]oxy}-1-benzothiophene-2-carbonitrile

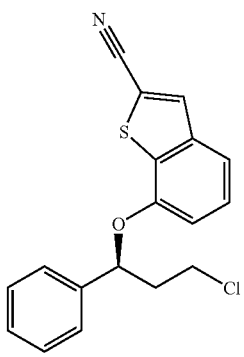

as a solid (0.22 g, 65%); $\delta_H$ (300 MHz, CDCl$_3$) 7.95 (1H, s, 3-ArH), 7.47–7.20 (7H, m, ArH), 6.79–6.71 (1H, m, ArH), 5.62–5.55 (1H, m, CHO), 3.91–3.78 (1H, m, CH$_2$CHHCl), 3.69–3.58 (1H, m, CH₂CHHCl), 2.68–2.52 (1H, m, CHHCH₂Cl) and 2.49–2.25 (1H, m, CHHCH₂Cl).

4-{[(1S)-3-Chloro-1-phenylpropyl]-oxy}-1-benzothiophene-2-carbonitrile

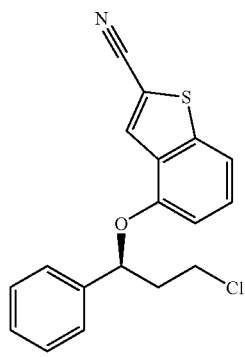

as a solid (0.15 g, 72%); δ_H (300 MHz, CDCl₃) 8.07 (1H, s, 3-ArH), 7.35–7.17 (7H, m, ArH), 6.61–6.58 (1H, m, ArH), 5.53–5.48 (1H, m, CHO), 3.80–3.68 (1H, m, CH₂CHHCl), 3.60–3.49 (1H, m, CH₂CHHCl), 2.60–2.48 (1H, m, CHHCH₂Cl) and 2.28–2.17 (1H, m, CHHCH₂Cl).

4-Cyano-7-[(1S)-3-chloro-1phenylpropyl]oxy-1-benzo[b]thiophene

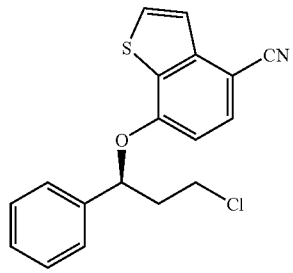

□_H (400 MHz, CDCl₃) 7.60 (1H, d, J=6 Hz), 7.48 (1H, d, J=6 Hz), 7.45 (1H, d, J=8 Hz), 7.15–7.35 (5H, m), 6.58 (1H, d, J=8 Hz), 5.60 (1H, dd, J=8, 4 Hz), 3.73–3.82 (1H, m), 3.53–3.62 (1H, m), 2.49–2.60 (1H, m), 2.20–2.31 (1H, m).

5-[(1S)-3-Chloro-1-phenylpropyl]oxy-1-methyl-1H-indole

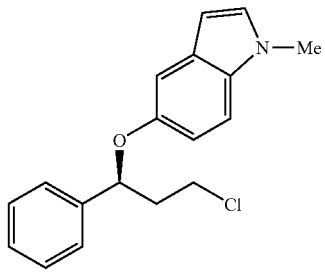

as a solid (183 mg, 41%); mass spectrum (TOF): m/z=299.11 (M).

7-[(1S)-3-Chloro-1-phenylpropyl]oxy-1-indole

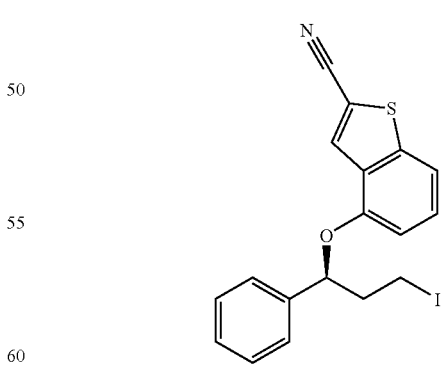

as a colourless oil (200 mg, 41%); (1H NMR CDCl3) 8.42 (1H, s, NH), 7.42–7.05 (8H, m, Ar), 6.82 (1H, t, Ar), 6.56–6.41 (1H, m, Ar), 5.55–5.45 (1H, m, CHO), 3.91–3.80 (1H, m, CHH), 3.72–3.60 (1H, m, CHH), 2.60–2.46 (1H, m, CHH), 2.32–2.20 (1H, m, CHH).

7-[(1S)-3-Chloro-1-phenylpropyl]oxy-1-indole as a colourless oil (110 mg, 51%); δ_H (300 MHz, CDCl₃) 8.15 (1H, s, NH), 7.45 (2H, d, Ar), 7.32 (2H, t, Ar), 7.30–7.22 (1H, m, Ar), 7.15 (1H, t, Ar), 7.00–6.92 (2H, m, Ar), 6.72 (1H, t, Ar), 6.35 (1H, d, Ar), 5.58–5.50 (1H, m, CHO), 3.92–3.82 (1H, m, CHH), 3.72–3.62 (1H, m, CHH), 2.65–2.52 (1H, m, CHH), 2.35–2.25 (1H, m, CHH).

4-{[(1S)-3-Iodo-1-phenylpropyl]oxy}-1-benzothiophene-2-carbonitrile

To a solution 7-{[(1S)-3-chloro-1-phenylpropyl]oxy}-1-benzothiophene-2-carbonitrile (218 mg, 0.6 mmol) in acetone (8 mL) was added sodium iodide (1.01 g, 6 mmol). This was heated to reflux for 48 h and cooled to room temperature, water (20 mL) was added and the aqueous layer extracted with diethyl ether (3×20 mL). The combined organic layers were washed with brine, dried (MgSO$_4$) and the solvent removed in vacuo to give a solid (0.22 g, 80%); δ$_H$ (300 MHz, CDCl$_3$) 7.85 (1H, s, 3-ArH), 7.43–7.19 (7H, m, ArH), 6.81–6.78 (1H, m, ArH), 5.52–5.42 (1H, m, CHO), 3.51–3.34 (1H, m, CH$_2$CHHI), 3.32–3.20 (1H, m, CH$_2$CHHI), 2.67–2.53 (1H, m, CHHCH$_2$I) and 2.42–2.30 (1H, m, CHHCH$_2$I).

Similarly prepared was

7-{[(1S)-3-Iodo-1-phenylpropyl]oxy}-1-benzothiophene-2-carbonitrile

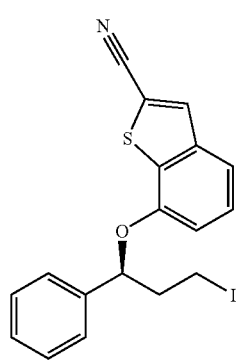

as a solid (0.22 g, 80%); δ$_H$ (300 MHz, CDCl$_3$) 7.85 (1H, s, 3-ArH), 7.43–7.19 (7H, m, ArH), 6.81–6.78 (1H, m, ArH), 5.52–5.42 (1H, m, CHO), 3.51–3.34 (1H, m, CH$_2$CHHI), 3.32–3.20 (1H, m, CH$_2$CHHI), 2.67–2.53 (1H, m, CHHCH$_2$I) and 2.42–2.30 (1H, m, CHHCH$_2$I).

4-Fluoro-7-{[(1S)-3-iodo-1-phenylpropyl]oxy}-1-benzothiophene-2-carbonitrile

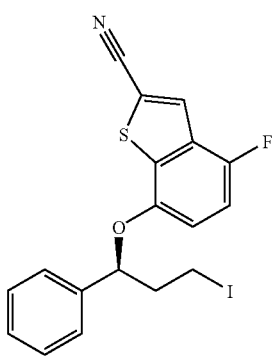

4,4-(Dimethyl-1,1-dioxido-1,2,5-thiadiazolidin-2-yl)-triphenyl phosphonium (383 mg, 0.93 mmol) was added in one portion to a stirred solution of (R)-3-iodo-1-phenyl-1-propanol (Ref: Molander, Gary A.; Shakya, Sagar R.; J. Org. Chem.; EN; 59; 12; 1994; 3445–3452.) (182 mg, 0.69 mmol) and 4-fluoro-7-hydroxy-benzo[b]thiophene-2-carbonitrile (112 mg, 0.58 mmol) in dry THF (12 mL) under an inert atmosphere on nitrogen. The resulting suspension was allowed to stir for a further 18 hrs before the solvent was removed in vacuo. The residue was purified by flash chromatography with a gradient of 0–4% diethyl ether in hexane to give the title compound as a colourless oil (0.22 g, 88%);

δ$_H$ (300 MHz, CDCl$_3$) 7.83 (1H, s, 3-ArH), 7.36–7.12 (5H, m, ArH), 6.85–6.75 (1H, m, ArH), 6.65–6.57 (1H, m, ArH), 5.40–5.30 (1H, m, CHO), 3.47–3.28 (1H, m, CH$_2$CHHI), 3.23–3.12 (1H, m, CH$_2$CHHI), 2.60–2.42 (1H, m, CHHCH$_2$I) and 2.34–2.19 (1H, m, CHHCH$_2$I).

Similarly prepared was

6-{[(1S)-3-Iodo-1-phenylpropyl]oxy}-1-benzothiophene-2-carbonitrile

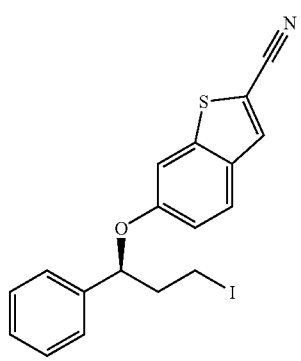

as a solid (0.29 g, 99%); δ$_H$ (300 MHz, CDCl$_3$) 7.75–7.65 (2H, m, ArH), 7.41–7.02 (7H, m, ArH), 5.39–5.29 (1H, m, CHO), 3.43–3.30 (1H, m, CH$_2$CHHI), 3.30–3.3.18 (1H, m, CH$_2$CHHI), 2.59–2.42 (1H, m, CHHCH$_2$I) and 2.39–2.22 (1H, m, CHHCH$_2$I).

7-{[(1S)-3-Iodo-1-phenyl-propyl]oxy}-6-fluoro-1-benzothiophene

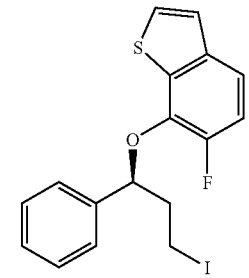

as a solid (0.21 g, 52%); δ$_H$ (300 MHz, CDCl$_3$) 7.42 (9H, m, ArH), 5.55–5.49 (1H, m, CHO), 3.38–3.21 (1H, m, CH$_2$CHHI), 3.21–3.10 (1H, m, CH$_2$CHHI), 2.70–2.65 (1H, m, CHHCH$_2$I) and 2.40–2.26 (1H, m, CHHCH$_2$I).

5-[(1S)-3-Iodo-1-phenylpropyl]oxy-1-methyl-1H-indole

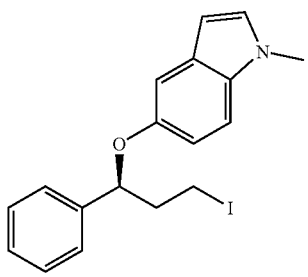

as a solid (131 mg, 63%); mass spectrum (TOF): m/z=391.04 (M)

7-[(1S)-3-Iodo-1-phenyl-propoxy)-benzofuran

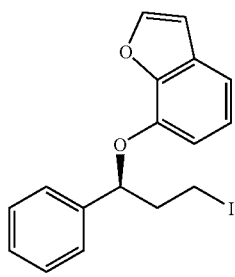

to give the title compound (1.2 g, 85%); δ$_H$ (300 MHz, CDCl$_3$) 7.64 (1H, d, Ar), 7.44 (2H, m, Ar), 7.29 (3H, m, Ar), 7.13 (1H, m, Ar), 6.99 (1H, m, Ar), 6.75 (1H, m, Ar), 6.66 (1H, m, Ar), 5.50 (1H, m, O—CH), 3.47 (1H, m, CH2), 3.33 (1H, m, CH2), 2.64 (1H, m, CH2), 2.38 (1H, m, CH2).

7-{[(1S)-3-Chloro-1-(2-thienyl)propyl]oxy}-1-benzothiophene

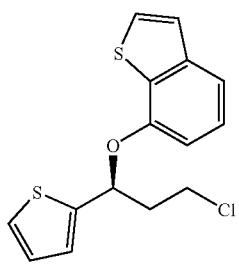

4,4-(Dimethyl-1,1-dioxido-1,2,5-thiadiazolidin-2-yl)-triphenyl phosphonium (329 mg, 0.799 mmol) was added in one portion to a stirred solution of (1R)-3-chloro-1-(2-thienyl)-1-propanol (92 mg, 0.533 mmol) and 7-hydroxy-benzo[b]thiophene (80 mg, 0.533 mmol) in dry THF (5 mL) under an inert atmosphere on nitrogen. The resulting suspension was allowed to stir for a further 18 hrs before the solvent was removed in vacuo. The residue was triturated with hexane (ca. 15 mL) and the solid filtered, the filtrate was concentrated in vacuo and the resulting pale yellow oil was purified by flash chromatography eluting silica gel with hexane:ether [95:5] to yield the title compound as a colourless oil (35 mg, 21%); R$_f$=0.78 in hexane:ether [10:1]; δ$_H$ (300 MHz, CDCl$_3$) 7.52–6.80 (9H, m, Ar), 5.95–5.88 (1H, m, CHO), 3.90–3.79 (1H, m, CHH), 3.70–3.58 (1H, m, CHH), 2.80–2.65 (1H, m, CHH), 2.55–2.30 (1H, m, CHH)

7-[(1R)-3-Chloro-1-phenylpropyl]oxy-1-benzothiophene

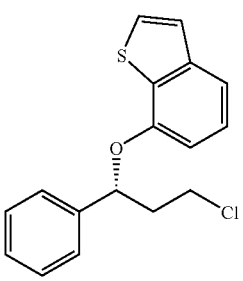

4,4-(Dimethyl-1,1-dioxido-1,2,5-thiadiazolidin-2-yl)-triphenyl phosphonium (1.15 g, 2.80 mmol) was added in one portion to a stirred solution of (S)-(−)-3-chloro-1-phenyl-1-propanol (317 mg, 1.86 mmol) and 7-hydroxy-benzo[b]thiophene (280 mg, 1.86 mmol) in dry THF (5 mL) under an inert atmosphere on nitrogen. The resulting suspension was allowed to stir for a further 18 hrs before the solvent was removed in vacuo. The residue was triturated with hexane (ca. 15 mL) and the solid filtered, the filtrate was concentrated in vacuo and the resulting pale yellow oil was purified by flash chromatography eluting silica gel with hexane:ether [95:5] to yield the title compound as a colourless oil (240 mg, 43%); R$_f$=0.78 in hexane:ether [10:1]; δ$_H$ (300 MHz, CDCl$_3$) 7.66–7.00 (9H, m, Ar); 6.55 (1H, d, Ar), 5.80–5.72 (1H, m, CHO), 3.91–3.60 (2H, m, CH$_2$), 2.62–2.50 (1H, m, CHH), 2.38–2.22 (1H, m, CHH).

Similarly prepared were

4-[(1R)-3-Chloro-1-phenylpropyl]oxy-1-benzothiophene as a colourless oil

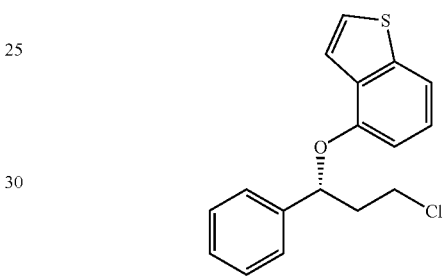

(104 mg 52%); δ$_H$ (300 MHz, CDCl$_3$) 7.59–7.01 (9H, m, Ar); 6.55 (1H, d, Ar), 5.60–5.42 (1H, m, CHO), 3.84–3.70 (1H, m, CHH), 3.68–3.52 (1H, m, CHH), 2.62–2.48 (1H, m, CHH), 2.35–2.29 (1H, m, CHH).

5-[(1R)-3-Chloro-1-phenylpropyl]oxy-1-benzothiophene (from 1-benzothiophen-5-ol Ref: Perez-Silanes, S.; Martinez-Esparza, J.; Oficialdegui, A. M.; Villanueva, H.; Orus, L.; Monge, A; J. Heterocyclic Chem. 2001, 38(5) 1025) as a colourless oil (540 mg, 89%); δ$_H$ (300 MHz, CDCl$_3$) 7.55 (1H, d, Ar), 7.65–6.81 (9H, m, Ar), 5.37–5.25 (1H, m, CHO), 3.79–3.65 (1H, m, CHH), 3.60–3.50 (1H, m, CHH), 2.48–2.32 (1H, m, CHH), 2.20–2.09 (1H, m, CHH).

6-[(1R)-3-Chloro-1-phenylpropyl]oxy-1-benzothiophene (prepared from 1-benzothiophen-6-ol Ref: Hansch, C.; Schmidhalter, B., J. Org. Chem.; 1955, 20, 1056)

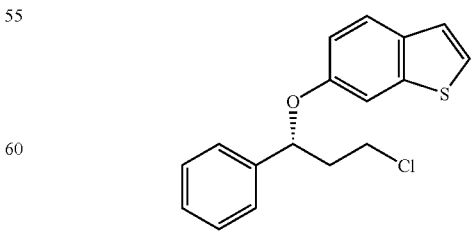

as a colourless oil (370 mg, 67%); δ$_H$ (400 MHz, CDCl$_3$) 7.53 (1H, d, J=8.0 Hz, Ar), 7.32–7.08 (8H, m, Ar), 6.90(1H, d, J=4, 8 Hz, Ar), 5.34 (1H, dd, J=4, 12 Hz, CHO), 3.79–3.72 (1H, m, CHH), 3.58–3.52 (1H, m, CHH), 2.46–2.37 (1H, m, CH H), 2.20–2.12 (1H, m, CHH).

7-{[(1R)-3-Chloro-1-phenylpropyl]oxy}-4-fluoro-1-benzothiophene

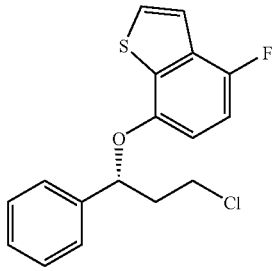

as a colourless oil (824 mg, 93%); $\delta_H$ (300 MHz, CDCl$_3$) 7.88–7.00 (8H, m, Ar); 6.55 (1H, d, Ar), 5.80–5.72 (1H, m, CHO), 3.91–3.60 (2H, m, CH$_2$), 2.62–2.50 (1H, m, CHH), 2.38–2.22 (1H, m, CHH).

7-{[(1R)-3-Chloro-1-phenylpropyl]oxy}-4-fluoro-3-methyl-1-benzothiophene.

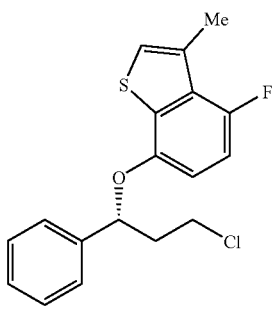

as a colourless oil (326 mg, 81%); $\delta_H$ (300 MHz, CDCl$_3$) 7.42–7.20 (6H, m, Ar), 6.80–6.74 (1H, m, Ar), 7.45 (1H, dd, Ar), 5.58–5.48 (1H, m, CHO), 4.91–4.80 (1H, m, CHH), 4.71–4.59 (1H, m, CHH), 2.62–2.48 (4H, m, CHH and CH$_3$), 2.42–2.28 (1H, m, CHH).

7-{[(1R)-3-Chloro-1-phenylpropyl]oxy}-4-fluoro-3-chloro-1-benzothiophene

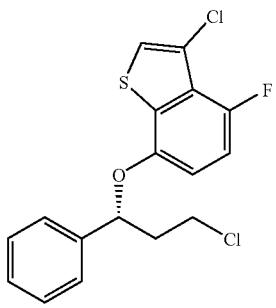

as a colourless oil (490 mg, 94%); $\delta_H$ (300 MHz, CDCl$_3$) 7.40–7.12 (6H, m, Ar), 6.85–6.70 (1H, m, Ar), 6.58–6.47 (1H, m, Ar), 5.55–5.45 (1H, m, CHO), 3.90–3.78 (1H, m, CHH), 3.69–3.59 (1H, m, CHH), 2.61–2.48 (1H, m, CHH), 2.32–2.19 (1H, m, CHH).

7-{[(1R)-3-Chloro-1-phenylpropyl]oxy}-4-methyl-1-benzothiophene

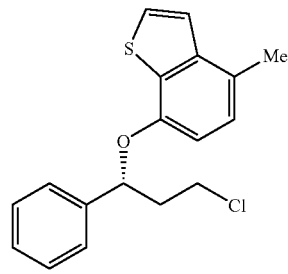

as a colourless oil (824 mg, 93%); $\delta_H$ (300 MHz, CDCl$_3$) 7.47–7.20 (7H, m, Ar), 6.89 (1H, d, Ar), 6.49 (1H, d, Ar), 5.59–5.50 (1H, m, CHO), 3.95–3.80 (1H, m, CHH), 3.72–3.62 (1H, m, CHH), 2.62–2.41 (4H, m, CHH and CH$_3$), 2.32–2.20 (1H, m, CHH).

7-{[(1R)-3-Chloro-1-phenylpropyl]oxy}-2-fluoro-1-benzothiophene

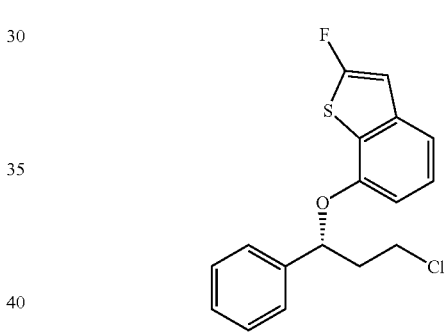

as a colourless oil (370 mg, 78%); $\delta_H$ (300 MHz, CDCl$_3$) 7.45–7.02 (8H, m, Ar), 5.64–5.52 (1H, dd, Ar), 5.63–5.50 (1H, m, CHO), 3.90–3.75 (1H, m, CHH), 3.69–3.55 (1H, m, CHH), 2.62–2.48-(1H, m, CHH), 2.32–2.18 (1H, m, CHH).

4-{[(1R)-3-Chloro-1-phenylpropyl]oxy}-2-fluoro-1-benzothiophene

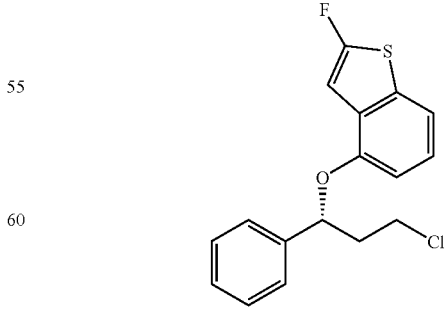

as a colourless oil (150 mg, 72%); $\delta_H$ (300 MHz, CDCl$_3$) 7.48–6.50 (9H, m, Ar), 5.58–5.48 (1H, m, CHO), 3.90–3.78

(1H, m, CHH), 3.70–3.58 (1H, m, CHH), 2.61–2.45-(1H, m, CHH), 2.37–2.20 (1H, m, CHH).

7-[(1R)-3-Chloro-1-phenylpropyl]oxy-5-fluoro-1-benzothiophene

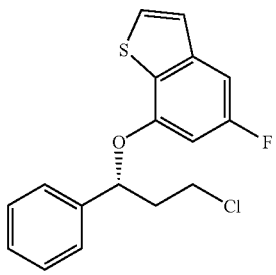

as a colourless oil (287 mg, 81%); $R_f$=0.5 in hexane:EtOAc [90:10]; $\delta_H$ (300 MHz, CDCl$_3$) 7.48 (1H, d, Ar), 7.40–7.20 (6H, m, Ar); 7.05 (1H, dd, Ar), 6.40 (1H, dd, Ar), 5.52 (1H, m, CHO), 3.91–3.60 (2H, m, CH$_2$), 2.62–2.20 (2H, m, CH$_2$).

6-[(1R)-3-Chloro-1-phenylpropyl]oxy-4-trifluoromethyl-1-benzothiophene

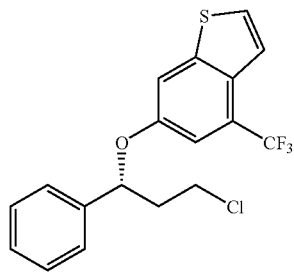

as a pale yellow oil (265 mg, 0.715 mmol, 84%); $R_f$=0.4 in hexane:EtOAc [90:10]; $\delta_H$ (300 MHz, CDCl$_3$) 7.40–7.20 (9H, m, Ar); 5.45 (1H, m, CHO), 3.90–3.55 (2H, m, CH$_2$), 2.60–2.15 (2H, m, CH$_2$).

4-[(1R)-3-Chloro-1-phenylpropyl]oxy-5-fluoro-1-benzothiophene

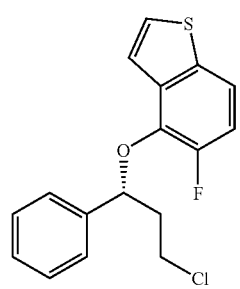

as a colourless oil (41 mg, 67%); $R_f$=0.4 in hexane:EtOAc [90:10]; $\delta_H$ (300 MHz, CDCl$_3$) 7.40–7.20 (8H, m, Ar); 7.00 (1H, t, Ar), 5.58 (1H, m, CHO), 3.90–3.55 (2H, m, CH$_2$), 2.80–2.22 (2H, m, CH$_2$).

4-{[(1R)-3-Chloro-1-phenylpropyl]oxy}-7-fluoro-1-benzothiophene

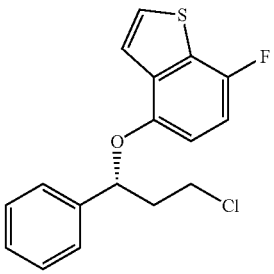

as a solid (0.37 g, 95%); $\delta_H$ (300 MHz, CDCl$_3$) 7.52–7.50 (1H, m, ArH), 7.35–7.15 (6H, m, ArH), 6.71–6.65 (1H, m, ArH), 6.42–6.39 (1H, m, ArH), 5.42–5.36 (1H, m, CHO), 3.80–3.70 (1H, m, CH$_2$CHHCl), 3.61–3.51 (1H, m, CH$_2$CHHCl), 2.52–2.41 (1H, m, CHHCH$_2$Cl) and 2.28–2.13 (1H, m, CHHCH$_2$Cl).

4-{[(1R)-3-Chloro-1-phenyl-propyl]oxy}-7-fluoro-3-methyl-1-benzothiophene

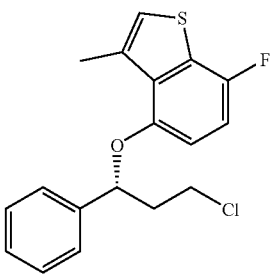

as a solid (0.34 g, 93%); $\delta_H$ (300 MHz, CDCl$_3$) 7.42–7.22 (5H, m, ArH), 6.97 (1H, s, ArH), 6.70–6.68 (1H, m, ArH), 6.45–6.40 (1H, m, ArH), 5.52–5.43 (1H, m, CHO), 3.83–3.75 (1H, m, CH$_2$CHHCl), 3.63–3.56 (1H, m, CH$_2$CHHCl), 2.76 (3H, s, OCH$_3$), 2.60–2.49 (1H, m, CHHCH$_2$Cl) and 2.34–2.22 (1H, m, CHHCH$_2$Cl).

7-{[(1R)-3-Chloro-1-phenylpropyl]oxy}-1-benzothiophene-2-carbonitrile

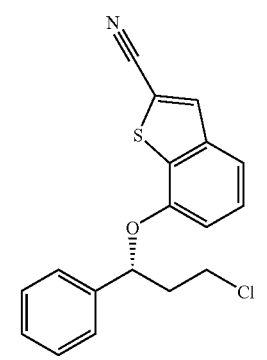

as a solid (0.22 g, 71%); $\delta_H$ (300 MHz, CDCl$_3$) 7.95 (1H, s, 3-ArH), 7.47–7.20 (7H, m, ArH), 6.79–6.71 (1H, m, ArH), 5.62–5.55 (1H, m, CHO), 3.91–3.78 (1H, m, CH$_2$CHHCl), 3.69–3.58 (1H, m, CH₂CHHCl), 2.68–2.52 (1H, m, CHHCH₂Cl) and 2.49–2.25 (1H, m, CHHCH₂Cl).

4-{[(1R)-3-Chloro-1-phenylpropyl]oxy}-1-benzothiophene-2-carbonitrile

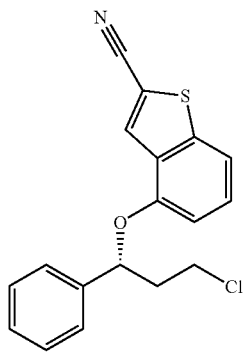

as a solid (0.17 g, 78%); δ$_H$ (300 MHz, CDCl₃) 8.07 (1H, s, 3-ArH), 7.35–7.17 (7H, m, ArH), 6.61–6.58 (1H, m, ArH), 5.53–5.48 (1H, m, CHO), 3.80–3.68 (1H, m, CH₂CHHCl), 3.60–3.49 (1H, m, CH₂CHHCl), 2.60–2.48 (1H, m, CHHCH₂Cl) and 2.28–2.17 (1H, m, CHHCH₂Cl).

4-Cyano-7-[(1R)-3-chloro-1phenylpropyl]oxy-1-benzo[b]thiophene

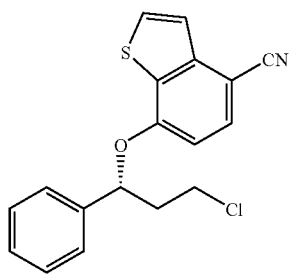

☐$_H$ (400 MHz, CDCl₃) 7.60 (1H, d, J=6 Hz), 7.48 (1H, d, J=6 Hz), 7.45 (1H, d, J=8 Hz), 7.15–7.35 (5H, m), 6.58 (1H, d, J=8 Hz), 5.60 (1H, dd, J=8, 4 Hz), 3.73–3.82 (1H, m), 3.53–3.62 (1H, m), 2.49–2.60 (1H, m), 2.20–2.31 (1H, m).

7-[(1R)-3-Chloro-1-phenylpropyl]oxy-1-indole

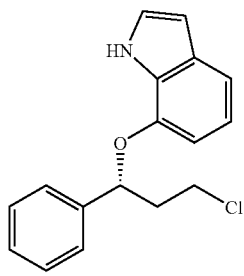

as a colourless oil (103 mg, 21%); (1H NMR CDCl3) 8.42 (1H, s, NH), 7.42–7.05 (8H, m, Ar), 6.82 (1H, t, Ar), 6.56–6.41 (1H, m, Ar), 5.55–5.45 (1H, m, CHO), 3.91–3.80 (1H, m, CHH), 3.72–3.60 (1H, m, CHH), 2.60–2.46 (1H, m, CHH), 2.32–2.20 (1H, m, CHH).

4-[(1R)-3-Chloro-1-phenylpropyl]oxy-1-indole

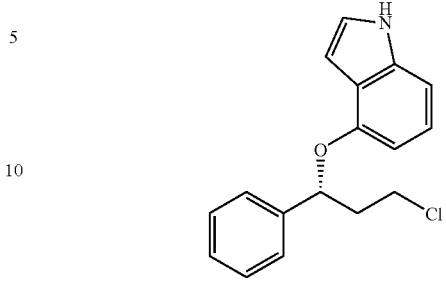

as a colourless oil (100 mg, 47%); 8.15 (1H, s, NH), 7.45 (2H, d, Ar), 7.32 (2H, t, Ar), 7.30–7.22 (1H, m, Ar), 7.15 (1H, t, Ar), 7.00–6.92 (2H, m, Ar), 6.72 (1H, t, Ar), 6.35 (1H, d, Ar), 5.58–5.50 (1H, m, CHO), 3.92–3.82 (1H, m, CHH), 3.72–3.62 (1H, m, CHH), 2.65–2.52 (1H, m, CHH), 2.35–2.25 (1H, m, CHH).

5-[(1R)-3-Chloro-1-phenylpropyl]oxy-1-methyl-1H-indole

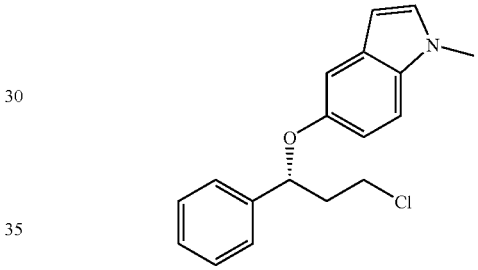

(138 mg, 31%); mass spectrum (TOF): m/z=299.11 (M).

7-{[(1R)-3-Iodo-1-Phenylpropyl]oxy}-1-benzothiophene-2-carbonitrile

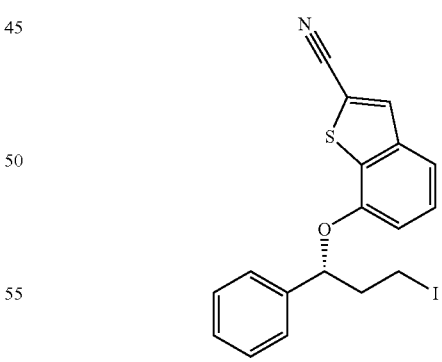

To a solution 7-{[(1R)-3-chloro-1-phenylpropyl]oxy}-1-benzothiophene-2-carbonitrile (52 mg, 0.16 mmol) in acetone (2 mL) was added sodium iodide (240 mg, 1.6 mmol). This was heated to reflux for 48 h and cooled to room temperature, water (5 mL) was added and the aqueous layer extracted with diethyl ether (3×5 mL). The combined organic layers were washed with brine, dried (MgSO₄) and the solvent removed in vacuo to give a solid (66 mg, 100%) which was used without further purification; $\delta_H$ (300 MHz, CDCl$_3$) 7.85 (1H, s, 3-ArH), 7.43–7.19 (7H, m, ArH), 6.81–6.78 (1H, m, ArH), 5.52–5.42 (1H, m, CHO), 3.51–3.34 (1H, m, CH$_2$CHHI), 3.32–3.20 (1H, m, CH$_2$CHHI), 2.67–2.53 (1H, m, CHHCH$_2$I) and 2.42–2.30 (1H, m, CHHCH$_2$I).

Similarly prepared was

4-{[(1R)-3-Iodo-1-phenylpropyl]oxy}-1-benzothiophene-2-carbonitrile

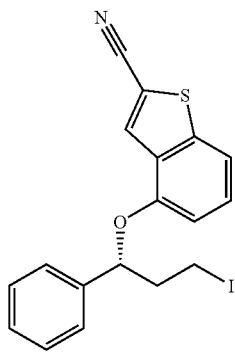

as a solid (0.19 g, 90%); $\delta_H$ (300 MHz, CDCl$_3$) 8.09 (1H, s, 3-ArH), 7.36–7.15 (7H, m, ArH), 6.60–6.55 (1H, m, ArH), 5.42–5.35 (1H, m, CHO), 3.38–3.23 (1H, m, CH$_2$CHHI), 3.23–3.10 (1H, m, CH$_2$CHHI), 2.60–2.43 (1H, m, CHHCH$_2$I) and 2.39–2.22 (1H, m, CHHCH$_2$I).

5-[(1R)-3-Iodo-1-phenylpropyl]oxy-1-methyl-1H-indole

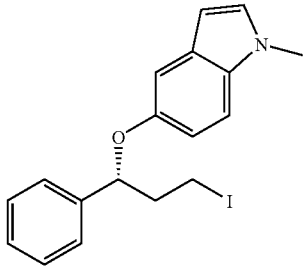

(131 mg, 62%); mass spectrum (TOF): m/z=391.04 (M).

4-Fluoro-7-{[(1R)-3-iodo-1-phenylpropyl]oxy}-1-benzothiophene-2-carbonitrile

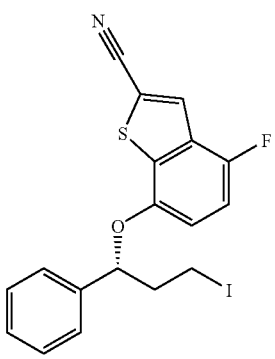

4,4-(Dimethyl-1,1-dioxido-1,2,5-thiadiazolidin-2-yl)-triphenyl phosphonium (498 mg, 1.12 mmol) was added in one portion to a stirred solution of (S)-3-iodo-1-phenyl-1-propanol (Molander, Gary A.; Shakya, Sagar R.; J. Org. Chem.; 1994, 59; 12; 1994; 3445–3452) (237 mg, 0.84 mmol) and 4-fluoro-7-hydroxy-benzothiophene-2-carbonitrile (144 mg, 0.70 mmol) in dry THF (12 mL) under an inert atmosphere on nitrogen. The resulting suspension was allowed to stir for a further 18 hrs before the solvent was removed in vacuo. The residue was purified by flash chromatography with a gradient of 0–4% diethyl ether in hexane to give the title compound as a colourless oil (284 mg, 72%); $\delta_H$ (300 MHz, CDCl$_3$) 7.83 (1H, s, 3-ArH), 7.36–7.12 (5H, m, ArH), 6.85–6.75 (1H, m, ArH), 6.65–6.57 (1H, m, ArH), 5.40–5.30 (1H, m, CHO), 3.47–3.28 (1H, m, CH$_2$CHHI), 3.23–3.12 (1H, m, CH$_2$CHHI), 2.60–2.42 (1H, m, CHHCH$_2$I) and 2.34–2.19 (1H, m, CHHCH$_2$I).

Similarly prepared were

6-{[(1R)-3-Iodo-1-phenylpropyl]oxy}-1-benzothiophene-2-carbonitrile

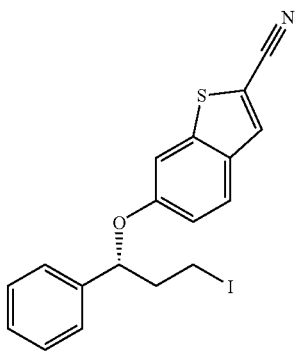

as a solid (0.23 g, 80%); $\delta_H$ (300 MHz, CDCl$_3$) 7.75–7.65 (2H, m, ArH), 7.41–7.02 (7H, m, ArH), 5.39–5.29 (1H, m, CHO), 3.43–3.30 (1H, m, CH$_2$CHHI), 3.30–3.3.18 (1H, m, CH$_2$CHHI), 2.59–2.42 (1H, m, CHHCH$_2$I) and 2.39–2.22 (1H, m, CHHCH$_2$I).

7-{[(1R)-3-Iodo-1-phenyl-propyl]oxy}-6-fluoro-1-benzothiophene

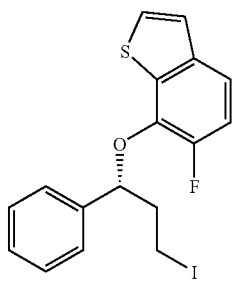

as a solid (0.18 g, 50%); δ$_H$ (300 MHz, CDCl$_3$) 7.42 (9H, m, ArH), 5.55–5.49 (1H, m, CHO), 3.38–3.21 (1H, m, CH$_2$CHHI), 3.21–3.10 (1H, m, CH$_2$CHHI), 2.70–2.65 (1H, m, CHHCH$_2$I) and 2.40–2.26 (1H, m, CHHCH$_2$I).

7-[(1R)-3-Iodo-1-phenyl-propoxy)-1-benzofuran

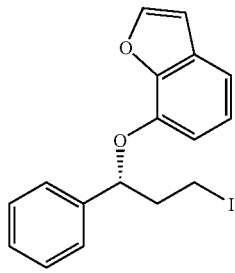

to give the title compound (1.4 g, 100%); δ$_H$ (300 MHz, CDCl$_3$) 7.64 (1H, d, Ar), 7.44 (2H, m, Ar), 7.29 (3H, m, Ar), 7.13 (1H, m, Ar), 6.99 (1H, m, Ar), 6.75 (1H, m, Ar), 6.66 (1H, m, Ar), 5.50 (1H, m, O—CH), 3.47 (1H, m, CH$_2$), 3.33 (1H, m, CH$_2$), 2.64 (1H, m, CH$_2$), 2.38 (1H, m, CH$_2$).

1-Benzothiophene-7-thiol

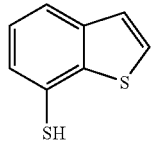

To a cooled solution (–78° C.) of 7-bromo-1-benzothiophene (10 g, 46.8 mmol) in dry THF was added sulfur (1.5 g, 46.8 mmol). A solution of tert-butyl lithium in hexane (1.7 M, 55 mL, 92 mmol) was then added dropwise via cannular over 30 mins. The resulting suspension was allowed to stir at –78° C. for a further 30 mins before being diluted with saturated aqueous ammonium chloride (50 mL). The reaction mixture was allowed to warm to room temperature and extracted with diethyl ether (100 mL). The organic phase was further extracted with aqueous sodium hydroxide solution (2 N, 2×100 mL), the base washes were collected, washed with diethyl ether (4×100 mL) and then acidified to pH 2–3 with aqueous hydrochloric (5 N). Further diethyl ether extracts were subsequently washed with brine (4×100 mL), with the resulting organic phase being dried (MgSO$_4$) and the solvent evapotated in vacuo to give a pale yellow oil (2.4 g, 45%). δ$_H$ (300 MHz, CDCl$_3$) 7.7 (1H, d, S—CH═CH), 7.5 (1H, d, S—CH═CH), 7.25–7.4 (3H, m, Ar), 3.61 (1H, s, SH).

3-[Benzyl(methyl)amino]-1-phenyl-1-propanol

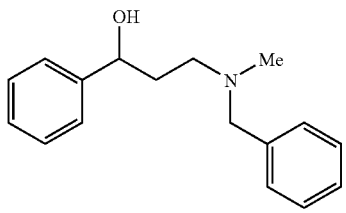

A solution of 3-chloro-1-phenylpropan-1-ol (2 g, 11.7 mmol), N-methylbenzylamine (2.12 g, 17.5 mmol), potassium iodide (2.6 g, 22 mmol), and potassium carbonate (3.2 g, 23.4 mmol) in dimethylformamide (120 mL) was stirred at 90° C. in a reacti-vial for 16 h. After this time the reaction was allowed to cool to room temperature. The reaction mixture was purified by an SCX-2 column eluting with Methanol followed by ammonia:methanol solution (7 N). The organics were then evaporated and the compound taken directly onto the next step without any further purification. (M$^+$H+1 [256]); δ$_H$ (300 MHz, CDCl$_3$) 7.2–7.4 (10H, m, Ar), 4.9 (1H, t, C$\underline{H}$—OH), 3.55 (1H, d, C$\underline{H}_2$—Ph), 3.45 (1H, d, C$\underline{H}_2$—PH), 2.8–3 (1H, m, CH$_2$), 2.55–2.65 (1H, m, CH$_2$), 2.25 (3H, s, CH$_3$), 1.8–1.9 (2H, m, CH$_2$), 1.6 (1H, brs, OH).

1-Benzothien-7-yl(thio)-N-benzyl-N-methyl-3-phenylpropanamine

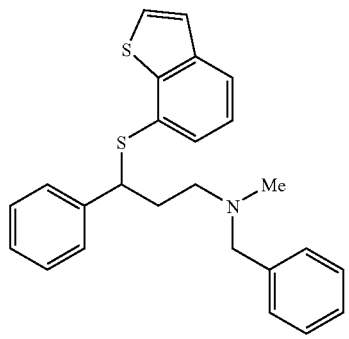

A solution of 1-benzothiophene-7-thiol (0.32 g, 1.96 mmol), 3-[benzyl(methyl)amino]-1-phenyl-1-propanol (0.5 g, 1.96 mmol), (cyanomethyl) trimethylphosphonium iodide (Ref Tetrahedron, 2001, 57, 5451–5454) (0.714 g, 2.94 mmol), diisopropylethylamine (0.379 g, 2.94 mmol) in propionitrile (5 mL) was stirred at 90° C. in a reacti-vial for 72 h. After this time the reaction was allowed to cool to room temperature. The reaction mixture was purified by an SCX-2 column eluting with methanol followed by ammonia:methanol solution (7 N). The organics were then evaporated and the compound taken directly onto the next step without any further purification LCMS determined successful product formation (M$^+$H+1 [404]).

3-(1-Benzothienyl-4-yl(thio)-N-benzyl-N-methyl-3-phenyl-1-propanamine

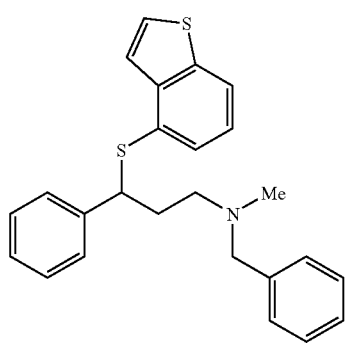

A solution of 1-benzothiophene-4-thiol (0.32 g, 1.96 mmol), 3-[benzyl(methyl)amino]-1-phenyl-1-propanol (0.5 g, 1.96 mmol), (cyanomethyl) trimethylphosphonium iodide (Ref Tetrahedron, 2001, 57, 5451–5454) (0.714 g, 2.94 mmol), diisopropylethylamine (0.379 g, 2.94 mmol) in propionitrile (5 mL) was stirred at 90° C. in a reacti-vial for 72 h. After this time the reaction was allowed to cool to room temperature. The reaction mixture was purified by an SCX-2 column eluting with methanol followed by ammonia:methanol solution (7 N). The organics were then evaporated and the compound taken directly onto the next step without any further purification. Product formation was determined by LCMS (M$^+$H+1 [404]).

In the following section, there is described the synthesis of compounds of the present invention.

EXAMPLE 1

(3S)-3-(1-Benzothien-7-yloxy)-N-methyl-3-phenyl-1-propanamine oxalate

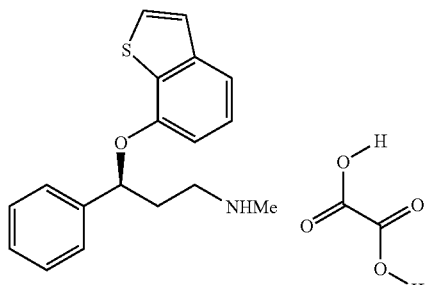

Methylamine (40% in water, 3 mL) was dissolved in a solution of 7-[(1S)-3-chloro-1-phenylpropyl]oxy-1-benzothiophene (60 mg, 0.19 mmol) in ethanol (abs, 3 mL), the resulting solution was heated to 130° C. in a sealed bomb for 3 h. After this time the reaction was allowed to cool to room temperature before the solvent was removed in vacuo. The residue was purified by flash chromatography eluting silica gel with CHCl$_3$:Methanol [10:1] to yield a colourless oil.

The resulting oil was dissolved in ethyl acetate (5 mL) and a solution of oxalic acid (16 mg, 0.126 mmol) in ethyl acetate (2 mL) added. The mixture was stirred at room temperature for 10 mins and then the solvent removed in vacuo. The residue was dissolved in acetonitrile (1 mL) and water (5 mL), this solution was then frozen by immersion in a dry ice:acetone bath, the resulting frozen material was freeze dried overnight to yield the target compound as a fluffy white solid (72 mg); δ$_H$ (300 MHz, CDCl$_3$) 7.50–7.25 (8H, m, Ar), 7.15 (1H, t, Ar), 6.55 (1H, d, Ar), 5.50 (1H, bd, CHO), 3.70 (3H, s, NCH$_3$), 3.22 (2H, m, CH$_2$), 2.42 (2H, m, CH$_2$).

Similarly prepared were

EXAMPLE 2

(3S)-3-(1-Benzothien-4-yloxy)-N-methyl-3-phenyl-1-propanamine oxalate

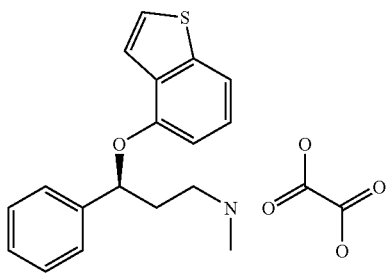

as a solid (124 mg, 82%); δ$_H$ (300 MHz, CD$_3$OD) 7.50–7.25 (8H, m, Ar), 7.15 (1H, t, Ar), 6.55 (1H, d, Ar), 5.62–5.44 (1H, m, CHO), 3.70 (3H, s, NCH$_3$), 3.36–3.21 (2H, m, CH$_2$), 2.50–2.36 (2H, m, CH$_2$).

EXAMPLE 3

(3S)-3-(1-Benzothien-5-yloxy)-N-methyl-3-phenyl-1-propanamine oxalate

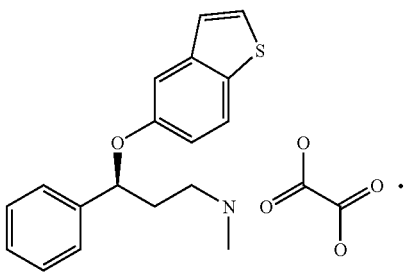

as a solid (200 mg, 82%); δ$_H$ (300 MHz, CD$_3$OD) 8.00–7.91 (1H, d, Ar), 7.70–7.22 (9H, m, Ar), 5.70–5.60 (1H, m, CHO), 3.58 (3H, s, NCH$_3$), 3.56–3.38 (2H, m, CH$_2$), 2.52–2.36 (2H, m, CH$_2$).

EXAMPLE 3A (3S)-3-(1-Benzothien-6-yloxy)-N-methyl-3-phenyl-1-propanamine hydrochloride

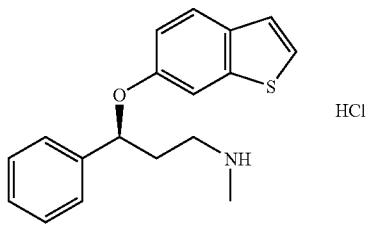

as a solid (268 mg, 74%); δ$_H$ (400 MHz, CDCl$_3$) 7.61 (1H, d, J=9.0 Hz, Ar), 7.39–7.16 (8H, m, Ar), 6.99 (1H, dd, J=2,8

Hz, Ar), 5.30 (1H, dd, J=5, 8 Hz, CHO), 2.81–2.78 (2H, m, CH₂), 2.45 (3H, s, NCH₃), 2.26–2.20 (1H, m, CH H), 2.08–2.03 (1H, m, CH H).

EXAMPLE 4

(3S)-3-(1-Indol-7-yloxy)-N-methyl-3-phenyl-1-propanamine oxalate

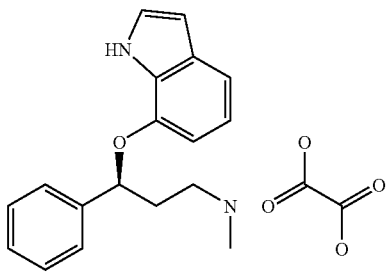

as a solid (89 mg, 40%); $\delta_H$ (300 MHz, CD₃OD) 7.40–6.92 (8H, m, Ar), 6.67–6.59 (1H, t, Ar), 6.35–6.25 (1H, m, Ar), 5.51–5.40 (1H, m, CHO), 3.28–3.11 (5H, m, NCH₃ and CH₂), 2.40–2.12 (2H, m, CH₂).

EXAMPLE 5

(3S)-3-(1-Indol-4-yloxy)-N-methyl-3-phenyl-1-propanamine oxalate

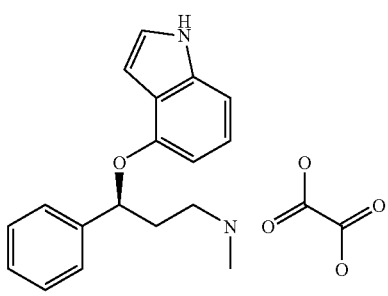

as a solid (80 mg, 59%); $\delta_H$ (300 MHz, CD₃OD) 7.45 (2H, d, Ar), 7.40–7.25 (3H, m, Ar), 7.18 (1H, d, Ar), 6.98 (1H, d, Ar), 6.85 (1H, t, Ar), 6.65 (1H, d, Ar), 6.32 (1H, d, Ar), 5.62–5.52 (1H, m, CHO), 3.40–3.20 (2H, m, CH₂), 2.75 (3H, s, NCH₃), 2.50–2.25 (2H, m, CH₂).

EXAMPLE 6

(3S)-3-(4-Fluoro-1-benzothien-7-yloxy)-N-methyl-3-phenyl-1-propanamine oxalate

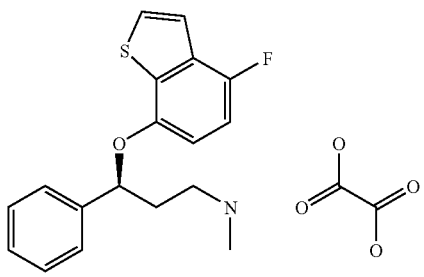

as a solid (236 mg, 77%); $\delta_H$ (300 MHz, CD₃OD) 7.68–7.21 (7H, m, Ar), 6.89–6.75 (1H, m, Ar), 6.67–6.55 (1H, m, Ar), 5.60–5.50 (1H, m, CHO), 3.38–3.12 (5H, m, NCH₃ and CH₂), 2.52–2.20 (2H, m, CH₂).

EXAMPLE 7

(3S)-3-(4-Fluoro-3-methyl-1-benzothien-7-yloxy)-N-methyl-3-phenyl-1-propanamine hydrochloride

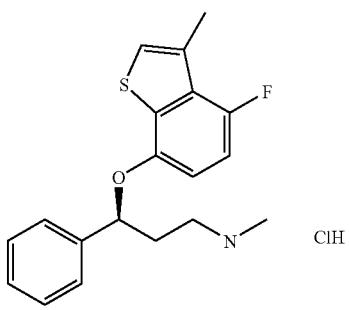

as a solid (300 mg, 92%); $\delta_H$ (300 MHz, CD₃OD) 7.35–7.00 (6H, m, Ar), 6.71–6.61 (1H, m, Ar), 6.52–6.42 (1H, dd, Ar), 5.50–5.40 (1H, m, CHO), 3.26–3.06 (5H, m, NCH₃ and CH₂), 2.45–2.15 (5H, m, CH₃ and CH₂).

EXAMPLE 8

(3S)-3-(3-Chloro-4-fluoro-1-benzothien-7-yloxy)-N-methyl-3-phenyl-1-propanamine hydrochloride

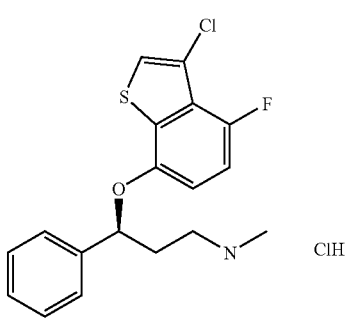

as a solid (284 mg, 60%); $\delta_H$ (300 MHz, CD₃OD) 7.40–7.00 (6H, m, Ar), 6.71–6.61 (1H, m, Ar), 6.52–6.42 (1H, dd, Ar), 5.50–5.40 (1H, m, CHO), 3.26–3.06 (5H, m, NCH₃ and CH₂), 2.45–2.15 (2H, m, CH₂).

EXAMPLE 9

(3S)-3-(4-Methyl-1-benzothien-7-yloxy)-N-methyl-3-phenyl-1-propanamine hydrochloride

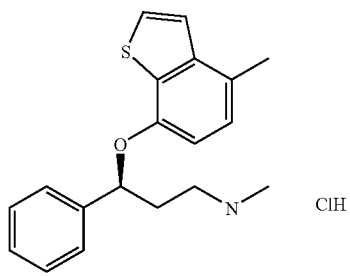

as a colourless oil (670 mg, 76%); δ$_H$ (300 MHz, CDCl$_3$) 7.45–7.15 (7H, m, Ar), 6.82 (1H, d, Ar), 6.42 (1H, d, Ar), 5.55–5.48 (1H, m, CHO), 3.20–3.12 (2H, m, CH$_2$), 2.62–2.34 (4H, m, CHH and CH$_3$ and NCH$_3$).

EXAMPLE 10

(3S)-3-(2-Fluoro-1-benzothien-7-yloxy)-N-methyl-3-phenyl-1-propanamine hydrochloride

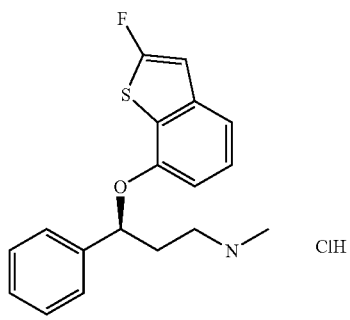

Procedure identical to above to give the title compound as a solid (220 mg, 76%); δ$_H$ (300 MHz, CD$_3$OD) 7.38–6.90 (8H, m, Ar), 6.62–6.49 (1H, m, Ar), 5.55–5.40 (1H, m, CHO), 3.29–3.16 (5H, m, NCH$_3$ and CH$_2$), 2.40–2.12 (2H, m, CH$_2$).

EXAMPLE 11

(3S)-3-(2-Fluoro-1-benzothien-4-yloxy)-N-methyl-3-phenyl-1-propanamine hydrochloride

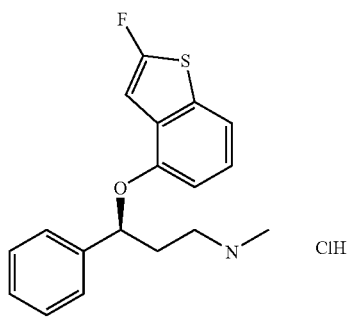

Procedure identical to above to give the title compound as a solid (108 mg, 86%); δ$_H$ (300 MHz, CDCl$_3$) 7.50–7.08 (8H, m, Ar), 6.78–6.69 (1H, m, Ar), 5.69–5.59 (1H, m, CHO), 3.35–3.15 (5H, m, NCH$_3$ and CH$_2$), 2.52–2.24 (2H, m, CH$_2$).

EXAMPLE 12

(3S)-3-(5-Fluoro-1-benzothien-7-yloxy)-N-methyl-3-phenyl-1-propanamine hydrochloride

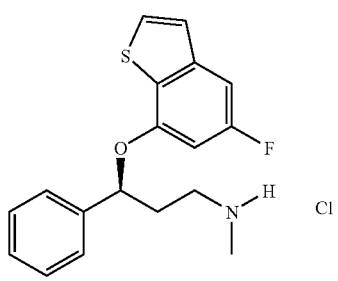

as a fluffy white solid (198 mg, 0.563 mmol, 68%); δ$_H$ (300 MHz, CDCl$_3$) 9.70 (2H, bs, NH$_2^+$Cl$^-$), 7.48 (1H, d, Ar), 7.40–7.20 (6H, m, Ar), 7.02 (1H, dd, Ar), 6.40 (1H, dd, Ar), 5.50 (1H, bd, CHO), 3.18 (2H, bd, CH$_2$), 2.60 (3H, bt, NCH$_3$), 2.50 (2H, bm, CH$_2$).

EXAMPLE 13

(3S)-3-(4-Trifluoromethyl-1-benzothien-6-yloxy)-N-methyl-3-phenyl-1-propanamine hydrochloride

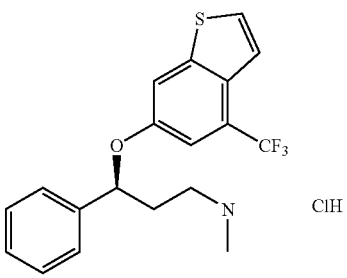

as a fluffy white solid (179 mg, 0.445 mmol, 70%); δ$_H$ (300 MHz, CDCl$_3$) 7.40–7.20 (9H, m, Ar), 5.45 (1H, m, CHO), 3.10 (2H, m, CH$_2$), 2.60 (3H, s, NCH$_3$), 2.45 (2H, m, CH$_2$).

EXAMPLE 14

(3S)-3-(5-Fluoro-1-benzothien-4-yloxy)-N-methyl-3-phenyl-1-propanamine hydrochloride

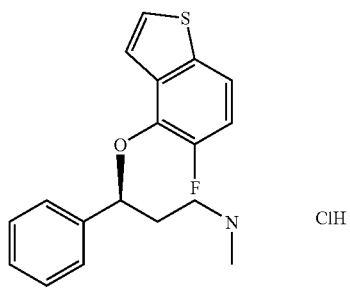

as a fluffy white solid (31 mg, 0.093 mmol, 85%); $\delta_H$ (300 MHz, CDCl$_3$) 9.90–9.30 (2H, bs, NH$_2^+$Cl$^-$), 7.40–7.15 (8H, m, Ar), 7.02 (1H, t, Ar), 5.50 (1H, m, CHO), 3.25 (2H, bm, CH$_2$), 2.68 (3H, s, NCH$_3$), 2.90–2.40 (2H, m, CH$_2$).

EXAMPLE 15

(3S)-3-[(7-Fluoro-1-benzothien-4-yl)oxy]-N-methyl-3-phenyl-1-propanamine hydrochloride

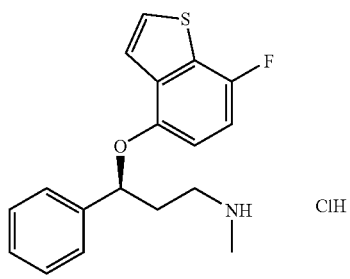

as a solid (0.24 g, 82%); $\delta_H$ (300 MHz, DMSO) 9.00 (2H, br. s, NH$_2^+$), 7.85–7.80 (1H, m, ArH), 7.75–7.68 (1H, m, ArH), 7.49–7.22 (5H, m, ArH), 7.09–6.97 (1H, m, ArH), 7.72–7.65 (1H, m, ArH), 5.72–5.62 (1H, m, CHO), 3.12–2.98 (2H, m, 1-CH$_2$), 2.56 (3H, s, NHCH$_3$), 2.43–2.27 (1H, m, 2-CHH) and 2.26–2.11 (1H, m, 2-CHH).

EXAMPLE 16

(3S)-3-[(7-Fluoro-3-methyl-1-benzothien-4-yl)oxy]-N-methyl-3-phenyl-1-propanamine hydrochloride

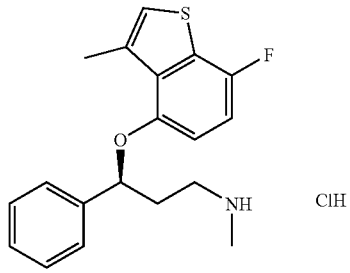

as a solid (0.14 g, 51%); $\delta_H$ (300 MHz, DMSO) 9.03 (2H, br. s, NH$_2^+$), 7.50–7.22 (6H, m, ArH), 7.01–6.91 (1H, m, ArH), 7.65–7.56 (1H, m, ArH), 5.71–5.61 (1H, m, CHO), 3.15–2.95 (2H, m, 1-CH$_2$), 2.74 (3H, s, CH$_3$), 2.58 (3H, s, NHCH$_3$), 2.45–2.28 (1H, m, 2-CHH) and 2.27–2.11 (1H, m, 2-CHH).

EXAMPLE 16A (3S)-3-(4-Cyano-1-benzo[b]thien-7-yloxy)-N-methyl-3-phenyl-1-propnamine hydrochloride

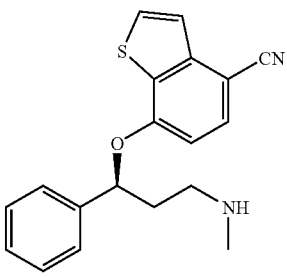

$\delta_H$ (400 MHz, DMSO-D$_6$) 8.93 (2H, br s), 8.11 (1H, d, J=6 Hz), 7.80 (1H, d, J=8 Hz), 7.52 (1H, d, J=6 Hz), 7.27–7.48 (5H, m), 6.93 (1H, d, J=8 Hz), 5.95 (1H, br, m), 2.96–3.10 (2H, m), 2.55 (3H, s), 2.36–2.45 (1H, m), 2.18–2.30 (1H, m).

EXAMPLE 17

(3S)-3-[(1-Benzothien-2-carbonitrile-7-yl)oxy]-N-methyl-3-phenyl-1-propanamine fumarate

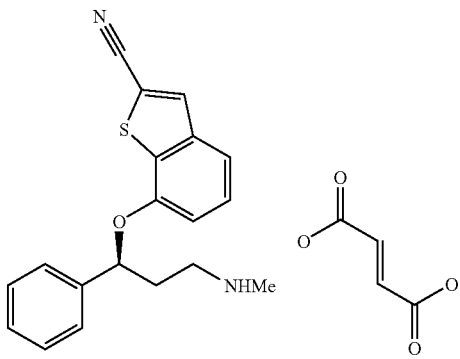

To a solution of 7-{[(1S)-3-iodo-1-phenylpropyl]oxy}-1-benzothiophene-2-carbonitrile (222 mg, 0.5 mmol) in tetrahydrofuran (2 mL) was added 40% aqueous methylamine (0.83 mL) and the solution was stirred at room temperature for 16 hours. The solvent removed in vacuo and the residue purified by flash chromatography with a gradient of 0–15% methanol in dichloromethane. To a solution of free base (155 mg, 0.48 mmol) in methanol (1 mL) and added a warm solution of fumaric acid (40 mg, 0.48 mmol) in methanol (1 mL). The solvent removed in vacuo, and the solid residue triturated with diethyl ether (5 mL), then dried in a vacuum oven at 40° C. for 1 h to give the title compound (0.20 g, 85%); $\delta_H$ (300 MHz, DMSO) 8.40 (1H, s, 3-ArH), 7.61–7.52 (1H, m, ArH), 7.49–7.23 (6H, m, ArH), 7.05–6.98 (1H, m, ArH), 6.43 (2H, s, CHCO$_2$H), 5.85–5.75 (1H, m, CHO), 3.05–2.90 (2H, m, 1-CH$_2$), 2.52 (3H, s, NHCH$_3$) and 2.46–2.07 (2H, m, 2-CH$_2$).

Similarly prepared was

EXAMPLE 18

(3S)-3-[(1-Benzothien-2-carbonitrile-4-yl)oxy]-N-methyl-3-phenyl-1-propanamine fumarate

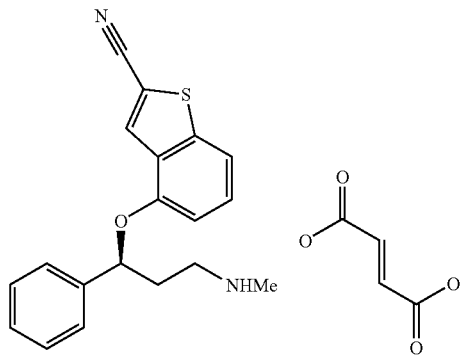

as a solid (0.15 g, 79%); $\delta_H$ (300 MHz, DMSO) 8.57 (1H, s, 3-ArH), 7.65–7.60 (1H, m, ArH), 7.49–7.23 (6H, m, ArH), 6.82–6.72 (1H, m, ArH), 6.60 (2H, s, CHCO$_2$H), 5.76–5.66 (1H, m, CHO), 3.18–3.02 (2H, m, 1-CH$_2$), 2.62 (3H, s, NHCH$_3$), and 2.39–2.10 (2H, m, 2-CH$_2$).

EXAMPLE 19

(3S)-3-[(4-Fluoro-1-benzothien-2-carbonitrile-7-yl)oxy]-N-methyl-3-phenyl-1-propanamine

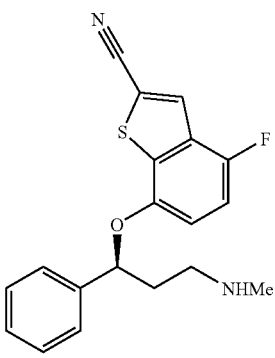

4,4-(Dimethyl-1,1-dioxido-1,2,5-thiadiazolidin-2-yl)-triphenyl phosphonium (383 mg, 0.93 mmol) was added in one portion to a stirred solution of (R)-3-iodo-1-phenyl-1-propanol[1] (182 mg, 0.69 mmol) and 4-fluoro-7-hydroxy-benzothiophene-2-carbonitrile (112 mg, 0.58 mmol) in dry THF (12 mL) under an inert atmosphere on nitrogen. The resulting suspension was allowed to stir for a further 18 hrs before the solvent was removed in vacuo. The residue was purified by flash chromatography with a gradient of 0–4% diethyl ether in hexane to give the title compound as a colourless oil (0.22 g, 88%); $\delta_H$ (300 MHz, CDCl$_3$) 7.83 (1H, s, 3-ArH), 7.36–7.12 (5H, m, ArH), 6.85–6.75 (1H, m, ArH), 6.65–6.57 (1H, m, ArH), 5.40–5.30 (1H, m, HO), 3.47–3.28 (1H, m, CH$_2$CHHI), 3.23–3.12 (1H, m, CH$_2$CHHI), 2.60–2.42 (1H, m, CHHCH$_2$I) and 2.34–2.19 (1H, m, CHHCH$_2$I).

Similarly prepared were

EXAMPLE 20

(3S)-3-[(1-Benzothien-2-carbonitrile-6-yl)oxy]-N-methyl-3-phenyl-1-propanamine difumarate

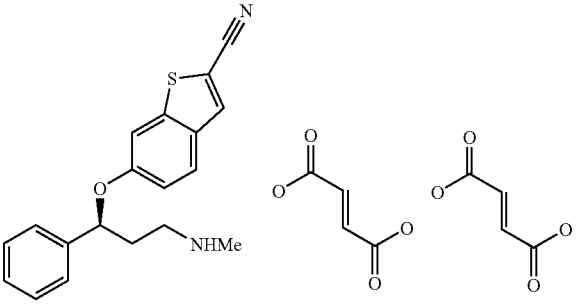

as a solid (0.75 g, 19%); $\delta_H$ (300 MHz, DMSO) 8.25 (1H, s, 3-ArH), 7.92–7.88 (1H, m, ArH), 7.62 (1H, s, 7-ArH), 7.49–7.15 (6H, m, ArH), 6.62 (4H, s, CHCO$_2$H), 5.67–5.59 (1H, m, CHO), 3.15–2.99 (2H, m, 1-CH$_2$), 2.61 (3H, s, NHCH$_3$) and 2.38–2.09 (2H, m, 2-CH$_2$).

EXAMPLE 21

(3S)-3-[(6-Fluoro-1-benzothien-7-yl)oxy]-N-methyl-3-phenyl-1-propanamine hydrochloride

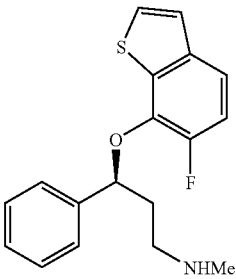

as a solid (0.11 g, 65%); $\delta_H$ (300 MHz, CDCl$_3$) 8.98–8.71 (1H, m, NH), 8.62–8.39 (1H, m, NH), 7.48–7.02 (9H, m, ArH), 5.65–5.59 (1H, m, CHO), 3.52–3.38 (2H, m, 1-CH$_2$), 2.94–2.78 (1H, m, 2-CHH), 2.74 (3H, m, NHCH$_3$) and 2.62–2.48 (1H, m, 2-CHH).

EXAMPLE 22

1-Methyl-[3S-(1-methyl-1H-indol-5-yloxy)-3-phenyl-propyl]-amine hydrochloride

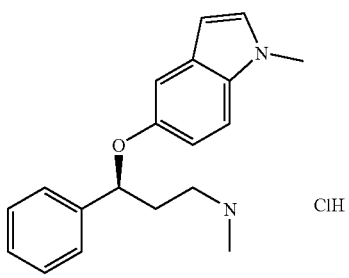

as a fluffy white solid (23 mg, 25%); Melting point of title compound: 161.8° C.

EXAMPLE 23

N-Methyl-[3S-(1-methyl-1H-indol-7-yloxy)-3-phenyl-propyl]-amine hydrochloride

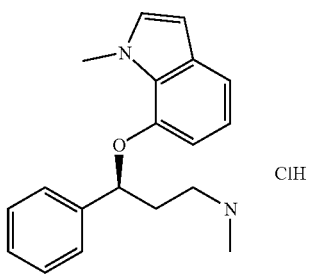

as a solid (108 mg, 32%); Melting point of title compound: 216.4° C.

EXAMPLE 24

(3S)-3-(1-Benzothien-7-yloxy)-3-phenyl-1-propanamine oxalate

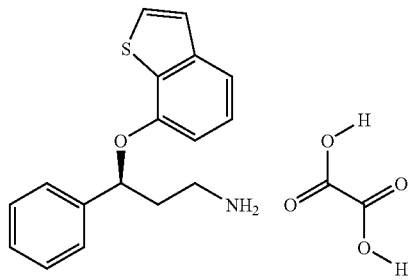

Ammonia (0.88M, 5 mL) was dissolved in a solution of 7-[(1S)-3-chloro-1-phenylpropyl]oxy-1-benzothiophene (280 mg, 0.927 mmol) in ethanol (abs, 4 mL), the resulting solution was heated to 130° C. in a sealed bomb for 3 h. After this time the reaction was allowed to cool to room temperature before the solvent was removed in vacuo. The residue was purified by flash chromatography eluting silica gel with CHCl$_3$:MeOH [10:1] to yield a colourless oil.

The resulting oil was dissolved in ethyl acetate (5 mL) and a solution of oxalic acid (62 mg, 0.695 mmol) in ethyl acetate (5 mL) added. The mixture was stirred at room temperature for 10 mins and then the solvent removed in vacuo. The residue was dissolved in acetonitrile (1 mL) and water (5 mL), this solution was then frozen by immersion in a dry ice:acetone bath, the resulting frozen material was freeze dried overnight to yield the target compound as a fluffy white solid (220 mg); δ$_H$ (300 MHz, DMSO) 7.60–7.15 (9H, m, Ar), 6.65 (1H, d, Ar), 5.62 (1H, m, CHOH), 3.20 (2H, m, CH$_2$), 2.38 (2H, m, CH$_2$).

Similarly prepared was

EXAMPLE 25

(3S)-3-(4-Fluoro-1-benzothien-7-yloxy)-3-phenyl-1-propanamine oxalate

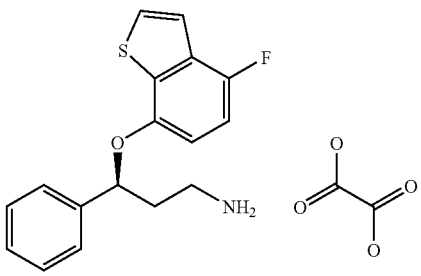

Procedure identical to above to give the title compound as a solid (218 mg, 66%); δ$_H$ (300 MHz, CDCl$_3$) 7.71–7.21 (7H, m, Ar), 6.89–6.75 (1H, m, Ar), 6.67–6.55 (1H, m, Ar), 5.63–5.56 (1H, m, CHO), 3.44–3.17 (2H, m, CH$_2$), 2.55–2.23 (2H, m, CH$_2$).

EXAMPLE 26

(3S)-3-(-1-Benzothien-7-yloxy)-N-methyl-3-(2-thienyl)-1-propanamine oxalate

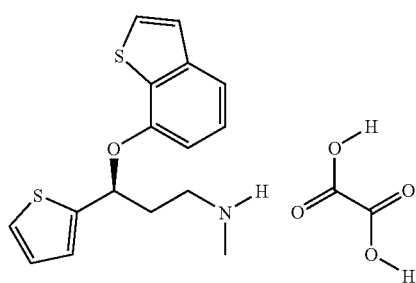

Methylamine (40% in water, 4 mL) was dissolved in a solution of 7-{[(1S)-3-chloro-1-(2-thienyl)propyl]oxy}-1-benzothiophene (350 mg, 0.113 mmol) in ethanol (abs, 4 mL), the resulting solution was heated to 130° C. in a sealed bomb for 3 hrs. After this time the reaction was allowed to cool to room temperature before the solvent was removed in vacuo. The residue was purified by flash chromatography eluting silica gel with CHCl$_3$:Methanol [10:1] to yield a colourless oil.

The resulting oil was dissolved in ethyl acetate (3 mL) and a solution of oxalic acid (6 mg, 0.048 mmol) in ethyl acetate 2 mL) added. The mixture was stirred at room temperature for 10 mins and then the solvent removed in vacuo. The residue was dissolved in acetonitrile (1 mL) and water (5 mL), this solution was then frozen by immersion in a dry ice:acetone bath, the resulting frozen material was freeze dried overnight to yield the target compound as a fluffy white solid (26 mg); δ$_H$ (300 MHz, CDCl$_3$) 7.55 (1H, d, Ar), 7.38–6.80 (7H, m, Ar) 5.85–5.60 (1H, m, CHO), 3.02 (2H, m, CH$_2$), 2.50 (3H, s, CH$_3$), 2.45–2.28 (2H, m, CH$_2$).

EXAMPLE 27

(3R)-3-(1-Benzothien-7-yloxy)-N-methyl-3-phenyl-1-propanamine oxalate

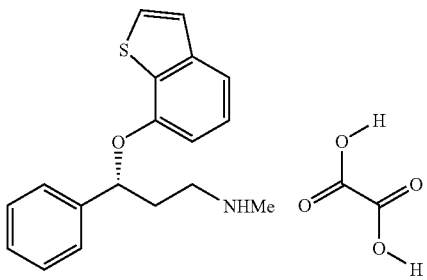

Methylamine (40% in water, 4 mL) was dissolved in a solution of 7-[(1R)-3-chloro-1-phenylpropyl]oxy-1-benzothiophene (240 mg, 0.79 mmol) in ethanol (abs, 4 mL), the resulting solution was heated to 130° C. in a sealed bomb for 3 h. After this time the reaction was allowed to cool to room temperature before the solvent was removed in vacuo. The residue was purified by flash chromatography eluting silica gel with CHCl₃:Methanol [10:1] to yield a colourless oil.

The resulting oil was dissolved in ethyl acetate (10 mL) and a solution of oxalic acid (93 mg, 0.75 mmol) in ethyl acetate (5 mL) added. The mixture was stirred at room temperature for 10 mins and then the solvent removed in vacuo. The residue was dissolved in acetonitrile (3 mL) and water (25 mL), this solution was then frozen by immersion in a dry ice:acetone bath, the resulting frozen material was freeze dried overnight to yield the target compound as a fluffy white solid (315 mg); $\delta_H$ (300 MHz, CDCl₃) 7.50–7.25 (8H, m, Ar), 7.15 (1H, t, Ar), 6.55 (1H, d, Ar), 5.50 (1H, bd, CHO), 3.70 (3H, s, NCH₃), 3.22 (2H, m, CH₂), 2.42 (2H, m, CH₂).

Similarly prepared were

EXAMPLE 28

(3R)-3-(1-Benzothien-4-yloxy)-N-methyl-3-phenyl-1-propanamine oxalate

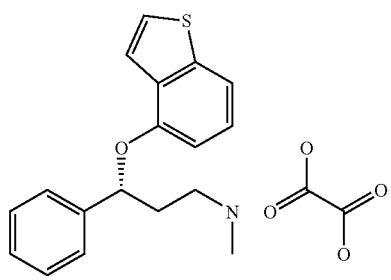

as a solid (104 mg, 90%); $\delta_H$ (300 MHz, CD₃OD) 7.50–7.25 (8H, m, Ar), 7.15 (1H, t, Ar), 6.55 (1H, d, Ar), 5.62–5.44 (1H, m, CHO), 3.70 (3H, s, NCH₃), 3.36–3.21 (2H, m, CH₂), 2.50–2.36 (2H, m, CH₂).

EXAMPLE 29

(3R)-3-(1-Benzothien-5-yloxy)-N-methyl-3-phenyl-1-propanamine oxalate

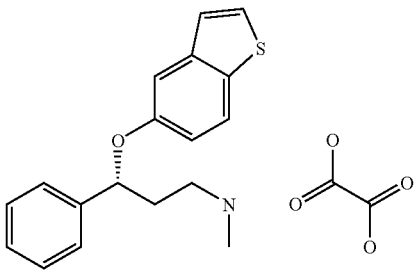

as a solid (500 mg, 93%); $\delta_H$ (300 MHz, CD₃OD) 8.00–7.91 (1H, d, Ar), 7.70–7.22 (9H, m, Ar), 5.70–5.60 (1H, m, CHO), 3.58 (3H, s, NCH₃), 3.56–3.38 (2H, m, CH₂), 2.52–2.36 (2H, m, CH₂).

EXAMPLE 29A (3R)-3-(1-Benzothien-6-yloxy)-N-methyl-3-phenyl-1-propanamine hydrochloride

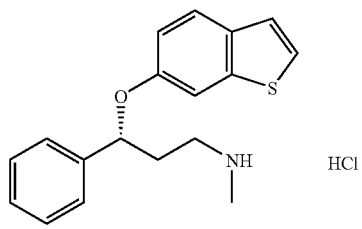

as a solid (188 mg, 52%); $\delta_H$ (400 MHz, CDCl₃) 7.61 (1H, d, J=8.0 Hz, Ar), 7.39–7.16 (8H, m, Ar), 6.98 (1H, dd, J=4, 8 Hz, Ar), 5.30 (1H, dd, J=5, 8 Hz, CHO), 2.81–2.78 (2H, m, CH₂), 2.45 (3H, s, NCH₃), 2.26–2.20 (1H, m, CH H), 2.08–2.03 (1H, m, CH H).

EXAMPLE 30

(3R)-3-(1-Indol-7-yloxy)-N-methyl-3-phenyl-1-propanamine oxalate

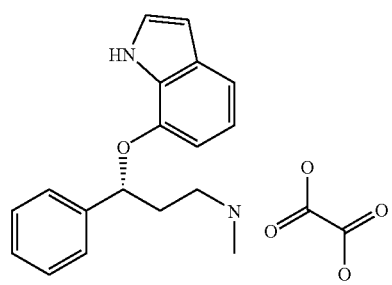

as a solid (48 mg, 22%); $\delta_H$ (300 MHz, CD$_3$OD) 7.40–6.92 (8H, m, Ar), 6.67–6.59 (1H, t, Ar), 6.35–6.25 (1H, m, Ar), 5.51–5.40 (1H, m, CHO), 3.28–3.11 (5H, m, NCH$_3$ and CH$_2$), 2.40–2.12 (2H, m, CH$_2$).

EXAMPLE 31

(3R)-3-(1-Indol-4-yloxy)-N-methyl-3-phenyl-1-propanamine oxalate

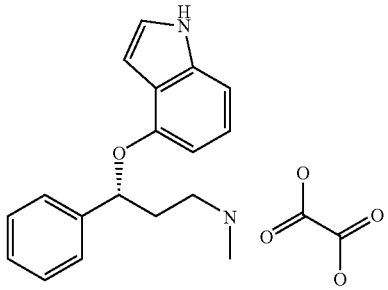

as a solid (50 mg, 39%); $\delta_H$ (300 MHz, CD$_3$OD) 7.45 (2H, d, Ar), 7.40–7.25 (3H, m, Ar), 7.18 (1H, d, Ar), 6.98 (1H, d, Ar), 6.85 (1H, t, Ar), 6.65 (1H, d, Ar), 6.32 (1H, d, Ar), 5.62–5.52 (1H, m, CHO), 3.40–3.20 (2H, m, CH$_2$), 2.75 (3H, s, NCH$_3$), 2.50–2.25 (2H, m, CH$_2$).

EXAMPLE 32

(3R)-3-(4-Fluoro-1-benzothien-7-yloxy)-N-methyl-3-phenyl-1-propanamine oxalate

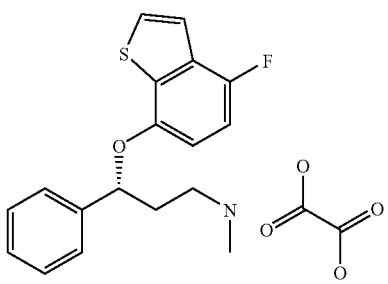

as a solid (419 mg, 96%); $\delta_H$ (300 MHz, CD$_3$OD) 7.68–7.21 (7H, m, Ar), 6.89–6.75 (1H, m, Ar), 6.67–6.55 (1H, m, Ar), 5.60–5.50 (1H, m, CHO), 3.38–3.12 (5H, m, NCH$_3$ and CH$_2$), 2.52–2.20 (2H, m, CH$_2$).

EXAMPLE 33

(3R)-3-(4-Fluoro-3-methyl-1-benzothien-7-yloxy)-N-methyl-3-phenyl-1-propanamine hydrochloride

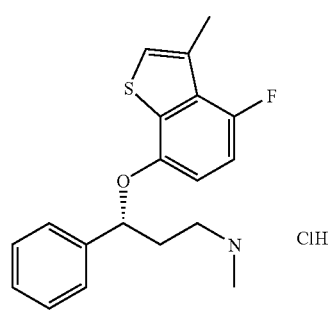

as a solid (200 mg, (80%); $\delta_H$ (300 MHz, CD$_3$OD) 7.35–7.00 (6H, m, Ar), 6.71–6.61 (1H, m, Ar), 6.52–6.42 (1H, dd, Ar), 5.50–5.40 (1H, m, CHO), 3.26–3.06 (5H, m, NCH$_3$ and CH$_2$), 2.45–2.15 (5H, m, CH$_3$ and CH$_2$).

EXAMPLE 34

(3R)-3-(3-Chloro-4-fluoro-1-benzothien-7-yloxy)-N-methyl-3-phenyl-1-propanamine hydrochloride

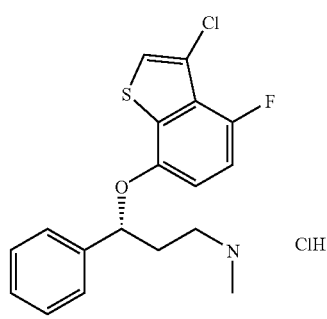

as a solid (340 mg, 71%); $\delta_H$ (300 MHz, CD$_3$OD) 7.40–7.00 (6H, m, Ar), 6.71–6.61 (1H, m, Ar), 6.52–6.42 (1H, dd, Ar), 5.50–5.40 (1H, m, CHO), 3.26–3.06 (5H, m, NCH$_3$ and CH$_2$), 2.45–2.15 (2H, m, CH$_2$).

EXAMPLE 35

(3R)-3-(4-Methyl-1-benzothien-7-yloxy)-N-methyl-3-phenyl-1-propanamine hydrochloride

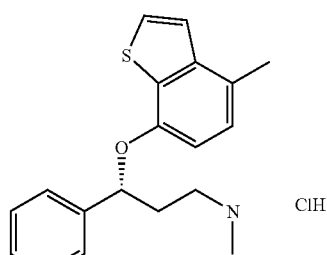

as a colourless oil (824 mg, 93%); $\delta_H$ (300 MHz, CDCl$_3$) 7.45–7.15 (7H, m, Ar), 6.82 (1H, d, Ar), 6.42 (1H, d, Ar), 5.55–5.48 (1H, m, CHO), 3.20–3.12 (2H, m, CH$_2$), 2.62–2.34 (4H, m, CHH and CH$_3$ and NCH$_3$).

EXAMPLE 36

(3R)-3-(2-Fluoro-1-benzothien-7-yloxy)-N-methyl-3-phenyl-1-propanamine hydrochloride

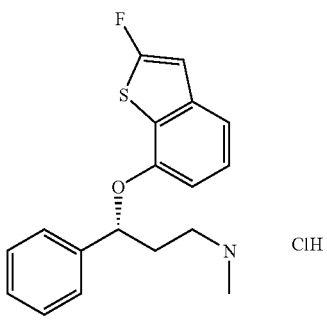

as a solid (270 mg, 80%); $\delta_H$ (300 MHz, CD$_3$OD) 7.38–6.90 (8H, m, Ar), 6.62–6.49 (1H, m, Ar), 5.55–5.40 (1H, m, CHO), 3.29–3.16 (5H, m, NCH$_3$ and CH$_2$), 2.40–2.12 (2H, m, CH$_2$).

EXAMPLE 37

(3R)-3-(2-Fluoro-1-benzothien-4-yloxy)-N-methyl-3-phenyl-1-propanamine hydrochloride

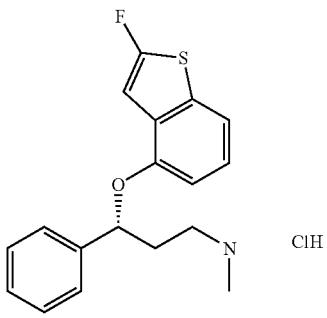

as a solid (97 mg, 60%); $\delta_H$ (300 MHz, CD$_3$OD) 7.50–7.08 (8H, m, Ar), 6.78–6.69 (1H, m, Ar), 5.69–5.59 (1H, m, CHO), 3.35–3.15 (5H, m, NCH$_3$ and CH$_2$), 2.52–2.24 (2H, m, CH$_2$).

EXAMPLE 38

(3R)-3-(5-Fluoro-1-benzothien-7-yloxy)-N-methyl-3-phenyl-1-propanamine hydrochloride

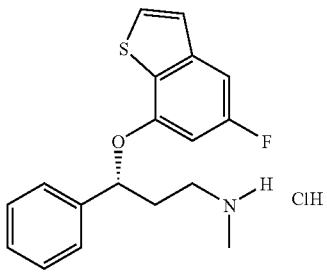

as a fluffy white solid (165 mg, 60%); $\delta_H$ (300 MHz, CDCl$_3$) 9.70 (2H, bs, NH$_2^{+Cl-}$), 7.48 (1H, d, Ar), 7.40–7.20 (6H, m, Ar), 7.02 (1H, dd, Ar), 6.40 (1H, dd, Ar), 5.50 (1H, bd, CHO), 3.18 (2H, bd, CH$_2$), 2.60 (3H, bt, NCH$_3$), 2.50 (2H, bm, CH$_2$).

EXAMPLE 39

(3R)-3-(4-Trifluoromethyl-1-benzothien-6-yloxy)-N-methyl-3-phenyl-1-propanamine hydrochloride

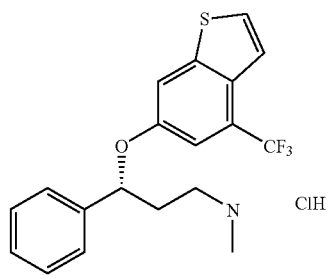

as a fluffy white solid (184 mg, 62%); $\delta_H$ (300 MHz, CDCl$_3$) 7.40–7.20 (9H, m, Ar), 5.45 (1H, m, CHO), 3.10 (2H, m, CH$_2$), 2.60 (3H, s, NCH$_3$), 2.45 (2H, m, CH$_2$).

EXAMPLE 40

(3R)-3-(5-Fluoro-1-benzothien-4-yloxy)-N-methyl-3-phenyl-1-propanamine hydrochloride

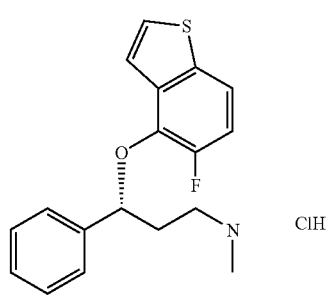

as a fluffy white solid (37 mg, 89%); $\delta_H$ (300 MHz, CDCl$_3$) 8.30 (1H, bs, NH), 7.40–7.15 (8H, m, Ar), 7.02 (1H, t, Ar), 5.50 (1H, m, CHO), 3.25 (2H, bm, CH$_2$), 2.68 (3H, s, NCH$_3$), 2.80–2.35 (2H, m, CH$_2$).

EXAMPLE 41

(3R)-3-[(7-Fluoro-1-benzothien-4-yl)oxy]-N-methyl-3-phenyl-1-propanamine hydrochloride

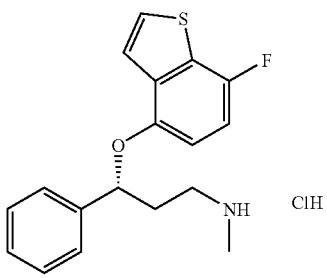

as a solid (0.20 g, 40%); $\delta_H$ (300 MHz, DMSO) 8.95 (2H, br. s, NH$_2^+$), 7.85–7.80 (1H, m, ArH), 7.75–7.68 (1H, m, ArH), 7.49–7.22 (5H, m, ArH), 7.09–6.97 (1H, m, ArH), 7.72–7.65 (1H, m, ArH), 5.72–5.62 (1H, m, CHO), 3.12–2.98 (2H, m, 1-CH$_2$), 2.56 (3H, s, NHCH$_3$), 2.43–2.27 (1H, m, 2-CHH) and 2.26–2.11 (1H, m, 2-CHH).

EXAMPLE 41A (3R)-3-[(7-Fluoro-3-methyl-1-benzothien-4-yl)oxy]-N-methyl-3-phenyl-1-propanamine hydrochloride

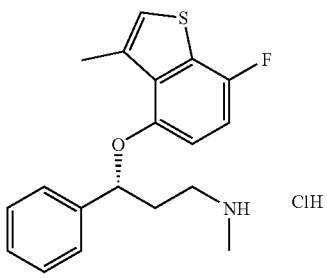

as a solid (0.20 g, 55%); $\delta_H$ (300 MHz, DMSO) 8.90 (2H, br. s, NH$_2^+$), 7.50–7.22 (6H, m, ArH), 7.01–6.91 (1H, m, ArH), 7.65–7.56 (1H, m, ArH), 5.71–5.61 (1H, m, CHO), 3.15–2.95 (2H, m, 1-CH$_2$), 2.74 (3H, s, CH$_3$), 2.58 (3H, s, NHCH$_3$), 2.45–2.28 (1H, m, 2-CHH) and 2.27–2.11 (1H, m, 2-CHH).

EXAMPLE 41B (3R)-3-(4-Cyano-1-benzo[b]thien-7-yloxy)-N-methyl-3-phenyl-1-propanamine hydrochloride

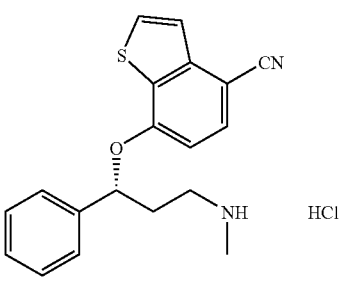

$\delta_H$ (400 MHz, DMSO-D$_6$) 8.93 (2H, br s), 8.11 (1H, d, J=6 Hz), 7.80 (1H, d, J=8 Hz), 7.52 (1H, d, J=6 Hz), 7.27–7.48 (5H, m), 6.93 (1H, d, J=8 Hz), 5.95 (1H, br m), 2.96–3.10 (2H, m), 2.55 (3H, s), 2.36–2.45 (1H, m), 2.18–2.30 (1H, m).

EXAMPLE 42

(3R)-3-[(1-Benzothien-2-carbonitrile-7-yl)oxy]-N-methyl-3-phenyl-1-propanamine fumarate

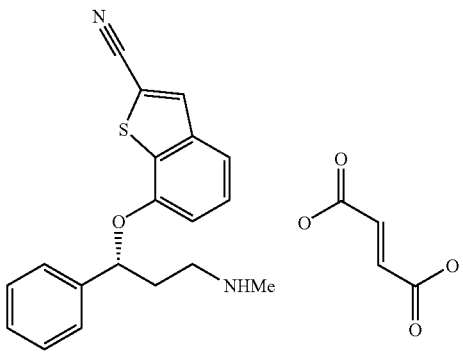

To a solution of 7-{[(1R)-3-iodo-1-phenylpropyl]oxy}-1-benzothiophene-2-carbonitrile (156 mg, 0.37 mmol) in tetrahydrofuran (1.5 mL) was added 40% aqueous methylamine (0.5 mL) and the solution was stirred at room temperature for 16 hours. The solvent removed in vacuo and the residue purified by flash chromatography with a gradient of 0–15% methanol in dichloromethane. To a solution of free base (96 mg, 0.3 mmol) in methanol (1 mL) and added a warm solution of fumaric acid (26 mg, 0.3 mmol) in methanol (1 mL). The solvent removed in vacuo, and the solid residue triturated with ether (5 mL), then dried in a vacuum oven at 40° C. for 1 hour to give the title compound (120 mg, 74%); $\delta_H$ (300 MHz, DMSO) 8.40 (1H, s, 3-ArH), 7.61–7.52 (1H, m, ArH), 7.49–7.23 (6H, m, ArH), 7.05–6.98 (1H, m, ArH), 6.45 (2H, s, CHCO$_2$H), 5.85–5.75 (1H, m, CHO), 3.05–2.90 (2H, m, 1-CH$_2$), 2.52 (3H, s, NHCH$_3$) and 2.46–2.07 (2H, m, 2-CH$_2$).

Similarly prepared were

EXAMPLE 43

(3R)-3-[(1-Benzothien-2-carbonitrile-4-yl)oxy]-N-methyl-3-phenyl-1-propanamine fumarate

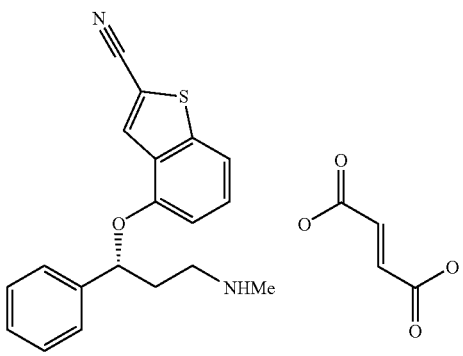

as a solid (0.17 g, 85%); δ$_H$ (300 MHz, DMSO) 8.57 (1H, s, 3-ArH), 7.65–7.60 (1H, m, ArH), 7.49–7.23 (6H, m, ArH), 6.82–6.72 (1H, m, ArH), 6.60 (2H, s, CHCO$_2$H), 5.76–5.66 (1H, m, CHO), 3.18–3.02 (2H, m, 1-CH$_2$), 2.62 (3H, s, NHCH$_3$), and 2.39–2.10 (2H, m, 2-CH$_2$).

EXAMPLE 44

(3R)-3-[(4-Fluoro-1-benzothien-2-carbonitrile-7-yl)oxy]-N-methyl-3-phenyl-1-propanamine fumarate

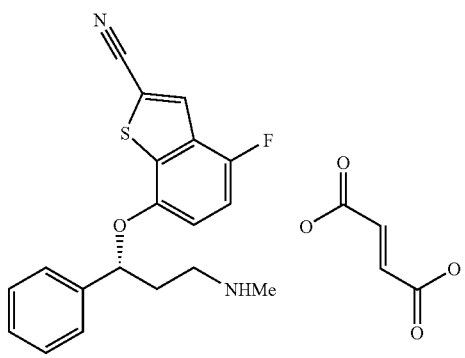

as a solid (0.57 g, 22%); δ$_H$ (300 MHz, DMSO) 8.51–8.42 (1H, m, 3-ArH), 7.49–6.90 (7H, m, ArH), 6.52–6.41 (2H, s, CHCO$_2$H), 3.10–2.87 (2H, m, 1-CH$_2$) and 2.62–2.07 (5H, m, NHCH$_3$ and 2-CH$_2$).

EXAMPLE 45

(3R)-3-[(1-Benzothien-2-carbonitrile-6-yl)oxy]-N-methyl-3-phenyl-1-propanamine difumarate

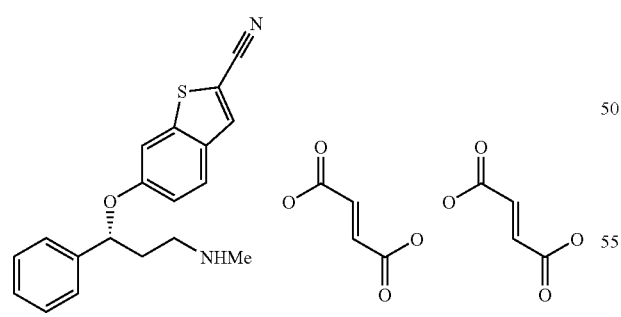

as a solid (0.78 g, 26%); δ$_H$ (300 MHz, DMSO) 13.12 (8H, br. s, CO$_2$H), 8.24 (1H, s, 3-ArH), 7.92–7.88 (1H, m, ArH), 7.61 (1H, s, 7-ArH), 7.49–7.15 (6H, m, ArH), 6.62 (4H, s, CHCO$_2$H), 5.66–5.58 (1H, m, CHO), 3.15–2.97 (2H, m, 1-CH$_2$), 2.60 (3H, s; NHCH$_3$) and 2.38–2.05 (2H, m, 2-CH$_2$).

EXAMPLE 46

(3R)-3-[(6-Fluoro-1-benzothien-7-yl)oxy]-N-methyl-3-phenyl-1-propanamine hydrochloride

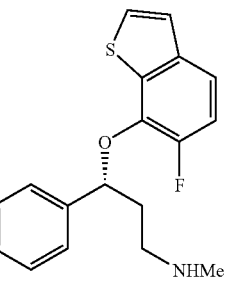

as a solid (0.14 g, 90%); δ$_H$ (300 MHz, CDCl$_3$) 9.02–8.73 (1H, m, NH), 8.62–8.35 (1H, m, NH), 7.45–7.00 (9H, m, ArH), 5.62–5.54 (1H, m, CHO), 3.52–3.34 (2H, m, 1-CH$_2$), 2.94–2.78 (1H, m, 2-CHH), 2.73 (3H, m, NHCH$_3$) and 2.60–2.45 (1H, m, 2-CHH).

EXAMPLE 47

1-Methyl-[3R-(1-methyl-1H-indol-5-yloxy)-3-phenyl-propyl]amine hydrochloride

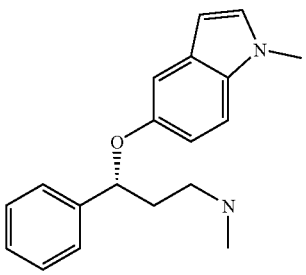

as a solid (46 mg, 19%); Melting point: 95.4° C.

EXAMPLE 48

[3R-(Benzofuran-4-yloxy)-3-phenyl-propyl]-N-methylamine hydrochloride

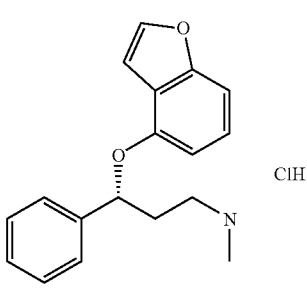

4,4-(Dimethyl-1,1-dioxido-1,2,5-thiadiazolidin-2-yl)-triphenyl phosphonium (800 mg, 2.03 mmol) was added in one portion to a stirred solution of (S)-(−)-3-iodo-1-phenyl-1-propanol (670 mg, 2.5 mmol) and benzofuran-4-ol (*Synth Commun*, 16 (13) pg. 1635–40, 1986) (228 mg, 1.7 mmol) in dry THF (5 mL) under an inert atmosphere of nitrogen. The resulting suspension was allowed to stir for a further 24 h while heating at 40° C. before the solvent was removed in vacuo. The residue was taken up in $CH_2Cl_2$ and washed with 0.5 N NaOH. The organic phase was dried ($MgSO_4$) and concentrated in vacuo. The residue was purified by flash chromatography eluting silica gel with hexane:ethyl acetate [100:0 to 3:1] to yield the iodo compound (291 mg, 45%); Mass spectrum (ion spray): m/z=379.1 (M+1)

The iodo compound was directly placed, without further purification, in a solution of methylamine (2M in THF, 15 mL). The resulting solution was heated to 40° C. in a sealed tube for 4 h. After this time the reaction was allowed to cool to room temperature before the solvent was removed in vacuo. The residue was purified by flash chromatography eluting silica gel with $CH_2Cl_2$:MeOH (2M $NH_3$) [100:0 to 5:1] to yield the hydroiodide salt of the title compound. This white solid was dissolved in $CH_2Cl_2$ and washed with 0.5 N NaOH. The aqueous phase was extracted 2 times with a solution of 3:1 $CHCl_3$:IPA. The combined organic phase was dried ($MgSO_4$), filtered and concentrated in vacuo to yield the free base of the title compound (104.7 mg, 86%). The residue was placed in MeOH (5 mL) and $NH_4Cl$ (19.9 mg) was added. The mixture was sonicated at room temperature for 10 min and then the solvent removed in vacuo. The residue was dissolved in MeCN (0.5 mL) and water (1 mL), this solution was then frozen by immersion in a dry ice: acetone bath, the resulting frozen material was freeze dried overnight to yield the target compound as a fluffy white solid (23 mg); Melting point of title compound: 140.5° C.

Similarly prepared was

EXAMPLE 49

[3S-(Benzofuran-4-yloxy)-3-phenyl-propyl]-N-methylamine hydrochloride

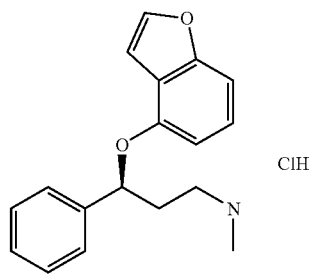

A method similar to Example 3b, using (R)-(+)-3-iodo-1-phenyl-1-propanol gave the title compound (111.4 mg, 77.5%); Melting point: 138.2° C.

EXAMPLE 50

[3S-(Benzofuran-7-yloxy)-3-phenyl-propyl]-methylamine hydrochloride

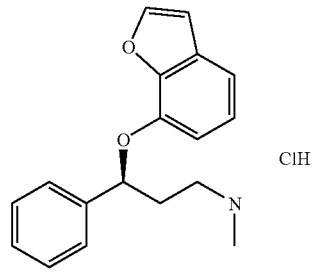

Methylamine (40% in water) (10 mL) was added to a solution of 7-[(1S)-3-iodo-1-phenyl-propoxy)-benzofuran (1.00 g, 2.6 mmol) in EtOH (8 mL), the resulting solution was heated to 110° C. in a sealed tube for 3 h. After this time the reaction was allowed to cool to room temperature and diluted with $CH_2Cl_2$ and washed with 0.5 N NaOH. The aqueous phase was extracted 2 times with a solution of 3:1 $CHCl_3$:IPA. The combined organic solution was dried ($MgSO_4$) and concentrated in vacuo. The residue was purified by flash chromatography eluting silica gel with $CH_2Cl_2$: MeOH (2M $NH_3$) [100:0 to 3:1] to yield the free-base of the title compound (340 mg, 46%). The resulting residue was dissolved in MeOH (5 mL) and $NH_4Cl$ (64.6 mg) was added. The mixture was sonicated at room temperature for 10 mins and then the solvent removed in vacuo. The residue was dissolved in MeCN (0.5 mL) and water (1 mL), this solution was then frozen by immersion in a dry ice: acetone bath, the resulting frozen material was freeze dried overnight to yield the target compound as a fluffy white solid; Melting Point of title compound: 60.1° C.

EXAMPLE 51

[3R-(Benzofuran-7-yloxy)-3-phenyl-propyl]-methylamine hydrochloride

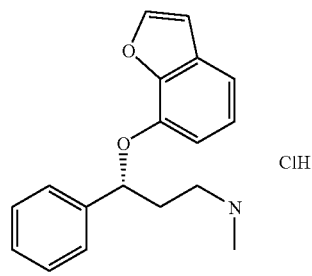

as a soluid (335 mg, 42%); Melting point of title compound: 55.7° C.

EXAMPLE 52

(3R)-3-(1-Benzothien-7-yloxy)-3-phenyl-1-propanamine oxalate

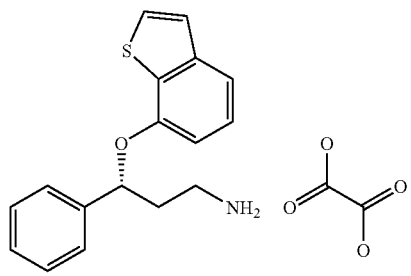

Ammonia (0.880, 4 mL) was dissolved in a solution of 7-[(1R)-3-chloro-1-phenylpropyl]oxy-1-benzothiophene (240 mg, 0.79 mmol) in ethanol (abs, 4 mL), the resulting solution was heated to 130° C. in a sealed bomb for 3 h. After this time the reaction was allowed to cool to room temperature before the solvent was removed in vacuo. The residue was purified by flash chromatography eluting silica gel with $CHCl_3$:MeOH [10:1] to yield a colourless oil.

The resulting oil was dissolved in ethyl acetate (10 mL) and a solution of oxalic acid (93 mg, 0.75 mmol) in ethyl acetate (5 mL) added. The mixture was stirred at room temperature for 10 mins and then the solvent evaporated in vacuo. The residue was dissolved in acetonitrile (3 mL) and water (25 mL), this solution was then frozen by immersion in a dry ice:acetone bath, the resulting frozen material was freeze dried overnight to yield the target compound as a fluffy white solid (315 mg); $\delta_H$ (300 MHz, $CDCl_3$) 7.50–7.25 (8H, m, Ar), 7.15 (1H, t, Ar), 6.55 (1H, d, Ar), 5.50 (1H, bd, CHO), 3.30–3.20 (2H, m, $CH_2$), 2.48–2.40 (2H, m, $CH_2$).

Similarly prepared was

EXAMPLE 53

(3R)-3-(4-Fluoro-1-benzothien-7-yloxy)-3-phenyl-1-propanamine oxalate

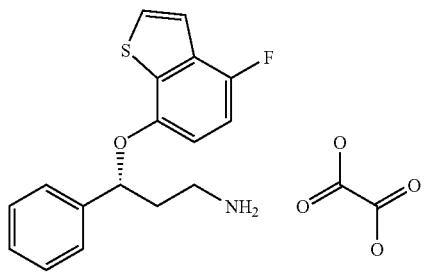

as a solid (296 mg, 60%); $\delta_H$ (300 MHz, $CDCl_3$) 7.71–7.21 (7H, m, Ar), 6.89–6.75 (1H, m, Ar), 6.67–6.55 (1H, m, Ar), 5.63–5.56 (1H, m, CHO), 3.44–3.17 (2H, m, $CH_2$), 2.55–2.23 (2H, m, $CH_2$).

The compounds of Examples 54–60 were prepared by solid phase synthesis as described herein.

ArgoPore™ is obtainable from Argonaut Technologies. The process may be run in a combinatorial fashion such that all possible compounds from sets of precursors X—CO—$CH_3$ and Y—OH may be prepared. The sequence is performed without characterisation of the resin-bound intermediates.

i) A suspension of ArgoPore-Cl (5.0 g, 5.8 mmoles) in methylamine in THF (2 M, 50 mL, 100 mmoles) was agitated gently for 48 hrs. The reaction mixture was filtered, and the resin washed with THF (2×50 mL), DMF (3×50 mL) and MeOH (3×50 mL ) and dried in vacuo at 45° C.

ii) Aliquots (157 mg, 0.182 mmoles) of the resin prepared in step i were dispensed into a Bohdan MiniBlock Synthesiser (Mettler Toledo Ltd) fitted with 10 mL reaction tubes. To each was added a 1.25M solution of a substituted acetophenone in isopropanol (3.65 mL, 4.56 mmoles), a 37% solution of formaldehyde in water (0.4 mL, 4.93 mmoles) and 2M HCl in isopropanol (0.2 mL, 1.0 mmole). The reactions were heated at 80° with orbital shaking for 18 hrs, and then cooled to RT, filtered and washed with MeOH (3×5 mL), 20% diisopropylamine in MeOH (5 mL), MeOH (2×5 mL) and EtOH (4×5 mL).

iii) To each resin was added a 1M solution of sodium borohydride in EtOH/triethyleneglycol dimethyl ether (1/1) (4 mL, 4 mmoles). The reactions were agitated by orbital shaking for 5 hrs, then filtered and washed with EtOH (2×5 mL), MeOH (3×5 mL) and dry THF (4×5 mL).

iv) To each resin was added a 1.81M solution of 7-hydroxybenzo[b]thiophene in 0.72M triphenylphosphine/THF (2.0 mL, 3.62 and 0.74 mmoles respectively) and a 0.97M solution of di-tert. butyl azidodicarboxylate in THF (1.5 mL, 1.46 mmoles). The reactions were agitated by orbital shaking for 41 hrs, the filtered and washed with THF (3×5 mL), DMF (3×5 mL) and THF (4×5 mL).

v) To a suspension of each resin in dry THF (2 mL) was added 1-choroethyl chloroformate (0.2 mL, 0.265 g,. 1.85 mmoles) and diisopropylethylamine (0.15 mL, 0.11 g, 0.86 mmoles). The reactions were agitated by orbital shaking for 4.5 hr, then filtered and each resin washed with THF (2×2 mL). Appropriate filtrates and washings were combined and volatile components removed by vacuum evaporation. Each residue was dissolved in MeOH (4.5 mL) and heated under reflux for 15 hr. The reactions were cooled to RT and the solutions applied to MeOH-washed SCX-2 cartridges (1.0 g/6 mL) (Jones Chromatography). After draining under gravity the cartridges were washed with MeOH (5 mL) and the products then eluted using a 2M solution of ammonia in MeOH (5 mL). Removal of volatile components by vacuum evaporation gave the desired products as racemates in ca. 30% overall yield.

EXAMPLE 54

(3R,3S)-3-(-1-Benzothien-7-yloxy)-N-methyl-3-(4-fluorophenyl)-1-propanamine, m/e 316 [M+H], $\delta_H$ (300 MHz, CDCl3) 7.45 6.97 (8H, m, Ar), 6.56 (1H, d, Ar), 5.45 (1H, dd, ArCHO), 2.88–2.74 (2H, m, $CH_2N$), 2.44 (3H, s, $NCH_3$), 2.33–2.31 (1H, m, CHH), 2.10–1.99 (1H, m, CHH).

The following compounds were also prepared:

EXAMPLE 55

(3R,3S)-3-(-1-Benzothien-7-yloxy)-N-methyl-3-(3-methylphenyl)-1-propanamine m/e 312 [M+H]

EXAMPLE 56

(3R,3S)-3-(-1-Benzothien-7-yloxy)-N-methyl-3-(2-fluorophenyl)-1-propanamine m/e 316 [M+H]

EXAMPLE 57

(3R,3S)-3-(-1-Benzothien-7-yloxy)-N-methyl-3-(3-fluorophenyl)-1-propanamine m/e 316 [M+H]

EXAMPLE 58

(3R,3S)-3-(-1-Benzothien-7-yloxy)-N-methyl-3-(3-methoxyphenyl)-1-propanamine m/e 328 [M+H]

EXAMPLE 59

(3R,3S)-3-(-1-Benzothien-7-yloxy)-N-methyl-3-(3-trifluoromethylphenyl)-1-propanamine m/e 366 [M+H]

EXAMPLE 60

(3R3S)-3-(-1-Benzothien-7-yloxy)-N-methyl-3-(4-trifluoromethylphenyl)-1-propanamine m/e 366 [M+H]

Racemates were separated into their two enantiomers by chiral chromatography on a 25 cm×4.6 mm ID Chiralcel-OD column (Chiral Separations, France) using heptane/ethanol 1:1 as the mobile phase.

EXAMPLE 61

(3R & 3S) 3-(1-Benzothienyl-7-yl(thio)-N-methyl-3-phenyl-1-propanamine

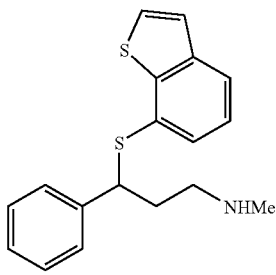

To a solution of 1-benzothien-7-yl(thio)-N-benzyl-N-methyl-3-phenylpropanamine (0.79 g, 1.96 mmol) in dichloromethane (5 mL) was added ACE-Cl (2.1 mL, 19.6 mmol) and polymer supported diethylamine (PS-DIEA) (2 g, 11.76 mmol). The solution was then shaken for 3 h at RT. The resin was then filtered off, washed with dichloromethane (5 mL) and allowed to evaporate. The resulting solid was dissolved in methanol (5 mL) and allowed to stir at 60° C. for 72 h. After this time the reaction was allowed to cool to room temperature. The reaction mixture was purified by an SCX-2 column eluting with methanol followed by ammonia:methanol solution (7 N). The organics were then evaporated to yield a racemic mixture of the title compound. Chiral purification using using a chiralcel, OJ column, 25 cm×4.6 mmid (50% Heptane:50% Ethanol:0.2% DMEA) was then performed to yield each of the desired enantiomers. The resulting oils were dissolved in diethyl ether (10 mL) and an aqueous solution of hydrochloric acid (2 N) was added. The mixture was stirred at room temperature for 10 mins and then the solvent removed in vacuo to yield the target compounds as fluffy white solids (E1: 55 mg, E2: 60 mg; overall yield over 2 steps 10%. (M$^+$H+1 [314]); $\delta_H$ (300 MHz, CDCl$_3$) 7.7 (1H, d, S—C=C), 7.4 (1H, d, S—C=C), 7.3 (1H, d, Ar), 7.1–7.2 (7H, m, Ar), 4.4 (1H, t, S—CH), 2.55 (2H, m, CH$_2$), 2.3 (3H, s, CH$_3$), 2.15 (2H, m, CH$_2$), 1.9 (1H, brs, NH).

EXAMPLE 62

(3R & 3S) 3-(1-Benzothienyl-4-yl(thio)-N-methyl-3-phenyl-1-propanamine hydrochloride

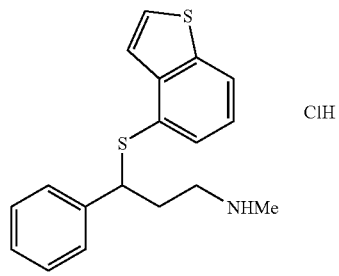

To a solution of benzylated material (0.79 g, 1.96 mmol) in dichloromethane (5 mL) was added ACE-Cl (2.1 mL, 19.6 mmol) and polymer supported diethylamine (PS-DIEA) (2 g, 11.76 mmol). The solution was then shaken for 3 h at RT. The resin was then filtered off, washed with dichloromethane (2×5 mL) and allowed to evaporate. The resulting solid was dissolved in methanol (5 mL) and allowed to stir at 60° C. for 72 h. After this time the reaction was allowed to cool to room temperature. The reaction mixture was purified by an SCX-2 column eluting with methanol followed by ammonia:methanol solution (7 N). The organics were then evaporated to yield a racemic mixture of the title compound. Chiral purification was then performed using a chiralcel, OJ column (40% Heptane: 60% IPA: 0.2% DMEA) to yield each of the desired enantiomers. The resulting oils were dissolved in diethyl ether (10 mL) and a solution of aqueous hydrochloric acid (2 N) was added. The mixture was stirred at room temperature for 10 mins and then the solvent removed in vacuo to yield the target compounds as fluffy white solids (E:1 43 mg, E2: 35 mg), overall yield over 2 steps 7%; LCMS M⁺H+1[314]); $\delta_H$ (300 MHz, CDCl$_3$) 7.7 (1H, s, S—C=C), 7.5 (1H, d, S—S=C), 7.4 (1H, d, Ar), 7.1–7.25 (7H, m, Ar), 4.3 (1H, t, CH), 2.8 (1H, brs, NH), 2.5–2.6 (2H, m, CH$_2$), 2.3 (1H, s, CH$_3$), 2.1–2.2 (2H, m, CH$_2$).

The compounds of the present invention may be used as medicaments in human or veterinary medicine. The compounds may be administered by various routes, for example, by oral or rectal routes, topically or parenterally, for example by injection, and are usually employed in the form of a pharmaceutical composition.

Such compositions may be prepared by methods well known in the pharmaceutical art and normally comprise at least one active compound in association with a pharmaceutically acceptable diluent or carrier. In making the compositions of the present invention, the active ingredient will usually be mixed with a carrier or diluted by a carrier, and/or enclosed within a carrier which may, for example, be in the form of a capsule, sachet, paper or other container. Where the carrier serves as a diluent, it may be solid, semi-solid, or liquid material which acts as a vehicle, excipient or medium for the active ingredient. Thus, the composition may be in the form of tablets, lozenges, sachets, cachets, elixirs, suspensions, solutions, syrups, aerosol (as a solid or in a liquid medium), ointments containing, for example, up to 10% by weight of the active compound, soft and hard gelatin capsules, suppositories, injection solutions and suspensions and sterile packaged powders.

Some examples of suitable carriers are lactose, dextrose, vegetable oils, benzyl alcohols, alkylene glycols, polyethylene glycols, glycerol triacetate, gelatin, carbohydrates such as starch and petroleum jelly, sucrose sorbitol, mannitol, starches, gum acacia,calcium phosphate, alginates, tragacanth, gelatin, syrup, methyl cellulose, methyl- and propyl-hydrobenzoate, talc, magnesium stearate and mineral oil. The compounds of formula (I) can also be lyophilized and the lyophilizates obtained used, for example, for the production of injection preparations. The preparations indicated can be sterilized and/or can contain auxiliaries such as lubricants, preservatives, stabilizers and/or wetting agents, emulsifiers, salts for affecting the osmotic pressure, buffer substances, colourants, flavourings and/or one or more further active compounds, e.g. one or more vitamins.

Compositions of the invention may be formulated so as to provide, quick, sustained or delayed release of the active ingredient after administration to the patient by employing procedures well known in the art.

The compositions are preferably formulated in a unit dosage form, each dosage containing from about 5 to about 500 mg, more usually about 25 to about 300 mg, of the active ingredient. The term "unit dosage form" refers to physically discrete units suitable as unitary doses for human subjects and other mammals, each unit containing a predetermined quantity of active material calculated to produce the desired therapeutic effect, in association with a suitable pharmaceutical carrier.

Scintillation Proximity Assays for Determining the Affinity of Test Ligands at the Norepinephrine and Serotonin Transporters.

The compounds of the invention are norepinephrine and serotonin reuptake inhibitors, and possess excellent activity in, for example, a scintillation proximity assay (e.g. J. Gobel, D. L. Saussy and A. Goetz, J. Pharmacol. Toxicolo. (1999), 42, 237–244). Thus $^3$H-nisoxetine binding to norepinephrine re-uptake sites in a cell line transfected with human norepinephrine transporter binding protein and similarly $^3$H-citalopram binding to serotonin re-uptake sites in a cell line transfected with human serotonin transporter binding protein have been used to determine the affinity of ligands at the norepinephrine and serotonin transporters respectively.

Formalin Paw Assay

The analgesic effect of compounds of the invention for the treatment of persistent nociceptive pain was demonstrated using the well-known "formalin test." The formalin test is a model of persistent nociceptive activation induced by tissue injury which can lead to central sensitization. (Shibata, M., Ohkubo, T., Takahashi, H., and Inoki, R., "Modified formalin test: Characteristic biphasic pain response," *Pain* (1989) 38: 347–352; and Tjolsen, A., Berge, O. G., Hunskaar, S., Rosland, J. H., and Hole, K., "The formalin test: an evaluation of the method," *Pain* (1992) 51:5–17.) The effect of compounds of the invention on formalin-induced paw-licking behavior in the rat was investigated as an index of persistent nociceptive activation. In this test, the injection of formalin under the skin on the dorsal lateral surface of the hind paw of rats causes an immediate and intense increase in the spontaneous activity of C fiber afferents. This activation evokes a distinctly quantifiable behavior indicative of pain, such as licking of the injected paw. The behavioral response to formalin is biphasic, with an early phase that is short lived, followed by an extended tonic response or late phase of persistent nociceptive activation. Mechanisms causing the late phase response, such as central sensitization of pain transmitting neurons, are currently believed to contribute to various types of persistent pains.

Male Sprague-Dawley rats (200–250 g; Charles River, Portage, Mich.) were maintained at constant temperature and light (12 h light/12 h dark) for 4–7 days prior to the studies. Animals had free access to food and water at all times prior to the day of the experiment.

The formalin test was performed in custom made Plexiglass® boxes 25×25×20 cm (length×width×height) in size. A mirror placed at the back of the box allowed the unhindered observation of the formalin injected paw. Rats were acclimatized individually in the cubicles at least 1 hour prior to the experiment. All testing was conducted between 08:00 and 14:00 hr and the testing room temperature was maintained at 21–23° C. Test compound was administered 30 or 60 minutes prior to the formalin injection. Formalin (50 μl of a 5% solution in saline) was injected subcutaneously into the dorsal lateral surface of the right hind paw with a 27 gauge needle. Observation started immediately after the formalin injection. Formalin-induced pain was quantified by recording in 5 minute intervals the number of formalin injected paw licking events and the number of seconds each licking event lasted. These recordings were made for 50 minutes after the formalin injection. Scoring in the formalin test was performed according to Coderre et al., 1993b and Abbott et al., 1995. (Coderre T. J., Fundytus M. E., McKenna J. E., Dalal S. and Melzack R. "The formalin test: a validation of the weighted-scores method of the behavioral pain rating," *Pain*(1993b) 54: 43–50; and Abbott F. V., Franklin K. B. J. and Westbrook R. F. "The formalin test: scoring properties of the first and second phases of the pain response in rats," *Pain* (1995) 60: 91–102.) The sum of time spent licking in seconds from time 0 to 5 minutes was considered the early phase while the late phase was taken as the sum of seconds spent licking from 15 to 40 minutes.

Data are presented as means with standard errors of means (±SEM). Data were evaluated by one-way analysis of variance (ANOVA) and the appropriate contrasts analyzed by Tukey's test and Dunnett "t' test for two-sided comparisons.

The invention claimed is:

1. A compound of formula I:

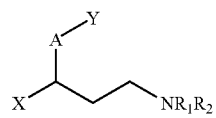

wherein
A is selected from —O— and —S—;
X is selected from phenyl optionally substituted with up to 5 substituents selected from halo, $C_1$–$C_4$ alkyl and $C_1$–$C_4$ alkoxy;
Y is selected from benzothienyl, indolyl and benzofuranyl, optionally substituted with up to 5 substituents selected from halo, $C_1$–$C_4$ alkyl, $C_1$–$C_4$ alkoxy, nitro, acetyl and cyano; and
when Y is indolyl it may be substituted or further substituted by an N-substituent selected from $C_1$–$C_4$ alkyl;
$R_1$ and $R_2$ are each independently H or $C_1$–$C_4$ alkyl;
and pharmaceutically acceptable salts thereof.

2. A compound as claimed in claim 1, wherein A is —O—.
3. A compound as claimed in claim 1, wherein A is —S—.
4. A compound as claimed in any one of claims 1–3, wherein one of $R_1$ and $R_2$ is H.
5. A compound as claimed in any one of claims 1–3, wherein one of $R_1$ and $R_2$ is H and the other is methyl.
6. A compound as claimed in any one of claims 1–3, wherein X is unsubstituted phenyl or phenyl mono- di- or tri-substituted with halo, $C_1$–$C_4$ alkyl or $C_1$–$C_4$ alkoxy.
7. A compound as claimed in any one of claims 1–3, wherein Y is indolyl.
8. A compound as claimed in claim 7, wherein the indolyl group is N-substituted with a methyl substituent.
9. A compound as claimed in any one of claims 1–3, wherein Y is benzofuranyl.
10. A compound as claimed in any one of claims 1–3, wherein Y is benzothienyl.
11. A compound as claimed in any one of claims 1–3, wherein the point of attachment of the group Y to the —O— or —S— atom is attachment at the 7 position.
12. A compound as claimed in any one of claims 1–3, wherein the point of attachment of the group Y to the —O— or —S— atom is attachment at the 4 position.
13. A compound as claimed in any one of claims 1–3, wherein X is phenyl and Y is benzothienyl.
14. A compound as claimed in claim 13, wherein Y halo-substituted benzothienyl.
15. A compound as claimed in claim 13, wherein Y is F-substituted benzothienyl.
16. A pharmaceutical composition comprising a compound of formula I or a pharmaceutically acceptable salt thereof, as defined in claim 1, together with a pharmaceutically acceptable diluent or carrier.
17. A method for treating pain, comprising administering to a patient in need thereof an effective amount of a compound of formula I or a pharmaceutically acceptable salt thereof, as defined in claim 1.
18. A compound as claimed in claim 4, wherein one of $R_1$ and $R_2$ is H and the other is methyl.
19. A compound as claimed in claim 4, wherein X is unsubstituted phenyl or phenyl mono- di- or tri-substituted with halo, $C_1$–$C_4$ alkyl or $C_1$–$C_4$ alkoxy.
20. A compound as claimed in claim 5, wherein X is unsubstituted phenyl or phenyl mono- di- or tri-substituted with halo, $C_1$–$C_4$ alkyl or $C_1$–$C_4$ alkoxy.
21. A compound as claimed in claim 4, wherein Y is indolyl.
22. A compound as claimed in claim 5, wherein Y is indolyl.
23. A compound as claimed in claim 6, wherein Y is indolyl.
24. A compound as claimed in claim 4, wherein Y is benzofuranyl.
25. A compound as claimed in claim 5, wherein Y is benzofuranyl.
26. A compound as claimed in claim 6, wherein Y is benzofuranyl.
27. A compound as claimed in claim 4, wherein Y is benzothienyl.
28. A compound as claimed in claim 5, wherein Y is benzothienyl.
29. A compound as claimed in claim 6, wherein Y is benzothienyl.
30. A compound as claimed in claim 4, wherein the point of attachment of the group Y to the —O— or —S— atom is attachment at the 7 position.
31. A compound as claimed in claim 5, wherein the point of attachment of the group Y to the —O— or —S— atom is attachment at the 7 position.
32. A compound as claimed in claim 6, wherein the point of attachment of the group Y to the —O— or —S— atom is attachment at the 7 position.
33. A compound as claimed in claim 7, wherein the point of attachment of the group Y to the —O— or —S— atom is attachment at the 7 position.
34. A compound as claimed in claim 8, wherein the point of attachment of the group Y to the —O— or —S— atom is attachment at the 7 position.
35. A compound as claimed in claim 9, wherein the point of attachment of the group Y to the —O— or —S— atom is attachment at the 7 position.
36. A compound as claimed in claim 10, wherein the point of attachment of the group Y to the —O— or —S— atom is attachment at the 7 position.
37. A compound as claimed in claim 4, wherein the point of attachment of the group Y to the —O— or —S— atom is attachment at the 4 position.
38. A compound as claimed in claim 5,wherein the point of attachment of the group Y to the —O— or —S— atom is attachment at the 4 position.

39. A compound as claimed in claim 6, wherein the point of attachment of the group Y to the —O— or —S— atom is attachment at the 4 position.

40. A compound as claimed in claim 7, wherein the point of attachment of the group Y to the —O— or —S— atom is attachment at the 4 position.

41. A compound as claimed in claim 4, wherein X is phenyl and Y is benzothienyl.

42. A compound as claimed in claim 5, wherein X is phenyl and Y is benzothienyl.

43. A compound as claimed in claim 6, wherein X is phenyl and Y is benzothienyl.

44. A compound as claimed in claim 10, wherein X is phenyl and Y is benzothienyl.

45. A compound as claimed in claim 11, wherein X is phenyl and Y is benzothienyl.

46. A compound as claimed in claim 12, wherein X is phenyl and Y is benzothienyl.

* * * * *